United States Patent
Fushimi et al.

(10) Patent No.: US 7,541,341 B2
(45) Date of Patent: *Jun. 2, 2009

(54) GLUCOPYRANOSYLOXYBENZYLBENZENE DERIVATIVES AND MEDICINAL USE THEREOF

(75) Inventors: Nobuhiko Fushimi, Nagano (JP); Kazuya Tatani, Nagano (JP); Hideki Fujikura, Nagano (JP); Toshihiro Nishimura, Nagano (JP); Minoru Fujioka, Nagano (JP); Takeshi Nakabayashi, Nagano (JP); Masayuki Isaji, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 153 days.

This patent is subject to a terminal disclaimer.

(21) Appl. No.: 10/467,823

(22) PCT Filed: Feb. 13, 2002

(86) PCT No.: PCT/JP02/01178
§ 371 (c)(1),
(2), (4) Date: Jan. 13, 2004

(87) PCT Pub. No.: WO02/064606
PCT Pub. Date: Aug. 22, 2002

(65) Prior Publication Data
US 2004/0138148 A1 Jul. 15, 2004

(30) Foreign Application Priority Data
Feb. 14, 2001 (JP) .................. 2001-037729

(51) Int. Cl.
A61K 31/70 (2006.01)
C07H 15/00 (2006.01)
C07H 17/00 (2006.01)

(52) U.S. Cl. .................. 514/25; 536/4.1; 536/17.2; 536/17.5; 536/17.9

(58) Field of Classification Search .................. 514/25, 514/35; 536/4.1, 18.1
See application file for complete search history.

(56) References Cited

U.S. PATENT DOCUMENTS 4,598,068 A  7/1986  Samreth et al.
6,683,056 B2 *  1/2004  Washburn et al. .............. 514/25
7,053,060 B2 *  5/2006  Fujikura et al. ................ 514/25

FOREIGN PATENT DOCUMENTS

| WO | WO 01/68660 A1 | 9/2001 |
| WO | WO 01/74834 A1 | 10/2001 |
| WO | WO 02/28872 A1 | 4/2002 |
| WO | WO 02/44192 A1 | 6/2002 |

OTHER PUBLICATIONS

Oku A. et al, Antidiabetic effect of T-1095, an inhibitor of Na(+)-glucose contransporter, in neonatally streptozotocin-treated rats, Eur. J. Pharmacol., 2000, vol. 391, No. 1-2, pp. 183 to 192.

Oku A. et al., Antihyperglycemic effect of T-1095 via inhibition of renal Na+ glucose cotransporters in streptozotocin-induced diabetic rates, Biol. Pharm. Bull., 2000, vol.. 23, No. 12, pp. 1434 to 1437.

* cited by examiner

Primary Examiner—Traviss C McIntosh, III
(74) Attorney, Agent, or Firm—Sughrue Mion, PLLC

(57) ABSTRACT

The present invention provides glucopyranosyloxybenzylbenzene derivatives represented by the general formula:

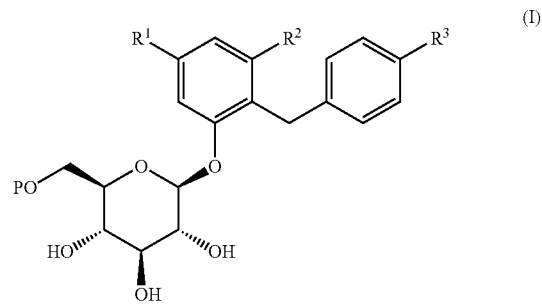

wherein P represents a hydrogen atom or a group forming a prodrug; $R^1$ represents a hydrogen atom, an optionally substituted amino group, a carbamoyl group, an optionally substituted lower alkyl group, an optionally substituted lower alkoxy group, etc.; $R^2$ represents a hydrogen atom or a lower alkyl group; and $R^3$ represents an optionally substituted lower alkyl group, an optionally substituted lower alkoxy group, an optionally substituted lower alkylthio group, etc., which have an improved oral absorption, and exert an inhibitory activity in human SGLT2, and therefore are useful as drugs for the prevention or treatment of a disease associated with hyperglycemia such as diabetes, diabetic complications or obesity, or pharmaceutically acceptable salts thereof, and pharmaceutical uses thereof.

6 Claims, No Drawings

```
                         SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 1
atggaggagc acacagaggc                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 2
ggcatagaag ccccagagga                                               20

<210> SEQ ID NO 3
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 3
```

```
aacctcgaga tggaggagca cacagaggc                                              29

<210> SEQ ID NO 4
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 4
aacaagcttg gcatagaagc cccagagga                                              29

<210> SEQ ID NO 5
<211> LENGTH: 25
<212> TYPE: PRT
<213> ORGANISM: Artificial Sequence
<220> FEATURE:
<223> OTHER INFORMATION: Peptide fused to the carboxyl terminal alanine
      residue of human
      SGLT2

<400> SEQUENCE: 5

Lys Leu Gly Pro Glu Gln Lys Leu Ile Ser Glu Glu Asp Leu Asn Ser
1               5                   10                  15

Ala Val Asp His His His His His His
            20                  25
```

GLUCOPYRANOSYLOXYBENZYLBENZENE DERIVATIVES AND MEDICINAL USE THEREOF

TECHNICAL FIELD

The present invention relates to glucopyranosyloxybenzylbenzene derivatives and pharmaceutically acceptable salts thereof which are useful as medicaments and pharmaceutical uses thereof.

More particularly, the present invention relates to glucopyranosyloxybenzylbenzene derivatives represented by the general formula:

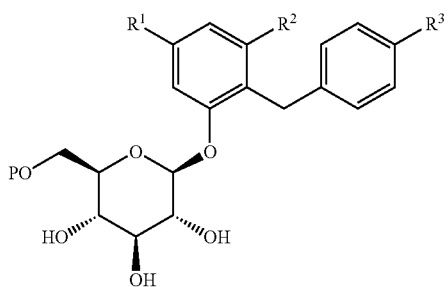

wherein P represents a hydrogen atom or a group forming a prodrug; $R^1$ represents a hydrogen atom, an amino group, a mono or di(lower alkyl)-substituted amino group, a cyano group, a carbamoyl group, a lower alkyl group, a lower alkoxy group, a lower alkoxy-substituted (lower alkyl) group, a lower alkoxy-substituted (lower alkoxy) group, a carbamoyl (lower alkyl) group, a lower alkoxycarbonyl-substituted (lower alkyl) group, a lower alkoxycarbonyl-substituted (lower alkoxy) group, a carboxy(lower alkyl) group, a carboxy(lower alkoxy) group, or a group represented by the general formula: $P^1$—O—$A^1$— wherein $P^1$ represents a hydrogen atom or a group forming a prodrug; and $A^1$ represents a single bond, a lower alkylene group, or a lower alkyleneoxy group; $R^2$ represents a hydrogen atom or a lower alkyl group; $R^3$ represents a lower alkyl group, a lower alkoxy group, a lower alkylthio group, a lower alkenyloxy group, an aralkyloxy group, a lower alkoxy-substituted (lower alkyl) group, a lower alkoxy-substituted (lower alkoxy) group, a lower alkoxy-substituted (lower alkylthio) group, a carboxy group, a lower alkoxycarbonyl group, a cyano group, an aralkyloxy(lower alkyl) group, a cyano(lower alkyl) group, a carbamoyl group, a carbamoyl (lower alkyl) group, an amino group, a mono or di (lower alkyl)-substituted amino group, a lower alkoxycarbonyl-substituted (lower alkyl) group, a lower alkoxycarbonyl-substituted (lower alkoxy) group, a carboxy(lower alkyl) group, a carboxy(lower alkoxy) group, or a group represented by the general formula: $P^2$—O—A— wherein $P^2$ represents a hydrogen atom or a group forming a prodrug; and $A^2$ represents a lower alkylene group, a lower alkyleneoxy group, a lower alkylenethio group, or a lower alkenylene group; and with the proviso that at least one of P, $P^1$ and $P^2$ represents a group forming a prodrug, and when $R^3$ represents a lower alkyl group, a lower alkoxy group, a lower alkylthio group, a lower alkoxy-substituted (lower alkyl) group, a lower alkoxy-substituted (lower alkoxy) group or a lower alkoxy-substituted (lower alkylthio) group, both of $R^1$ and $R^2$ do not represent hydrogen atoms, or pharmaceutically acceptable salts thereof, which are useful as agents for the prevention or treatment of a disease such as diabetes, diabetic complications or obesity, of which glucopyranosyloxybenzylbenzene derivatives, which have an inhibitory activity in human SGLT2, represented by the general formula:

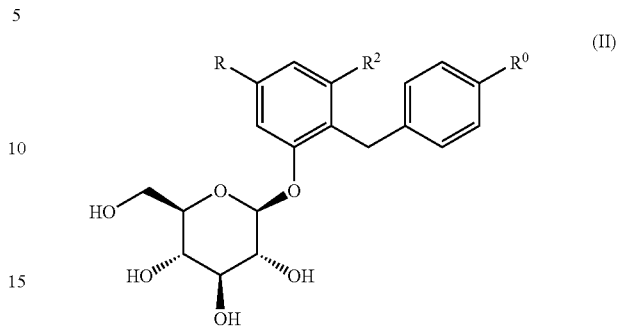

wherein R represents a hydrogen atom, an amino group, a mono or di(lower alkyl)-substituted amino group, a cyano group, a carbamoyl group, a lower alkyl group, a lower alkoxy group, a lower alkoxy-substituted (lower alkyl), a lower alkoxy-substituted (lower alkoxy) group, a carbamoyl(lower alkyl) group, a lower alkoxycarbonyl-substituted (lower alkyl) group, a lower alkoxycarbonyl-substituted (lower alkoxy) group, a carboxy(lower alkyl) group, a carboxy (lower alkoxy) group, or a group represented by the general formula: HO—$A^1$— wherein $A^1$ represents a single bond, a lower alkylene group, or a lower alkyleneoxy group; $R^2$ represents a hydrogen atom or a lower alkyl group; $R^0$ represents a lower alkyl group, a lower alkoxy group, a lower alkylthio group, a lower alkenyloxy group, an aralkyloxy group, a lower alkoxy-substituted (lower alkyl) group, a lower alkoxy-substituted (lower alkoxy) group, a lower alkoxy-substituted (lower alkylthio) group, a carboxy group, a lower alkoxycarbonyl group, a cyano group, an aralkyloxy(lower alkyl) group, a cyano(lower alkyl) group, a carbamoyl group, a carbamoyl (lower alkyl) group, an amino group, a mono or di (lower alkyl)-substituted amino group, a lower alkoxycarbonyl-substituted (lower alkyl) group, a lower alkoxycarbonyl-substituted (lower alkoxy) group, a carboxy(lower alkyl) group, a carboxy(lower alkoxy) group, or a group represented by the general formula: HO—$A^2$— wherein $A^2$ represents a lower alkylene group, a lower alkyleneoxy group, a lower alkylenethio group, or a lower alkenylene group; and with the proviso that both of R and $R^2$ do not represent hydrogen atoms when $R^0$ represents a lower alkyl group, a lower alkoxy group, a lower alkylthio group, a lower alkoxy-substituted (lower alkyl) group, a lower alkoxy-substituted (lower alkoxy) group or a lower alkoxy-substituted (lower alkylthio) group, a reactive forms, and to pharmaceutical uses thereof.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. Now, biguanides, sulfonylureas and insulin sensitivity enhancers have been employed as antidiabetic agents. However, biguanides and sulfonylureas show occasionally adverse effects such as lactic acidosis and hypoglycemia, respectively. In a case of using agents for reducing insulin resistance, adverse effects such as edema are occasionally observed, and it is also concerned for advancing obesity. Therefore, in order to solve these problems, it has been desired to develop antidiabetic agents having a new mechanism.

In recent years, development of new type antidiabetic agents has been progressing, which promote urinary glucose excretion and lower blood glucose level by preventing excess glucose reabsorption at the kidney (J. Clin. Invest., Vol. 79, pp. 1510-1515 (1987)). In addition, it is reported that SGLT2 ($Na^+$/glucose cotransporter 2) is present in the S1 segment of the kidney's proximal tubule and participates mainly in reabsorption of glucose filtrated through glomerular (J. Clin. Invest., Vol. 93, pp. 397-404 (1994)). Accordingly, inhibiting a human SGLT2 activity prevents reabsorption of excess glucose at the kidney, subsequently promotes excreting excess glucose though the urine, and normalizes blood glucose level. Therefore, fast development of antidiabetic agents which have a potent inhibitory activity in human SGLT2 and have a new mechanism has been desired. In addition, since such agents promote the excretion of excess glucose though the urine and consequently the glucose accumulation in the body is decreased, they are also expected to have a preventing or alleviating effect on obesity and a urinating effect. Furthermore, the agents are considered to be useful for various related diseases which occur accompanying the progress of diabetes or obesity due to hyperglycemia.

DISCLOSURE OF THE INVENTION

The present inventors have studied earnestly to find compounds having an inhibitory activity in human SGLT2. As a result, it was found that compounds represented by the above general formula (I) are converted into glucopyranosyloxybenzylbenzene derivatives represented by the above general formula (II) as their active forms in vivo, and show an excellent inhibitory activity in human SGLT2 as mentioned below, thereby forming the basis of the present invention.

The present invention is to provide the following glucopyranosyloxybenzylbenzene derivatives and pharmaceutically acceptable salts thereof, which exert an inhibitory activity in human SGLT2 in vivo and show an excellent hypoglycemic effect by excreting excess glucose in the urine through preventing the reabsorption of such glucose at the kidney, and pharmaceutical uses thereof.

This is, the present invention relates to a glucopyranosyloxybenzylbenzene derivative represented by the general formula:

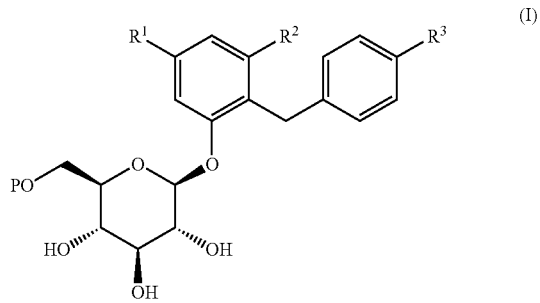

(I)

wherein P represents a hydrogen atom or a group forming a prodrug; $R^1$ represents a hydrogen atom, an amino group, a mono or di (lower alkyl)-substituted amino group, a cyano group, a carbamoyl group, a lower alkyl group, a lower alkoxy group, a lower alkoxy-substituted (lower alkyl), a lower alkoxy-substituted (lower alkoxy) group, a carbamoyl(lower alkyl) group, a lower alkoxycarbonyl-substituted (lower alkyl) group, a lower alkoxycarbonyl-substituted (lower alkoxy) group, a carboxy(lower alkyl) group, a carboxy (lower alkoxy) group, or a group represented by the general formula: $P^1$—O—$A^1$— wherein $P^1$ represents a hydrogen atom or a group forming a prodrug; and $A^1$ represents a single bond, a lower alkylene group, or a lower alkyleneoxy group; $R^2$ represents a hydrogen atom or a lower alkyl group; $R^3$ represents a lower alkyl group, a lower alkoxy group, a lower alkylthio group, a lower alkenyloxy group, an aralkyloxy group, a lower alkoxy-substituted (lower alkyl) group, a lower alkoxy-substituted (lower alkoxy) group, a lower alkoxy-substituted (lower alkylthio) group, a carboxy group, a lower alkoxycarbonyl group, a cyano group, an aralkyloxy (lower alkyl) group, a cyano(lower alkyl) group, a carbamoyl group, a carbamoyl (lower alkyl) group, an amino group, a mono or di (lower alkyl)-substituted amino group, a lower alkoxycarbonyl-substituted (lower alkyl) group, a lower alkoxycarbonyl-substituted (lower alkoxy) group, a carboxy (lower alkyl) group, a carboxy(lower alkoxy) group, or a group represented by the general formula: $P^2$—O—A— wherein $P^2$ represents a hydrogen atom or a group forming a prodrug; and $A^2$ represents a lower alkylene group, a lower alkyleneoxy group, a lower alkylenethio group, or a lower alkenylene group; and with the proviso that at least one of P, $P^1$ and $P^2$ represents a group forming a prodrug, and when $R^3$ represents a lower alkyl group, a lower alkoxy group, a lower alkylthio group, a lower alkoxy-substituted (lower alkyl) group, a lower alkoxy-substituted (lower alkoxy) group or a lower alkoxy-substituted (lower alkylthio) group, both of $R^1$ and $R^2$ do not represent hydrogen atoms, or a pharmaceutically acceptable salt thereof.

The present invention relates to a pharmaceutical composition, a human SGLT2 inhibitor and an agent for the prevention or treatment of a disease associated with hyperglycemia, which comprises as the active ingredient a glucopyranosyloxybenzylbenzene derivative represented by the above general formula (I) or a pharmaceutically acceptable salt thereof.

The present invention relates to a method for the prevention or treatment of a disease associated with hyperglycemia, which comprises administering an effective amount of a glucopyranosyloxybenzylbenzene derivative represented by the above general formula (I) or a pharmaceutically acceptable salt thereof.

The present invention relates to a use of a glucopyranosyloxybenzylbenzene derivative represented by the above general formula (I) or a pharmaceutically acceptable salt thereof for the manufacture of a pharmaceutical composition for the prevention or treatment of a disease associated with hyperglycemia.

Furthermore, the present invention relates to a pharmaceutical combination which comprises (A) a glucopyranosyloxybenzylbenzene derivative represented by the above general formula (I) or a pharmaceutically acceptable salt thereof, and (B) at least one member selected from the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a β$_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an α$_2$-adrenoceptor agonist, an antiplatelets agent, a uric acid synthesis inhibitor, a uricosuric agent and a urinary alkalinizer.

The present invention relates to a method for the prevention or treatment of a disease associated with hyperglycemia, which comprises administering an effective amount of (A) a glucopyranosyloxybenzylbenzene derivative represented by the above general formula (I) or a pharmaceutically acceptable salt thereof, in combination with (B) at least one member selected from the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a β$_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an α$_2$-adrenoceptor agonist, an antiplatelets agent, a uric acid synthesis inhibitor, a uricosuric agent and a urinary alkalinizer.

The present invention relates to a use of (A) a glucopyranosyloxybenzylbenzene derivative represented by the above general formula (I) or a pharmaceutically acceptable salt thereof, and (B) at least one member selected from the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a β$_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an α$_2$-adrenoceptor agonist, an antiplatelets agent, a uric acid synthesis inhibitor, a uricosuric agent and a urinary alkalinizer, for the manufacture of a pharmaceutical composition for the prevention or treatment of a disease associated with hyperglycemia.

In the present invention, the term "prodrug" means a compound which is converted into a glucopyranosyloxybenzylbenzene derivative represented by the above general formula (II) as an active form thereof in vivo. As examples of groups forming prodrugs, a hydroxy-protective group used generally as a prodrug, such as a lower acyl group, a lower alkoxy-substituted (lower acyl) group, a lower alkoxycarbonyl-substituted (lower acyl) group, a lower alkoxycarbonyl group and a lower alkoxy-substituted (lower alkoxycarbonyl) group, are illustrated.

As the glucopyranoxyloxybenzylbenzene derivatives represented by the above general formula (I), for example, compounds represented by the general formula:

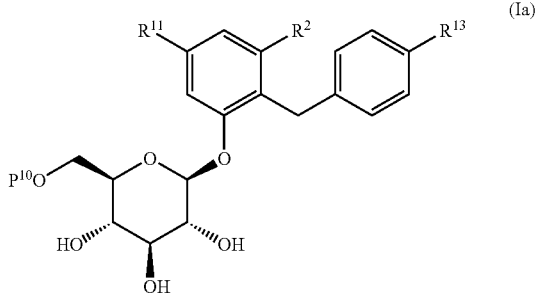

(Ia)

wherein $P^{10}$ represents a hydrogen atom, a lower acyl group, a lower alkoxy-substituted (lower acyl) group, a lower alkoxycarbonyl-substituted (lower acyl) group, a lower alkoxycarbonyl group or a lower alkoxy-substituted (lower alkoxycarbonyl) group; $R^{11}$ represents a hydrogen atom, an amino group, a mono or di(lower alkyl)-substituted amino group, a cyano group, a carbamoyl group, a lower alkyl group, a lower alkoxy group, a lower alkoxy-substituted (lower alkyl), a lower alkoxy-substituted (lower alkoxy) group, a carbamoyl(lower alkyl) group, a lower alkoxycarbonyl-substituted (lower alkyl) group, a lower alkoxycarbonyl-substituted (lower alkoxy) group, a carboxy(lower alkyl) group, a carboxy(lower alkoxy) group or a group represented by the general formula: $P^{11}$—O—$A^1$— wherein $P^{11}$ represents a hydrogen atom, a lower acyl group, a lower alkoxy-substituted (lower acyl) group, a lower alkoxycarbonyl-substituted (lower acyl) group, a lower alkoxycarbonyl group and a lower alkoxy-substituted (lower alkoxycarbonyl) group; and $A^1$ represents a single bond, a lower alkylene group or a lower alkyleneoxy group; $R^2$ represents a hydrogen atom or a lower alkyl group; $R^{13}$ represents a lower alkyl group, a lower alkoxy group, a lower alkylthio group, a lower alkenyloxy group, an aralkyloxy group, a lower alkoxy-substituted (lower alkyl) group, a lower alkoxy-substituted (lower alkoxy) group, a lower alkoxy-substituted (lower alkylthio) group, a carboxy group, a lower alkoxycarbonyl group, a cyano group, an aralkyloxy(lower alkyl) group, a cyano (lower alkyl) group, a carbamoyl group, a carbamoyl (lower alkyl) group, an amino group, a mono or di (lower alkyl)-substituted amino group, a lower alkoxycarbonyl-substituted (lower alkyl) group, a lower alkoxycarbonyl-substituted (lower alkoxy) group, a carboxy(lower alkyl) group, a carboxy(lower alkoxy) group or a group represented by the general formula: $P^{12}$—O—$A^2$— wherein $P^{12}$ represents a hydrogen atom, a lower acyl group, a lower alkoxy-substituted (lower acyl) group, a lower alkoxycarbonyl-substituted (lower acyl) group, a lower alkoxycarbonyl group or a lower alkoxy-substituted (lower alkoxycarbonyl) group; and $A^2$ represents a lower alkylene group, a lower alkyleneoxy group, a lower alkylenethio group or a lower alkenylene group; and with the proviso that at least one of $P^{10}$, $P^{11}$ and $P^{12}$ represents a lower acyl group, a lower alkoxy-substituted (lower acyl) group, a lower alkoxycarbonyl-substituted (lower acyl) group, a lower alkoxycarbonyl group or a lower alkoxy-substituted (lower alkoxycarbonyl) group, and when $R^{13}$ represents a lower alkyl group, a lower alkoxy group, a lower alkylthio group, a lower alkoxy-substituted (lower alkyl) group, a lower alkoxy-substituted (lower alkoxy) group or a lower alkoxy-substituted (lower alkylthio) group, both of $R^{11}$ and $R^2$ do not represent hydrogen atoms, or pharmaceutically acceptable salts thereof are illustrated.

The present invention also relates to glucopyranosyloxybenzylbenzene derivative represented by the general formula:

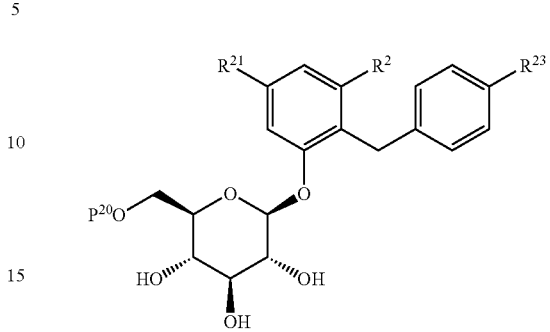

wherein $P^{20}$ represents a hydrogen atom, a lower acyl group or a lower alkoxycarbonyl group; $R^{21}$ represents a hydrogen atom, an amino group, a mono or di(lower alkyl)-substituted amino group, a cyano group, a carbamoyl group, a lower alkyl group, a lower alkoxy group, a lower alkoxy-substituted (lower alkyl) group, a lower alkoxy-substituted (lower alkoxy) group, a carbamoyl(lower alkyl) group, a lower alkoxycarbonyl-substituted (lower alkyl) group, a lower alkoxycarbonyl-substituted (lower alkoxy) group, a carboxy (lower alkyl) group, a carboxy(lower alkoxy) group or a group represented by the general formula: $P^{21}$-O-$A^1$-wherein $P^{21}$ represents a hydrogen atom, a lower acyl group or a lower alkoxycarbonyl group; and $A^1$ represents a single bond, a lower alkylene group or a lower alkyleneoxy group; $R^2$ represents a hydrogen atom or a lower alkyl group; $R^{23}$ represents a lower alkyl group, a lower alkoxy group, a lower alkylthio group, a lower alkenyloxy group, an aralkyloxy group, a lower alkoxy-substituted (lower alkyl) group, a lower alkoxy-substituted (lower alkoxy) group, a lower alkoxy-substituted (lower alkylthio) group, a carboxy group, a lower alkoxycarbonyl group, a cyano group, an aralkyloxy (lower alkyl) group, a cyano(lower alkyl) group, a carbamoyl group, a carbamoyl(lower alkyl) group, an amino group, a mono or di(lower alkyl)-substituted amino group, a lower alkoxycarbonyl-substituted (lower alkyl) group, a lower alkoxycarbonyl- substituted (lower alkoxy) group, a carboxy (lower alkyl) group, a carboxy(lower alkoxy) group or a group represented by the general formula: $P^{22}$-O-$A^2$- wherein $P^{22}$ represents a hydrogen atom, a lower acyl group or a lower alkoxycarbonyl group; and $A^2$ represents a lower alkylene group, a lower alkyleneoxy group, a lower alkylenethio group or a lower alkenylene group; and with the proviso that both of $R^{21}$ and $R^2$ do not represent hydrogen atoms when at least one of $P^{20}$, $P^{21}$ and $P^{22}$ represents a lower acyl group or a lower alkoxycarbonyl group and $R^{23}$ represents a lower alkyl group, a lower alkoxy group, a lower alkylthio group, a lower alkoxy-substituted (lower alkyl) group, a lower alkoxy-substituted (lower alkoxy) group or a lower alkoxy-substituted (lower alkylthio) group, or a pharmaceutically acceptable salt thereof.

In the present invention, the term "lower alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "lower alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; and the term "lower alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like. The term "lower alkoxy-substituted (lower alkyl) group" means the above lower alkyl group substituted by the above lower alkoxy group; the term "lower alkoxy-substituted (lower alkoxy) group means the above lower alkoxy group substituted by the above lower alkoxy group; and the term "lower alkoxy-substituted (lower alkylthio) group means the above lower alkylthio group substituted by the above lower alkoxy group. The term "lower alkylene group" means a straight-chained or branched alkylene group having 1 to 6 carbon atoms such as a methylene group, an ethylene group, a trimethylene group, a propylene group or the like; the term "lower alkyleneoxy group" means a straight-chained or branched alkyleneoxy group having 1 to 6 carbon atoms; the term "lower alkylenethio group" means a straight-chained or branched alkylenethio group having 1 to 6 carbon atoms; and the term "lower alkenylene group" means a straight-chained or branched alkenylene group having 3 to 6 carbon atoms such as a 1-propenylene group or the like. The term "lower alkenyloxy group" means a straight-chained or branched alkenyloxy group having 2 to 6 carbon atoms such as an allyloxy group or the like; the term "aralkyloxy group" means the above lower alkoxy group substituted by an aryl group such as a phenyl group, a naphthyl group, such as a benzyloxy group or the like; the term "aralkyloxy(lower alkyl) group" means the above lower alkyl group substituted by the above aralkyloxy group; the term "cyano(lower alkyl) group" means the above lower alkyl group substituted by a cyano group; the term "carbamoyl (lower alkyl) group" means the above lower alkyl group substituted by a carbamoyl group; and the term "mono or di(lower alkyl)-substituted amino group" means an amino group mono- or di-substituted by the above lower alkyl group. The term "lower alkoxycarbonyl group" means a straight-chained, branched or cyclic alkoxycarbonyl group having 2 to 7 carbon atoms such as a methoxycarbonyl group, an ethoxycarbonyl group, a propyloxycarbonyl group, an isopropyloxycarbonyl group, a butyloxycarbonyl group, an isobutyloxycarbonyl group, a sec-butyloxycarbonyl group, a tert-butyloxycarbonyl group, a pentyloxycarbonyl group, an isopentyloxycarbonyl group, a neopentyloxycarbonyl group, a tert-pentyloxycarbonyl group, a hexyloxycarbonyl group, and a cyclohexyloxycarbonyl group or the like; the term "lower alkoxycarbonyl-substituted (lower alkyl) group" means the above lower alkyl group substituted by the above lower alkoxycarbonyl group; the term "lower alkoxycarbonyl-substituted (lower alkoxy) group" means the above lower alkoxy group substituted by the above lower alkoxycarbonyl group; and the term "lower alkoxy-substituted (lower alkoxycarbonyl) group means the above lower alkoxycarbonyl group substituted by the above alkoxy group such as a 2-methoxyethoxycarbonyl group. The term "carboxy(lower alkyl) group" means the above lower alkyl group substituted by a carboxy group; and the term "carboxy(lower alkoxy) group" means the above lower alkoxy group substituted by a carboxy group. The term "lower acyl group" means a straight-chained, branched or cyclic acyl group having 2 to 7 carbon atoms such as an acetyl group, a propionyl group, a butyryl group, an isobutyryl group, a pivaloyl group, a hexanoyl group and a cyclohexylcarbonyl group; and the term "lower alkoxy-substituted (lower acyl) group means the above lower acyl group substituted by the above lower alkoxy group; the term "lower alkoxycarbonyl-substituted (lower acyl) group" means the above lower acyl group substituted by the above lower alkoxycarbonyl group such as a 3-(ethoxycarbonyl) propionyl group.

As a group forming a prodrug in the prevent invention, a lower acyl group or a lower alkoxycarbonyl group is preferable. As compounds of the present invention, prodrugs of 2-(4-ethylbenzyl)-5-hydroxymethylphenyl β-D-glucopyranoside or 2-[4-(2-hydroxyethyl)benzyl]phenyl β-D-glucopyranoside, such as 2-(4-ethylbenzyl)-5-hydroxymethylphenyl 6-O-ethoxycarbonyl-β-D-glucopyranoside, 2-(4-ethylbenzyl)-5-pivaloyloxymethylphenyl β-D-glucopyranoside, 2-(4-ethylbenzyl)-5-hydroxymethylphenyl 6-O-butyryl-β-D-glucopyranoside, 5-acetoxymethyl-2-(4-ethylbenzyl)phenyl 6-O-acetyl-β-D-glucopyranoside, 2-(4-ethylbenzyl)-5-(ethoxycarbonyloxymethyl)phenyl β-D-glucopyranoside, 2-(4-ethylbenzyl)-5-hydroxymethylphenyl 6-O-hexanoyl-β-D-glucopyranoside, 2-(4-ethylbenzyl)-5-hydroxymethylphenyl 6-O-pivaloyl-β-D-glucopyranoside, 2-(4-ethylbenzyl)-5-hydroxymethylphenyl 6-O-isobutyl-oxycarbonyl-β-D-glucopyranoside, 2-(4-ethylbenzyl)-5-hydroxymethylphenyl 6-O-isopropyloxycarbonyl-β-D-glucopyranoside, 2-[4-(2-hydroxyethyl)benzyl]phenyl 6-O-ethoxycarbonyl-β-D-glucopyranoside, 2-[4-(2-hydroxyethyl)benzyl]phenyl 6-O-acetyl-β-D-glucopyranoside, 2-[4-(2-acetoxyethyl)benzyl]phenyl 6-O-acetyl-β-D-glucopyranoside or the like, are preferable.

The compounds represented by the above general formula (I) of the present invention can be prepared, for example, by introducing a hydroxy-protective group usable in a prodrug into a hydroxy group of a glucopyranoxyloxybenzylbenzene derivative represented by the following general formula (III) according to the following procedure or analogous procedures thereof:

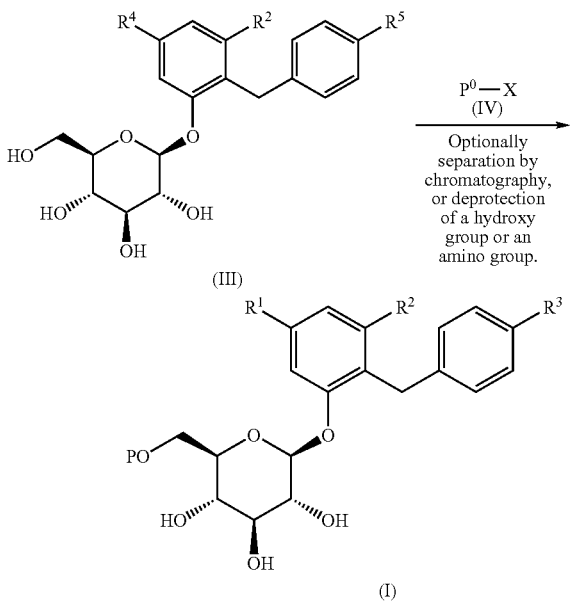

wherein $P^0$ represents a group forming a prodrug; $R^4$ represents a hydrogen atom, an optionally protected amino group, an optionally protected mono (lower alkyl)-substituted amino group, a di(lower alkyl)-substituted amino group, a cyano group, a carbamoyl group, a lower alkyl group, a lower alkoxy group, a lower alkoxy-substituted (lower alkyl) group, a lower alkoxy-substituted (lower alkoxy) group, a carbamoyl (lower alkyl) group, a lower alkoxycarbonyl-substituted (lower alkyl) group, a lower alkoxycarbonyl-substituted (lower alkoxy) group, a carboxy(lower alkyl) group, a carboxy(lower alkoxy) group or a group represented by the general formula: $P^{31}$—O—$A^1$— wherein $P^{31}$ represents a hydrogen atom or a hydroxy-protective group; and $A^1$ represents a single bond, a lower alkylene group or a lower alkyleneoxy group; $R^5$ represents a lower alkyl group, a lower alkoxy group, a lower alkylthio group, a lower alkenyloxy group, an aralkyloxy group, a lower alkoxy-substituted (lower alkyl) group, a lower alkoxy-substituted (lower alkoxy) group, a lower alkoxy-substituted (lower alkylthio) group, a carboxy group, a lower alkoxycarbonyl group, a cyano group, an aralkyloxy(lower alkyl) group, a cyano(lower alkyl) group, a carbamoyl group, a carbamoyl(lower alkyl) group, an optionally protected amino group, an optionally protected mono (lower alkyl)-substituted amino group, a di(lower alkyl)-substituted amino group, a lower alkoxycarbonyl-substituted (lower alkyl) group, a lower alkoxycarbonyl-substituted (lower alkoxy) group, a carboxy(lower alkyl) group, a carboxy(lower alkoxy) group or a group represented by the general formula: $P^{32}$—O—$A^2$— wherein $P^{32}$ represents a hydrogen atom or a hydroxy-protective group; and $A^2$ represents a lower alkylene group, a lower alkyleneoxy group, a lower alkylenethio group or a lower alkenylene group; X represents a leaving group such as a bromine atom or a chlorine atom; and P, $R^1$, $R^2$ and $R^3$ have the same meanings as defined above.

A prodrug represented by the above general formula (I) can be prepared by protecting a hydroxy group of a glucopyranoxyloxybenzylbenzene derivative represented by the above general formula (III) with a reagent for protecting represented by the above general formula (IV) in the presence of a base such as pyridine, triethylamine, N,N-diisopropylethylamine, picoline, lutidine, collidine, quinuclidine, 1,2,2,6,6-pentamethylpiperidine or 1,4-diazabicyclo[2.2.2]octane in an inert solvent or without any solvent, occasionally followed by isolating the desired compound using column chromatography etc. or removing the hydroxy- and/or amino-protective group in conventional means. As the inert solvent used in the reaction to prepare a prodrug, dichloromethane, acetonitrile, ethyl acetate, diisopropyl ether, chloroform, tetrahydrofuran, 1,2-dimethoxyethane, 1,4-dioxane, acetone, tert-butanol, a mixed solvent thereof and the like can be illustrated. The reaction temperature is usually from −40° C. to reflux temperature, and the reaction time is usually from 30 minutes to 2 days, varying based on a used starting material, solvent and reaction temperature.

For example, the compounds represented by the above general formula (III) which are used as starting materials in the aforementioned production process can be prepared according to the following procedure:

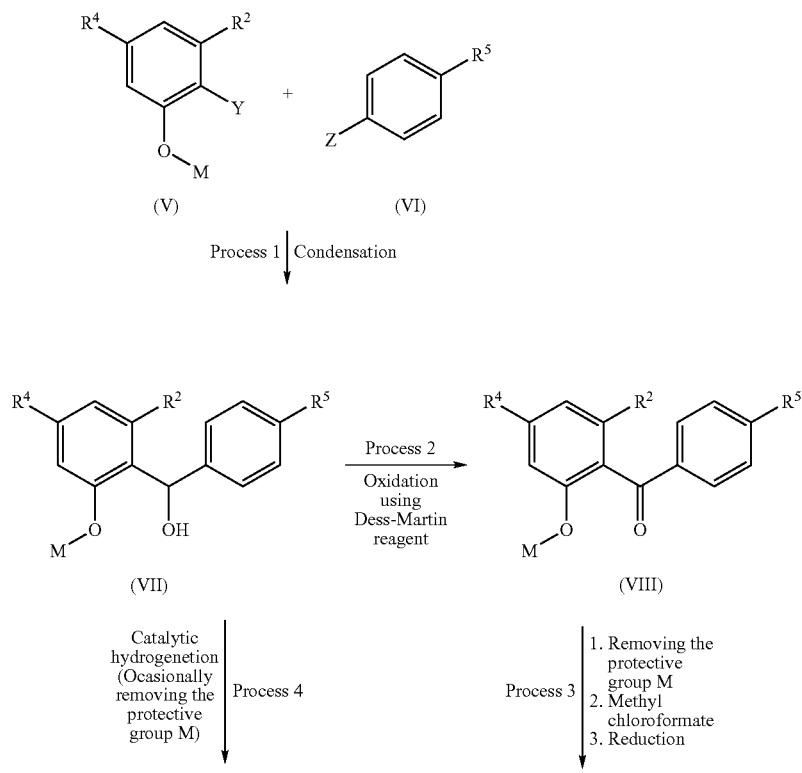

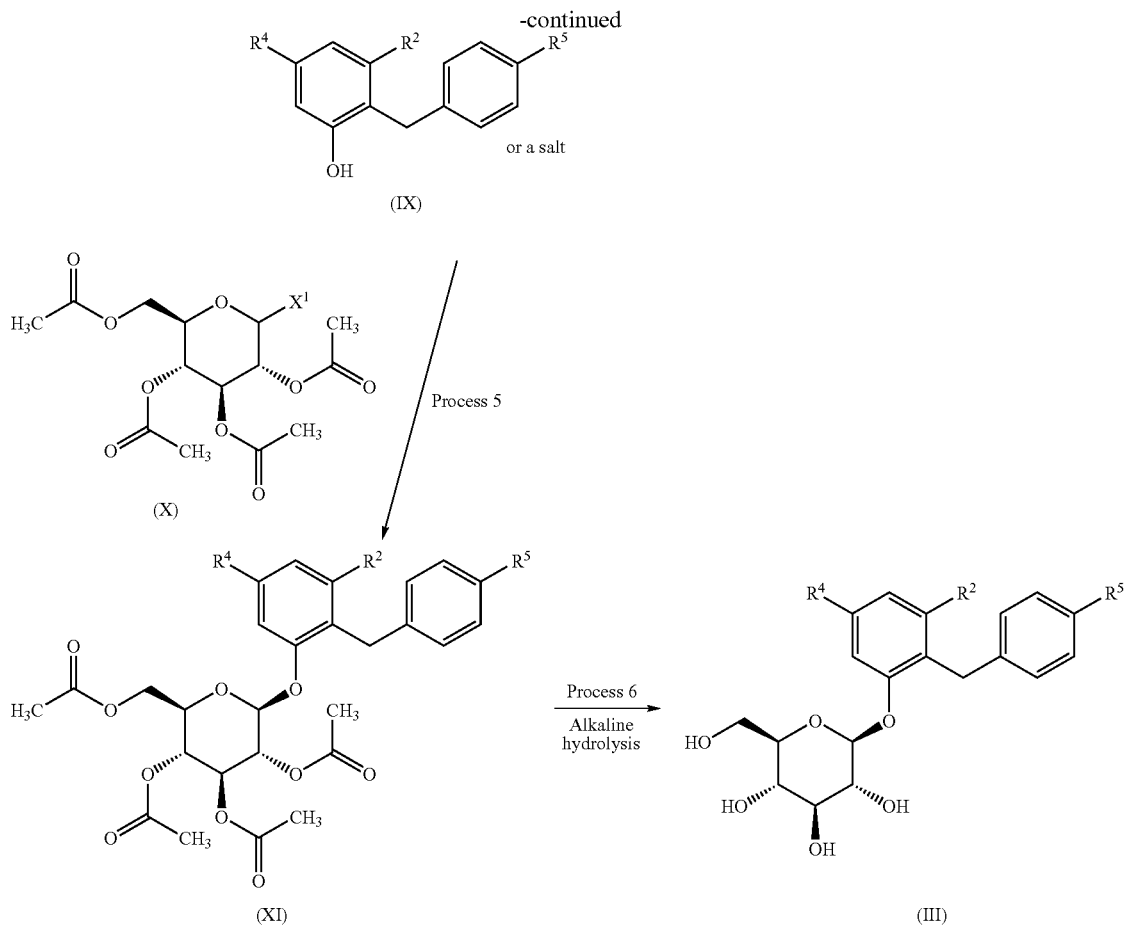

wherein M represents a hydroxy-protective group; $X^1$ represents a leaving group such as a trichloroacetoimidoyloxy group, an acetoxy group, a bromine atom or a fluorine atom; one of Y and Z is MgBr, MgCl, MgI or a lithium atom, while the other is a formyl group; and $R^2$, $R^4$ and $R^5$ have the same meanings as defined above.

Process 1

A compound represented by the above general formula (VII) can be prepared by condensing a benzaldehyde derivative represented by the above general formula (V) with a Grignard reagent or a lithium reagent represented by the above general formula (VI), or by condensing a Grignard reagent or a lithium reagent represented by the above general formula (V) with a benzaldehyde derivative represented by the above general formula (VI) in an inert solvent. As the solvent used, tetrahydrofuran, diethyl ether, a mixed solvent thereof and the like can be illustrated. The reaction temperature is usually from −78° C. to reflux temperature, and the reaction time is usually from 10 minutes to 1 day, varying based on a used starting material, solvent and reaction temperature.

Process 2

A compound represented by the above general formula (VIII) can be prepared by subjecting a compound represented by the above formula (VII) to oxidation using a Dess-Martin reagent in an inert solvent. As the solvent used, dichloromethane, chloroform, acetonitrile, a mixed solvent thereof and the like can be illustrated. The reaction temperature is usually from 0° C. to reflux temperature, and the reaction time is usually from 1 hour to 1 day, varying based on a used starting material, solvent and reaction temperature.

Process 3

A compound represented by the above general formula (IX) can be prepared by removing the protective group M of a compound represented by the above general formula (VIII) in conventional means, condensing the resulting compound with methyl chloroformate in the presence of a base such as triethylamine, diisopropylethylamine or N,N-dimethylaminopyridine in an inert solvent, and subjecting the resulting carbonate derivative to reduction using a reducing agent such as sodium borohydride. As the solvent used in the condensation reaction, tetrahydrofuran, dichloromethane, acetonitrile, ethyl acetate, diethyl ether, a mixed solvent thereof and the like can be illustrated. The reaction temperature is usually from 0° C. to reflux temperature, and the reaction time is usually from 30 minutes to 1 day, varying based on a used starting material, solvent and reaction temperature. As the solvent used in the reduction reaction, a mixed solvent with tetrahydrofuran and water, and the like can be illustrated. The reaction temperature is usually from 0° C. to reflux temperature, and the reaction time is usually from 1 hour to 1 day, varying based on a used starting material, solvent and reaction temperature. The compound represented by the above general formula (IX) can be converted into a salt thereof such as a sodium salt or a potassium salt in the usual way.

Process 4

A compound represented by the above general formula (IX) can be prepared by subjecting a compound represented by the above general formula (VII) to catalytic hydrogenation using a palladium catalyst such as palladium-carbon powder in the presence or absence of an acid such as hydrochloric acid in an inert solvent, and removing a protective group M in the usual way as occasion demands. As the solvent used in the catalytic hydrogenation, methanol, ethanol, tetrahydrofuran, ethyl acetate, acetic acid, isopropanol, a mixed solvent thereof and the like can be illustrated. The reaction temperature is usually from room temperature to reflux temperature, and the reaction time is usually from 30 minutes to 1 day, varying based on a used starting material, solvent and reaction temperature. The compound represented by the above general formula (IX) can be converted into a salt thereof such as a sodium salt or a potassium salt in the usual way.

In the above general formulae (V), (VI), (VII), (VIII) and (IX) in the above processes 1 to 4, a compound wherein $R^4$ represents an optionally protected amino group, an optionally protected mono(lower alkyl)-substituted amino group, a di(lower alkyl)-substituted amino group, a cyano group, a carbamoyl group, a carbamoyl(lower alkyl) group, a lower alkoxycarbonyl-substituted (lower alkyl) group, a carboxy (lower alkyl) group or a group represented by the general formula: $P^{31}$—O—$A^{11}$— wherein $P^{31}$ represents a hydrogen atom or a hydroxy-protective group; and $A^{11}$ represents a lower alkylene group; and/or $R^5$ represents a cyano group, a cyano(lower alkyl) group, a carbamoyl group, a carbamoyl (lower alkyl) group, an optionally protected amino group, an optionally protected mono(lower alkyl)-substituted amino group, a di(lower alkyl)-substituted amino group, a lower alkoxycarbonyl-substituted (lower alkyl) group, a carboxy (lower alkyl) group or a group represented by the general formula: $P^{32}$—O—$A^{12}$— wherein $P^{32}$ represents a hydrogen atom or a hydroxy-protective group; and $A^{12}$ represents a lower alkylene group or a lower alkenylene group can be converted into a corresponding compound with a lower alkoxycarbonyl group as a substituent group in an usual way and then can be subjected to the next processes 1 to 6.

Process 5

A glucoside represented by the above general formula (XI) can be prepared by subjecting a benzylphenol derivative represented by the above general formula (IX) or a salt thereof to glucosidation using a glycosyl-donor represented by the above general formula (X) such as 2,3,4,6-tetra-O-acetyl-1-O-trichloroacetoimidoyl-α-D-glucopyranose, 2,3,4,6-tetra-O-acetyl-1-O-trichloroacetoimidoyl-β-D-glucopyranose, 1,2,3,4,6-penta-O-acetyl-β-D-glucopyranose, 2,3,4,6-tetra-O-acetyl-α-D-glucopyranosyl bromide or 2,3,4,6-tetra-O-acetyl-β-D-glucopyranosyl fluoride in the presence of an activating reagent such as boron trifluoride diethyl ether complex, silver trifluoromethanesulfonate, tin(IV) chloride or trimethyl-silyl trifluoromethanesulfonate in an inert solvent. As the solvent used, dichloromethane, toluene, acetonitrile, nitromethane, ethyl acetate, diethyl ether, chloroform, a mixed solvent thereof and the like can be illustrated. The reaction temperature is usually from −30° C. to reflux temperature, and the reaction time is usually from 10 minutes to 1 day, varying based on a used starting material, solvent and reaction temperature.

Among compounds represented by the above general formula (XI), a compound wherein $R^4$ is a protected mono(lower alkyl)-substituted amino group can also be prepared by subjecting the corresponding compound wherein $R^4$ is a protected amino group obtained by the above process 5 to reaction with a proper agent introducing a lower alkyl group such as a lower alkyl halide, mesylic acid ester, tosylic acid ester and the like in the presence of an alkaline material such as sodium hydride, potassium carbonate or the like in a solvent such as tetrahydrofuran, N,N-dimethylformamide, dimethyl sulfoxide, a mixed solvent thereof or the like.

Process 6

A compound represented by the above general formula (III) can be prepared by subjecting a glucoside represented by the above general formula (XI) to alkaline hydrolysis to remove the acetyl groups. As the solvent used, water, methanol, ethanol, tetrahydrofuran, a mixed solvent thereof and the like can be illustrated, and as alkaline materials, sodium hydroxide, sodium methoxide, sodium ethoxide or the like can be used. The treatment temperature is usually from 0° C. to reflux temperature, and the treatment time is usually from 30 minutes to 6 hours, varying based on a used starting material, solvent and treatment temperature. In the case that $R^4$ or/and $R^5$ has a hydroxy- or amino-protective group, such treatment of the above process can be carried out by suitably changing in conventional means depending on a used protective group as occasion demands, or can be followed by another procedure to remove the protective group in conventional means to prepare a desired compound represented by the above general formula (III).

In the aforementioned production process, the term "hydroxy-protective group" means a hydroxy-protective group used in general organic reactions such as a benzyl group, a methoxymethyl group, an acetyl group, tert-butylmethylsilyl group, tert-butyldiphenylsilyl group and the like, and the term "amino-protective group" means an amino-protective group used in general organic reactions such as a benzyloxycarbonyl group, a tert-butoxycarbonyl group, a phthaloyl group, a benzyl group, an acetyl group and the like.

A compound represented by the above general formula (IX) which was used in the aforementioned production process can be prepared according to the following procedure:

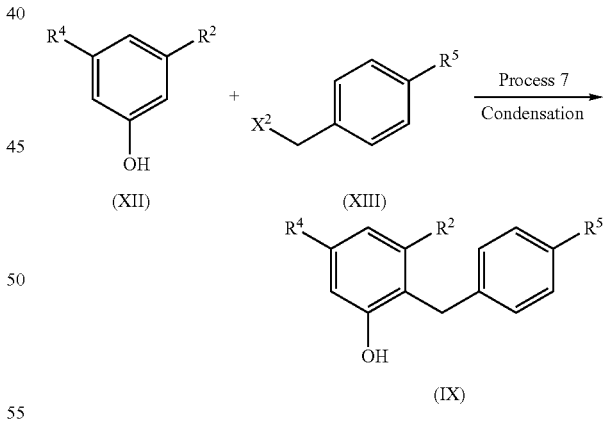

wherein $X^2$ represents a leaving group such as a chlorine atom or the like; and $R^2$, $R^4$ and $R^5$ have the same meanings as defined above.

Process 7

A compound represented by the above general formula (IX) can be prepared by subjecting a phenol derivative represented the above general formula (XII) to benzylation using a benzyl derivative represented by the above formula (XIII) in the presence of an alkaline material such as lithium hydroxide or the like without any solvent. The reaction temperature is usually from 50° C. to 200° C., and the reaction time is usually from 30 minutes to 1 day, varying based on a used starting material, solvent and reaction temperature.

Of compounds represented by the above general formula (III), a compound represented by the following general formula (IIIa), for example, can be prepared using a carboxylic acid derivative represented by the following general formula (XIV) according to the following procedure;

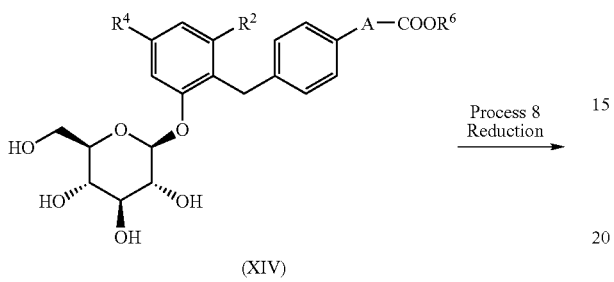

(XIV)

Process 8
Reduction
→

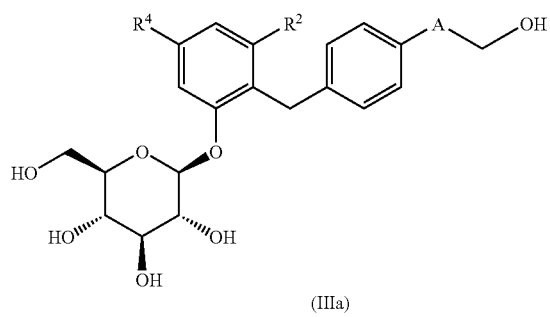

(IIIa)

wherein A represents a straight-chained or branched alkyl group having 1 to 5 carbon atoms or a straight-chained or branched alkenyl group having 2 to 5 carbon atoms; $R^6$ represents a hydrogen atom or a lower alkyl group; and $R^2$ and $R^4$ have the same meanings as defined above.

Process 8

A compound represented by the above general formula (IIIa) can be prepared by subjecting a carboxylic acid derivative represented by the above general formula (XIV) to reduction using a reducing agent such lithium aluminum hydride, borane, lithium borohydride or the like in a solvent such as tetrahydrofuran, diethyl ether, methanol, ethanol, a mixed solvent thereof or the like. The reaction temperature is usually from 0° C. to reflux temperature, and the reaction time is usually from 30 minutes to 1 day, varying based on a used starting material, solvent and reaction temperature.

Of compounds represented by the above general formula (III), a compound represented by the following general formula (IIIb), for example, can be prepared using a phenol derivative represented by the following general formula (IIIc) according to the following procedure;

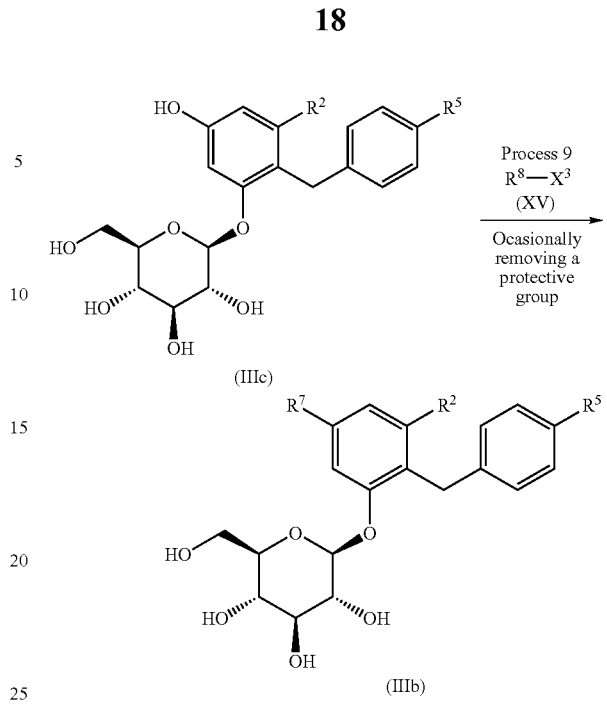

wherein $R^7$ represents a lower alkoxyl group, a lower alkoxy-substituted (lower alkoxy) group, a lower alkoxycarbonyl-substituted (lower alkoxy) group, a carboxy (lower alkoxy) group or a group represented by the general formula: $P^{31}$—O—$A^{21}$— wherein $P^{31}$ represents a hydrogen atom or a hydroxy-protective group; and $A^{11}$ represents a lower alkyleneoxy group; $R^8$ represents a lower alkyl group, a lower alkoxy-substituted (lower alkyl) group, a lower alkoxycarbonyl-substituted (lower alkyl) group, or a group represented by the general formula: $P^{31}$—O—$A^{31}$— wherein $P^{31}$ represents a hydrogen atom or a hydroxy-protective group; and $A^{31}$ represents a lower alkylene group; $X^3$ represents a leaving group such as a chlorine atom, a bromine atom, an iodine atom, a mesyloxy group, a tosyloxy group or the like; and $R^2$ and $R^5$ have the same meanings as defined above.

Process 9

A compound represented by the above general formula (IIIb) can be prepared by subjecting a phenol derivative represented by the above general formula (IIIc) to O-alkylation using an alkylating agent represented by the above general formula (XV) in the presence of an alkaline material such as sodium hydride, potassium carbonate, cesium carbonate, potassium tert-butoxide, sodium hydroxide, potassium hydroxide, sodium hydrogen carbonate or the like in a solvent such as tetrahydrofuran, N,N-dimethylformamide, dimethyl sulfoxide, acetonitrile, a mixed solvent thereof or the like, and followed by deprotection in an usual way as occasional demands. The reaction temperature is usually from 0° C. to reflux temperature, and the reaction time is usually from 30 minutes to 1 day, varying based on a used starting material, solvent and reaction temperature.

The compounds of the present invention obtained by the above production processes can be isolated and purified by conventional separation means such as fractional recrystallization, purification using chromatography, solvent extraction and solid phase extraction.

The glucopyranosyloxybenzylbenzene derivatives represented by the above general formula (I) of the present invention can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, adipic acid, citric acid, fumaric acid, maleic acid, oleic acid, lactic acid, stearic acid, succinic acid, tartaric acid, propionic acid, butyric acid, oxalic acid, malonic acid, malic acid, carbonic acid, glutamic acid, aspartic acid, methanesulfonic acid, benzenesulfonic acid, p-toluenesulfonic acid and the like, salts with organic amines such as 2-aminoethanol, piperidine, morpholine, pyrrolidine and the like, and salts with inorganic bases such as a sodium salt, a potassium salt, a calcium salt, a magnesium salt and the like.

The compounds represented by the above general formula (I) of the present invention include their solvates with pharmaceutically acceptable solvents such as ethanol and water.

Of the compounds represented by the above general formula (I) of the present invention, there are two geometrical isomers in each compound having an unsaturated bond. In the present invention, either of cis(Z)-isomer or trans(E)-isomer can be employed.

Of the compounds represented by the above general formula (I) of the present invention, there are two optical isomers, R-isomer and S-isomer, in each compound having an asymmetric carbon atom excluding the glucopyranosyloxy moiety. In the present invention, either of R-isomer or S-isomer can be employed, and a mixture of both isomers can be also employed.

The prodrugs represented by the above general formula (I) of the present invention are converted into glucopyranosyloxybenzylbenzene derivatives represented by the above general formula (II) as their active forms in vivo, and show an excellent inhibitory activity in human SGLT2. In addition, the prodrugs represented by the above general formula (I) of the present invention have an improved oral absorption, and pharmaceutical compositions comprising as an active ingredient the prodrug or the pharmaceutically acceptable salt thereof have a highly usefulness as oral formulations. Therefore, the prodrugs of the present invention are extremely useful as drugs for the prevention or treatment of a disease associated with hyperglycemia such as diabetes, diabetic complications (e.g., retinopathy, neuropathy, nephropathy, ulcer, macroangiopathy), obesity, hyperinsulinemia, glucose metabolism disorder, hyperlipidemia, hypercholesterolemia, hypertriglyceridemia, lipid metabolism disorder, atherosclerosis, hypertension, congestive heart failure, edema, hyperuricemia, gout or the like.

Furthermore, the compounds of the present invention can be also suitably used in combination with at least one member selected from drugs other than SGLT2 inhibitors. Examples of the drugs which can be used in combination with the compounds of the present invention include an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhidantoin, EGB-761, bimoclomol, sulodexide, Y-128, a hydroxymethylglutaryl coenzyme A reductase inhibitor, a fibric acid derivative, a β3-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyltransferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an α2-adrenoceptor agonist, an antiplatelets agent, a uric acid synthesis inhibitor, a uricosuric agent and a urinary alkalinizer.

In case of uses of the compound of the present invention in combination with the above one or more drugs, the present invention includes either dosage forms of simultaneous administration as a single preparation or separated preparations in way of same or different administration route, and administration at different dosage intervals as separated preparations in way of same or different administration route. A pharmaceutical combination comprising the compound of the present invention and the above one or more drugs includes both dosage forms as a single preparation and separated preparations for combination as mentioned above.

The compounds of the present invention can obtain more advantageous effects than additive effects in the prevention or treatment of the above diseases when using suitably in combination with the above one or more drugs. Also, the administration dose can be decreased in comparison with administration of either drug alone, or adverse effects of coadministrated drugs other than SGLT2 inhibitors can be avoided or declined.

Concrete compounds as the above drugs used for combination and preferable diseases to be treated are exemplified as follows. However, the present invention is not limited thereto, and for example, the concrete compounds include their free compounds, and their or other pharmaceutically acceptable salts.

As insulin sensitivity enhancers, peroxisome proliferator-activated receptor-γ agonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-α agonists such as GW-9578 and BM-170744, peroxisome proliferator-activated receptor-α/γ agonists such as GW-409544, KRP-297, N,N-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, N,N-2344, BM-13125, BM-501050, HQL-975, CLX- 0900, MBX-668, MBX-675, S-15261, GW-544, AZ-242, LY-510929, AR-H049020 and GW-501516 are illustrated. Insulin sensitivity enhancers are used preferably for diabetes, diabetic complications, obesity, hyperinsulinemia, glucose metabolism disorder, hyperlipidemia, hypercholesterolemia, hypertriglyceridemia, lipid metabolism disorder or atherosclerosis, and more preferably for diabetes, hyperinsulinemia or glucose metabolism disorder because of improving the disturbance of insulin signal transduction in peripheral tissues and enhancing glucose uptake into the tissues from the blood, leading to lowering blood glucose level.

As glucose absorption inhibitors, α-glucosidase inhibitors such as acarbose, voglibose, miglitol, CKD-711, emiglitate, MDL-25,637, camiglibose and MDL-73,945, and α-amylase inhibitors such as AZM-127 are illustrated. Glucose absorption inhibitors are used preferably for diabetes, diabetic complications, obesity, hyperinsulinemia or glucose metabolism disorder, and more preferably for diabetes or glucose metabolism disorder because of inhibiting the gastrointestinal enzymatic digestion of carbohydrates contained in foods, and inhibiting or delaying the absorption of glucose into the body.

As biguanides, phenformin, buformin hydrochloride, metformin hydrochloride and the like are illustrated. Biguanides are used preferably for diabetes, diabetic complications, hyperinsulinemia or glucose metabolism disorder, and more preferably for diabetes, hyperinsulinemia or glucose metabolism disorder because of lowering blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlor-propamide, tolazamide, acetohexamide, glyclopyramide, glyburide (glibenclamide), gliclazide, 1-butyl-3-metanilyl-urea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide and the like are illustrated. Insulin secretion enhancers are used preferably for diabetes, diabetic complications or glucose metabolism disorder, and more preferably for diabetes or glucose metabolism disorder because of lowering blood glucose level by acting on pancreatic β-cells and enhancing the insulin secretion.

As insulin preparations, human insulin, human insulin analogues, animal-deprived insulin and the like are illustrated. Insulin preparations are used preferably for diabetes, diabetic complications or glucose metabolism disorder, and more preferably for diabetes or glucose metabolism disorder.

As glucagon receptor antagonists, BAY-27-9955, NNC-92-1687 and the like are illustrated; as insulin receptor kinase stimulants, TER-17411, L-783281, KRX-613 and the like are illustrated; as tripeptidyl peptidase II inhibitors, UCL-1397 and the like are illustrated; as dipeptidyl peptidase IV inhibitors, NVP-DPP728A, TSL-225, P-32/98 and the like are illustrated; as protein tyrosine phosphatase 1B inhibitors, PTP-112, OC-86839, PNU-177496 and the like are illustrated; as glycogen phosphorylase inhibitors, N,N-4201, CP-368296 and the like are illustrated; as fructose-bisphosphatase inhibitors, R-132917 and the like are illustrated; as pyruvate dehydrogenase inhibitors, AZD-7545 and the like are illustrated; as hepatic gluconeogenesis inhibitors, FR-225659 and the like are illustrated; as glucagon-like peptide-1 analogues, exendin-4, CJC-1131 and the like are illustrated; as glucagon-like peptide 1 agonists; AZM-134, LY-315902 and the like are illustrated; and as amylin, amylin analogues or amylin agonists, pramlintide acetate and the like are illustrated. These drugs, glucose-6-phosphatase inhibitors, D-chiroinsitol, glycogen synthase kinase-3 inhibitors, and glucagon-like peptide-1 are used preferably for diabetes, diabetic complications, hyperinsulinemia or glucose metabolism disorder, and more preferably for diabetes or glucose metabolism disorder.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat and the like are illustrated. Aldose reductase inhibitors are preferably used for diabetic complications because of inhibiting aldose reductase and lowering excessive intracellular accumulation of sorbitol in accelerated polyol pathway which are in continuous hyperglycemic condition in the tissues in diabetic complications.

As advanced glycation endproducts formation inhibitors, pyridoxamine, OPB-9195, ALT-946, ALT-711, pimagedine hydrochloride and the like are illustrated. Advanced glycation endproducts formation inhibitors are preferably used for diabetic complications because of inhibiting formation of advanced glycation endproducts which are accelerated in continuous hyperglycemic condition in diabetes and declining of cellular damage.

As protein kinase C inhibitors, LY-333531, midostaurin and the like are illustrated. Protein kinase C inhibitors are preferably used for diabetic complications because of inhibiting protein kinase C activity which is accelerated in continuous hyperglycemic condition in diabetes.

As γ-aminobutyric acid receptor antagonists, topiramate and the like are illustrated; as sodium channel antagonists, mexiletine hydrochloride, oxcarbazepine and the like are illustrated; as transcrit factor NF-κB inhibitors, dexlipotam and the like are illustrated; as lipid peroxidase inhibitors, tirilazad mesylate and the like are illustrated; as N-acetylated-α-linked-acid-dipeptidase inhibitors, GPI-5693 and the like are illustrated; and as carnitine derivatives, carnitine, levacecamine hydrochloride, levocarnitine chloride, levocarnitine, ST-261 and the like are illustrated. These drugs, insulin-like growth factor-I, platelet-derived growth factor, platelet derived growth factor analogues, epidermal growth factor, nerve growth factor, uridine, 5-hydroxy-1-methylhidantoin, EGB-761, bimoclomol, sulodexide and Y-128 are preferably used for diabetic complications.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin and the like are illustrated. Hydroxymethylglutaryl coenzyme A reductase inhibitors are used preferably for hyperlipidemia, hypercholesterolemia, hypertriglyceridemia, lipid metabolism disorder or atherosclerosis, and more preferably for hyperlipidemia, hypercholesterolemia or atherosclerosis because of lowering blood cholesterol level by inhibiting hydroxymethylglutaryl coenzyme A reductase.

As fibric acid derivatives, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 and the like are illustrated. Fibric acid derivatives are used preferably for hyperinsulinemia, hyperlipidemia, hypercholesterolemia, hypertriglyceridemia, lipid metabolism disorder or atherosclerosis, and more preferably for hyperlipidemia, hypertriglyceridemia or atherosclerosis because of activating hepatic lipoprotein lipase and enhancing fatty acid oxidation, leading to lowering blood triglyceride level.

As $\beta_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 and the like are illustrated. $\beta_3$-Adrenoceptor agonists are used preferably for obesity, hyperinsulinemia, hyperlipidemia, hypercholesterolemia, hypertriglyceridemia or lipid metabolism disorder, and more preferably for obesity or hyperinsulinemia because of stimulating $\beta_3$-adrenoceptor in adipose tissue and enhancing the fatty acid oxidation, leading to induction of energy expenditure.

As acyl-coenzyme A cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe and the like are illustrated. Acyl-coenzyme A cholesterol acyltransferase inhibitors are used preferably for hyperlipidemia, hyper-cholesterolemia, hypertriglyceridemia or lipid metabolism disorder, and more preferably for hyperlipidemia or hyper-cholesterolemia because of lowering blood cholesterol level by inhibiting acyl-coenzyme A cholesterol acyltransferase.

As thyroid hormone receptor agonists, sodium liothyronine, sodium levothyroxine, KB-2611 and the like are illustrated; as cholesterol absorption inhibitors, ezetimibe, SCH-48461 and the like are illustrated; as lipase inhibitors, orlistat, ATL-962, AZM-131, RED-103004 and the like are illustrated; as carnitine palmitoyltransferase inhibitors, etomoxir and the like are illustrated; as squalene synthase inhibitors, SDZ-268-198, BMS-188494, A-87049, RPR-101821, ZD-9720, RPR-107393, ER-27856 and the like are illustrated; as nicotinic acid derivatives, nicotinic acid, nicotinamide, nicomol, niceritrol, acipimox, nicorandil and the like are illustrated; as bile acid sequestrants, colestyramine, colestilan, colesevelam hydrochloride, GT-102-279 and the like are illustrated; as sodium/bile acid cotransporter inhibitors, 264W94, S-8921, SD-5613 and the like are illustrated; and as cholesterol ester transfer protein inhibitors, PNU-107368E, SC-795, JTT-705, CP-529414 and the like are illustrated. These drugs, probcol, microsomal trigylceride transfer protein inhibitors, lipoxygenase inhibitors and low-density lipoprotein receptor enhancers are preferably used for hyperlipidemia, hypercholesterolemia, hypertriglyceridemia or lipid metabolism disorder.

As appetite suppressants, monoamine reuptake inhibitors, serotonin reuptake inhibitors, serotonin releasing stimulants, serotonin agonists (especially 5HT$_{2C}$-agonists), noradrenaline reuptake inhibitors, noradrenaline releasing stimulants, $\alpha_1$-adrenoceptor agonists, $\beta_2$-adrenoceptor agonists, dopamine agonists, cannabinoid receptor antagonists, $\gamma$-aminobutyric acid receptor antagonists, H$_3$-histamine antagonists, L-histidine, leptin, leptin analogues, leptin receptor agonists, melanocortin receptor agonists (especially, MC3-R agonists, MC4-R agonists), $\alpha$-melanocyte stimulating hormone, cocaine- and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotrophin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone antagonists, agouti-related protein inhibitors and orexin receptor antagonists are illustrated. Concretely, as monoamine reuptake inhibitors, mazindol and the like are illustrated; as serotonin reuptake inhibitors, dexfenfluramine hydrochloride, fenfluramine, sibutramine hydrochloride, fluvoxamine maleate, sertraline hydrochloride and the like are illustrated; as serotonin agonists, inotriptan, (+)-norfenfluramine and the like are illustrated; as noradrenaline reuptake inhibitors, bupropion, GW-320659 and the like are illustrated; as noradrenaline releasing stimulants, rolipram, YM-992 and the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex and the like are illustrated; as dopamine agonists, ER-230, doprexin, bromocriptine mesylate and the like are illustrated; as cannabinoid receptor antagonists, rimonabant and the like are illustrated; as $\gamma$-aminobutyric acid receptor antagonists, topiramate and the like are illustrated; as H$_3$-histamine antagonists, GT-2394 and the like are illustrated; as leptin, leptin analogues or leptin receptor agonists, LY-355101 and the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 and the like are illustrated; and as neuropeptide Y antagonists, SR-120819-A, PD-160170, NGD-95-1, BIBP-3226, 1229-U-91, CGP-71683, BIBO-3304, CP-671906-01, J-115814 and the like are illustrated. Appetite suppressants are used preferably for diabetes, diabetic complications, obesity, glucose metabolism disorder, hyperlipidemia, hypercholesterolemia, hypertriglyceridemia, lipid metabolism disorder, atherosclerosis, hypertension, congestive heart failure, edema, hyperuricemia or gout, and more preferably for obesity because of stimulating or inhibiting the activities of intracerebral monoamines or bioactive peptides in central appetite regulatory system and suppressing the appetite, leading to reduction of energy intake.

As angiotensin-converting enzyme inhibitors, captopril, enalapri maleate, alacepril, delapril hydrochloride, ramipril, lisinopril, imidapril hydrochloride, benazeprilhydrochloride, ceronapril monohydrate, cilazapril, sodium fosinopril, perindopril erbumine, calcium moveltipril, quinapril hydro-chloride, spirapril hydrochloride, temocapril hydrochloride, trandolapril, calcium zofenopril, moexipril hydrochloride, rentiapril and the like are illustrated. Angiotensin-converting enzyme inhibitors are preferably used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril and the like are illustrated. Neutral endopeptidase inhibitors are preferably used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 and the like are illustrated. Angiotensin II receptor antagonists are preferably used for diabetic complications or hypertension.

As endothelin-converting enzyme inhibitors, CGS-31447, CGS-35066, SM-19712 and the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 and the like are illustrated. These drugs are preferably used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-α, PNU-80873A, isosorbide, D-mannitol, D-sorbitol, fructose, glycerin, acetazolamide, methazolamide, FR-179544, OPC-31260, lixivaptan, conivaptan hydrochloride and the like are illustrated. Diuretic agents are preferably used for diabetic complications, hypertension, congestive heart failure or edema, and more preferably for hypertension, congestive heart failure or edema because of reducing blood pressure or improving edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride and the like are illustrated; as vasodilating antihypertensive agents, indapamide, todralazine hydrochloride, hydralazine hydrochloride, cadralazine, budralazine and the like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin and the like are illustrated; as centrally acting antihypertensive agents, reserpine and the like are illustrated; and as α₂-adrenoceptor agonists, clonidine hydrochloride, methyldopa, CHF-1035, guanabenz acetate, guanfacine hydrochloride, moxonidine, lofexidine, talipexole hydrochloride and the like are illustrated. These drugs are preferably used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin and the like are illustrated. Antiplatelets agents are preferably used for atherosclerosis or congestive heart failure.

As uric acid synthesis inhibitors, allopurinol, oxypurinol and the like are illustrated; as uricosuric agents, benzbromarone, probenecid and the like are illustrated; and as urinary alkalinizers, sodium hydrogen carbonate, potassium citrate, sodium citrate and the like are illustrated. These drugs are preferably used for hyperuricemia or gout.

In case of use in combination with drugs other than SGLT2 inhibitors, for example, in the use for diabetes, the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant is preferable; the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue and an amylin agonist is more preferable; and the combination with at least one member of the group consisting of an insulin sensitivity enhancer, a glucose absorption inhibitor, a biguanide, an insulin secretion enhancer and an insulin preparation is most preferable. Similarly, in the use for diabetic complications, the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6 phosphatase inhibitor, a fructose-bisphosphatase inhibitor, a pyruvate dehydrogenase inhibitor, a hepatic gluconeogenesis inhibitor, D-chiroinsitol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhidantoin, EGB-761, bimoclomol, sulodexide, Y-128, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the combination with at least one member of the group consisting of an aldose reductase inhibitor, an angiotensin-converting enzyme inhibitor, a neutral endopeptidase inhibitor and an angiotensin II receptor antagonist is more preferable. Furthermore, in the use for obesity, the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant is preferable; and the combination with at least one member of the group consisting of a $\beta_3$-adrenoceptor agonist and an appetite suppressant is more preferable.

When the pharmaceutical compositions of the present invention are employed in the practical treatment, various dosage forms are used depending on their uses. As examples of the dosage forms, powders, granules, fine granules, dry syrups, tablets, capsules, injections, solutions, ointments, suppositories, poultices and the like are illustrated, which are orally or parenterally administered.

These pharmaceutical compositions can be prepared by admixing with or by diluting and dissolving an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with pharmaceutically conventional methods depending on their dosage forms. In case of the use of the compound of the present invention in combination with the drugs other than SGLT2 inhibitors, they can be prepared by formulating each active ingredient together or individually.

When the pharmaceutical compositions of the present invention are employed in the practical treatment, the dosage of a compound represented by the above general formula (I) or a pharmaceutically acceptable salt thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably. Also, in case of the use of the compound of the present invention in combination with the drugs other than SGLT2 inhibitors, the dosage of the compound of the present invention can be decreased depending on the dosage of the drugs other than SGLT2 inhibitors.

The present invention is further illustrated in more detail by way of the following Reference Examples, Examples and Test Examples. However, the present invention is not limited thereto.

REFERENCE EXAMPLE 1

4-(3-Benzyloxypropyl)bromobenzene

A suspension of sodium hydride (60%, 0.97 g), 3-(4-bromophenyl)-1-propanol (1.0 g) and benzyl bromide (0.69 mL) in benzene (24 mL) was stirred under reflux for 7 hours. After cooling to room temperature, a saturated aqueous ammonium chloride solution (50 mL) was added to the reaction mixture, and the mixture was extracted with ethyl acetate (100 mL). The organic layer was washed with water (40 mL) and brine (40 mL) and dried over anhydrous sodium sulfate. The solvent was removed under reduced pressure, and the residue was purified by column chromatography on silica gel (eluent: hexane/ethyl acetate=20/1) to give 4-(3-benzyloxypropyl)bromobenzene (1.4 g).

$^1$H-NMR (CDCl$_3$) $\delta$ ppm:
1.85-2.00 (2H, m), 2.60-2.75 (2H, m), 3.47 (2H, t, J=6.2 Hz), 4.50 (2H, s), 7.00-7.10 (2H, m), 7.20-7.45 (7H, m)

REFERENCE EXAMPLE 2

Methyl 4-(4-ethylbenzyl)-3-hydroxybenzoate

To a solution of 1-bromo-4-ethylbenzene (0.41 mL) in tetrahydrofuran (15 mL) was added 1.45 mol/L tert-buthyllithium n-pentane solution (2.3 mL) under an argon atmosphere at −78° C. After the mixture was stirred at −78° C. for 10 minutes, a solution of methyl 4-formyl-3-hydroxybenzoate (0.18 g) in tetrahydrofuran (5 mL) was added to the reaction mixture. After the mixture was stirred under ice-cooling for 45 minutes, a saturated aqueous ammonium chloride solution and water were added to the reaction mixture, and the mixture was extracted with ethyl acetate. The extract was washed with water and dried over anhydrous magnesium sulfate, and the solvent was removed under reduced pressure. The residue was purified by column chromatography on silica gel (eluent: hexane/ethyl acetate=3/1) to give a diphenylmethanol compound (0.27 g). The obtained diphenylmethanol compound (0.27 g) was dissolved in methanol (5 mL), and concentrated hydrochloric acid (0.08 mL) and 10% palladium-carbon powder (54 mg) were added to the solution. After the mixture was stirred under a hydrogen atmosphere at room temperature for 18 hours, the catalyst was removed by filtration, and the filtrate was concentrated under reduced pressure. The residue was purified by column chromatography on silica gel (eluent: hexane/ethyl acetate=3/1) to give methyl 4-(4-ethylbenzyl)-3-hydroxybenzoate (0.20 g).

$^1$H-NMR (CDCl$_3$) $\delta$ ppm:
1.22 (3H, t, J=7.6 Hz), 2.62 (2H, q, J=7.6 Hz), 3.89 (3H, s), 4.00 (2H, s), 5.01 (1H, s), 7.05-7.25 (5H, m), 7.47 (1H, d, J=1.6 Hz), 7.56 (1H, dd, J=1.6, 7.8 Hz)

REFERENCE EXAMPLE 3

Methyl 3-hydroxy-4-(4-propoxybenzyl)benzoate

To a solution of 1-allyloxy-4-bromobenzene (3.1 g) in tetrahydrofuran (70 mL) was added 1.45 mol/L tert-buthyllithium n-pentane solution (11 mL) under an argon atmosphere at −78° C. After the mixture was stirred at −78° C. for 5 minutes, a solution of methyl 4-formyl-3-hydroxybenzoate (0.89 g) in tetrahydrofuran (15 mL) was added to the reaction mixture. After the mixture was stirred for 30 minutes under ice-cooling, a saturated aqueous ammonium chloride solution and water were added to the reaction mixture, and the mixture was extracted with ethyl acetate. The extract was washed with water and dried over anhydrous magnesium sulfate, and the solvent was removed under reduced pressure. The residue was purified by column chromatography on silica gel (eluent: hexane/ethyl acetate=3/1) to give a diphenylmethanol compound (0.99 g). The obtained diphenylmethanol compound (0.99 g) was dissolved in methanol (10 mL), and 10% palladium-carbon powder (0.30 g) was added to the solution. After the mixture was stirred under a hydrogen atmosphere at room temperature for 24 hours, the catalyst was removed by filtration, and the filtrate was concentrated under reduced pressure. The residue was purified by column chromatography on silica gel (eluent: hexane/ethyl acetate=3/1) to give methyl 3-hydroxy-4-(4-propoxybenzyl)benzoate (0.50 g).

$^1$H-NMR (CDCl$_3$) δ ppm:
1.02 (3H, t, J=7.4 Hz), 1.70-1.85 (2H, m), 3.80-3.95 (5H, m), 3.97 (2H, s), 4.99 (1H, s), 6.75-6.90 (2H, m), 7.05-7.20 (3H, m), 7.47 (1H, d, J=1.5 Hz), 7.56 (1H, dd, J=1.5, 7.8 Hz)

REFERENCE EXAMPLE 4

Methyl 3-hydroxy-4-[4-(2-hydroxyethyl)benzyl]benzoate

To a solution of 2-(4-bromophenyl)ethylalchol (1.7 g) in tetrahydrofuran (100 mL) was added 1.45 mol/L tert-butyl-lithium n-pentane solution (12.6 mL) under an argon atmosphere at −78° C. After the mixture was stirred at −78° C. for 10 minutes, a solution of methyl 4-formyl-3-hydroxybenzoate (0.50 g) in tetrahydrofuran (10 mL) was added to the reaction mixture. After the reaction mixture was stirred for 30 minutes under ice-cooling, a saturated aqueous ammonium chloride solution and water were added to the reaction mixture, and the mixture was extracted with ethyl acetate. The extract was washed with water and dried over anhydrous magnesium sulfate, and the solvent was removed under reduced pressure. The residue was purified by column chromatography on silica gel (eluent: hexane/ethyl acetate=1/3) to give a diphenylmethanol compound (0.28 g). The obtained diphenylmethanol compound (0.28 g) was dissolved in methanol (5 mL), and 10% palladium-carbon powder (0.14 g) was added to the solution. After the mixture was stirred at room temperature for 14 hours under a hydrogen atmosphere, the catalyst was removed by filtration, and the filtrate was concentrated under reduced pressure. The residue was purified by column chromatography on silica gel (eluent: hexane/ethylacetate=1/1) to give methyl 3-hydroxy-4-[4-(2-hydroxyethyl)benzyl]benzoate (0.26 g).

$^1$H-NMR (CDCl$_3$) δ ppm:
1.37 (1H, t, J=5.9 Hz), 2.84 (2H, t, J=6.5 Hz), 3.75-3.95 (5H, m), 4.01 (2H, s), 5.10 (1H, s), 7.05-7.25 (5H, m), 7.47 (1H, d, J=1.6 Hz), 7.56 (1H, dd, J=1.6, 7.8 Hz)

REFERENCE EXAMPLE 5

2-[4-(3-Benzoyloxypropyl)benzyl]phenol

A Grignard reagent was prepared from 4-(3-benzyloxypropyl)bromobenzene (3.2 g), magnesium (0.25 g), a catalytic amount of iodine and tetrahydrofuran (10.5 mL). To the obtained Grignard reagent solution was added a solution of 2-(methoxymethoxy)benzaldehyde (1.1 g) in tetrahydrofuran (24 mL), and the mixture was stirred at 65° C. for 25 minutes. After cooling to room temperature, a saturated aqueous ammonium chloride solution (10 mL) and water (20 mL) were added to the reaction mixture, and the mixture was extracted with ethyl acetate (100 mL). The extract was washed with water (20 mL) and brine (20 mL). After the extract was dried over anhydrous sodium sulfate, the solvent was removed under reduced pressure, and the residue was purified by column chromatography on silica gel (eluent: hexane/ethyl acetate=5/1) to give a diphenylmethanol compound (2.5 g). The obtained diphenylmethanol compound (2.5 g) was dissolved in ethanol (42 mL), a catalytic amount of 10% palladium-carbon powder was added to the solution, and the mixture was stirred under a hydrogen atmosphere at room temperature for 7.5 hours. The catalyst was removed by filtration, and the filtrate was concentrated under reduced pressure. The residue was purified by column chromatography on silica gel (eluent: hexane/ethyl acetate=5/2) to give a phenylpropanol compound (1.6 g). After the obtained phenylpropanol compound (1.6 g) was dissolved in dichloromethane (29 mL), 4-(dimethylamino)pyridine (0.069 g), triethylamine (1.0 mL) and benzoyl chloride (0.79 mL) were added to the solution, and the mixture was stirred at room temperature for 3 hours. To the reaction mixture were added ethyl acetate (100 mL) and water (30 mL), and the organic layer was separated. The extract was washed with brine (30 mL) and dried over anhydrous sodium sulfate, and the solvent was removed under reduced pressure. The residue was purified by column chromatography on silica gel (eluent: hexane/ethyl acetate=20/1) to give an ester compound (2.2 g). A mixture of the obtained ester compound (2.2 g), p-toluenesulfonic acid monohydrate (0.21 g) and methanol (28 mL) was stirred at room temperature for 24 hours. The reaction mixture was concentrated under reduced pressure, and the residue was purified by column chromatography on silica gel (eluent: hexane/ethyl acetate=5/1) to give 2-[4-(3-benzoyloxypropyl)benzyl]phenol (1.8 g).

$^1$H-NMR (CDCl$_3$) δ ppm:
2.00-2.15 (2H, m), 2.70-2.80 (2H, m), 3.96 (2H, s), 4.33 (2H, t, J=6.5 Hz), 4.74 (1H, brs), 6.75-6.85 (1H, m), 6.85-6.95 (1H, m), 7.05-7.20 (6H, m), 7.35-7.50 (2H, m), 7.50-7.65 (1H, m), 8.00-8.10 (2H, m)

REFERENCE EXAMPLE 6

2-[4-(2-Benzoyloxyethyl)benzyl]phenol

The title compound was prepared in a similar manner to that described in Reference Example 5 using 4-(2-benzyloxyethyl)bromobenzene instead of 4-(3-benzyloxypropyl)-bromobenzene.

$^1$H-NMR (CDCl$_3$) δ ppm:
3.04 (2H, t, J=7.1 Hz), 3.98 (2H, s), 4.51 (2H, t, J=7.1 Hz), 4.66 (1H, s), 6.75-6.85 (1H, m), 6.85-6.95 (1H, m), 7.05-7.25 (6H, m), 7.35-7.50 (2H, m), 7.50-7.60 (1H., m), 7.95-8.05 (2H, m)

REFERENCE EXAMPLE 7

5-Acetoxymethyl-2-(4-ethylbenzyl)phenol

To a suspension of lithium aluminum hydride (95 mg) in diethyl ether (10 mL) was added a solution of methyl 4-(4-ethylbenzyl)-3-hydroxybenzoate (0.27 g) in diethyl ether (5 mL) under ice-cooling. After the mixture was heated under reflux for 45 minutes, water (0.1 mL), 15% aqueous sodium hydroxide solution (0.1 mL) and water (0.3 mL) were added successively to the reaction mixture under ice-cooling. After the mixture was stirred at room temperature for 5 minutes, the reaction mixture was poured into 0.5 mol/L hydrochloric acid, and the resulting mixture was extracted with ethyl acetate. The extract was dried over anhydrous magnesium sulfate, and the solvent was removed under reduced pressure. The residue was purified by column chromatography on silica gel (eluent: hexane/ethyl acetate=1/1) to give a reduced compound (0.22 g). After the obtained reduced compound (0.22 g) was dissolved in tetrahydrofuran (2 mL), vinyl acetate (2 mL) and bis(dibutylchlorotin)oxide (24 mg) were added to the solution, and the mixture was stirred at 30° C. for 19 hours. The reaction mixture was purified directly by column chromatography on silica gel (eluent: hexane/ethyl acetate=3/1) to give 5-acetoxymethyl-2-(4-ethylbenzyl)phenol (0.21 g)

$^1$H-NMR (CDCl$_3$) δ ppm: .

1.21 (3H, t, J=7.6 Hz), 2.09 (3H, s), 2.61 (2H, q, J=7.6 Hz), 3.95 (2H, s), 4.74 (1H, s), 5.03 (2H, s), 6.80 (1H, d, J=1.3 Hz), 6.80-6.90 (1H, m), 7.05-7.20 (5H, m)

REFERENCE EXAMPLE 8

5-Acetoxymethyl-2-(4-propoxybenzyl)phenol

The title compound was prepared in a similar manner to that described in Reference Example 7 using methyl 3-hydroxy-4-(4-propoxybenzyl)benzoate instead of methyl 4-(4-ethylbenzyl)-3-hydroxybenzoate.

$^1$H-NMR (CDCl$_3$) δ ppm:
1.02 (3H, t, J=7.4 Hz), 1.70-1.85 (2H, m), 2.09 (3H, s), 3.88 (2H, t, J=6.6 Hz), 3.91 (2H, s), 5.02 (2H, s), 5.28 (1H, s), 6.70-6.90 (4H, m), 7.00-7.20 (3H, m)

REFERENCE EXAMPLE 9

2-[4-(2-Acetoxyethyl)benzyl]-5-acetoxymethylphenol

The title compound was prepared in a similar manner to that described in Reference Example 7 using methyl 3-hydroxy-4-[4-(2-hydroxyethyl)benzyl]benzoate instead of methyl 4-(4-ethylbenzyl)-3-hydroxybenzoate.

$^1$H-NMR (CDCl$_3$) δ ppm:
2.03 (3H, s), 2.09 (3H, s), 2.90 (2H, t, J=7.1 Hz), 3.96 (2H, s), 4.25 (2H, t, J=7.1 Hz), 4.82 (1H, s), 5.03 (2H, s), 6.80 (1H, d, J=1.5 Hz), 6.87 (1H, dd, J=1.5, 7.7 Hz), 7.05-7.20 (5H, m)

REFERENCE EXAMPLE 10

5-Acetoxymethyl-2-(4-ethylbenzyl)phenyl 2,3,4,6-tetra-O-acetyl-β-D-glucopyranoside To a solution of 5-acetoxymethyl-2-(4-ethylbenzyl)phenol (0.59 g) and 2,3,4,6-tetra-O-acetyl-1-O-trichloroacetoimidoyl-α-D-glucopyranose (1.1 g) in dichloromethane (15 mL) was added boron trifluoride diethyl ether complex (0.31 mL), and the mixture was stirred at 0° C. for 30 minutes. The reaction mixture was purified by column chromatography on silica gel (eluent: hexane/ethyl acetate=2/1-3/2) to give 5-acetoxymethyl-2-(4-ethylbenzyl)phenyl 2,3,4,6-tetra-O-acetyl-β-D-glucopyranoside (1.0 g).

$^1$H-NMR (CDCl$_3$) δ ppm:
1.20 (3H, t, J=7.6 Hz), 1.88 (3H, s), 2.02 (3H, s), 2.05 (3H, s), 2.07 (3H, s), 2.09 (3H, s), 2.60 (2H, q, J=7.6 Hz), 3.80-3.95 (3H, m), 4.20 (1H, dd, J=2.4, 12.3 Hz), 4.27 (1H, dd, J=5.3, 12.3 Hz), 5.00-5.10 (2H, m), 5.13 (1H, d, J=7.4 Hz), 5.15-5.40 (3H, m), 6.95-7.15 (7H, m)

REFERENCE EXAMPLE 11

5-Acetoxymethyl-2-(4-propoxybenzyl)phenyl 2,3,4,6-tetra-O-acetyl-β-D-glucopyranoside The title compound was prepared in a similar manner to that described in Reference Example 10 using 5-acetoxymethyl-2-(4-propoxybenzyl)phenol instead of 5-acetoxymethyl-2-(4-ethylbenzyl)phenol.

$^1$H-NMR (CDCl$_3$) δ ppm:
1.01 (3H, t, J=7.4 Hz), 1.70-1.85 (2H, m), 1.92 (3H, s), 2.03 (3H, s), 2.05 (3H, s), 2.07 (3H, s), 2.09 (3H, s), 3.80-3.95 (5H, m), 4.20 (1H, dd, J=2.4, 12.3 Hz), 4.27 (1H, dd, J=5.3, 12.3 Hz), 5.00-5.10 (2H, m), 5.12 (1H, d, J=7.4 Hz), 5.15-5.40 (3H, m), 6.75-6.85 (2H, m), 6.95-7.10 (5H, m)

REFERENCE EXAMPLE 12

2-[4-(2-Acetoxyethyl)benzyl]-5-acetoxymethylphenyl 2,3,4,6-tetra-O-acetyl-β-D-glucopyranoside The title compound was prepared in a similar manner to that described in Reference Example 10 using 2-[4-(2-acetoxyethyl)benzyl]-5-acetoxymethylphenol instead of 5-acetoxymethyl-2-(4-ethylbenzyl)phenol.

$^1$H-NMR (CDCl$_3$) δ ppm:
1.89 (3H, s), 2.03 (3H, s), 2.03 (3H, s), 2.05 (3H, s), 2.07 (3H, s), 2.09 (3H, s), 2.88 (2H, t, J=7.1 Hz), 3.85-3.95 (3H, m), 4.15-4.35 (4H, m), 5.00-5.10 (2H, m), 5.13 (1H, d, J=7.5 Hz), 5.15-5.40 (3H, m), 6.95-7.15 (7H, m)

REFERENCE EXAMPLE 13

2-(4-Ethylbenzyl)-5-hydroxymethylphenyl β-D-glucopyranoside

Sodium methoxide (28% methanol solution; 0.3 mL) was added to a solution of 5-acetoxymethyl-2-(4-ethylbenzyl)phenyl 2,3,4,6-tetra-O-acetyl-β-D-glucopyranoside (1.0 g) in methanol (12 mL), and the mixture was stirred at room temperature for 40 minutes. The solvent was removed under reduced pressure. The residue was purified by column chromatography on silica gel (eluent: dichloromethane/methanol=7/1) to give 2-(4-ethylbenzyl)-5-hydroxymethylphenyl β-D-glucopyranoside (0.68 g).

$^1$H-NMR (CD$_3$OD) δ ppm:
1.19 (3H, t, J=7.6 Hz), 2.57 (2H, q, J=7.6 Hz), 3.30-3.55 (4H, m), 3.65-3.75 (1H, m), 3.85-4.00 (2H, m), 4.04 (1H, d, J=15.0 Hz), 4.54 (2H, s), 4.93 (1H, d, J=7.4 Hz), 6.85-6.95 (1H, m), 7.02 (1H, d, J=7.7 Hz), 7.06 (2H, d, J=8.1 Hz), 7.10-7.20 (3H, m)

REFERENCE EXAMPLE 14

5-Hydroxymethyl-2-(4-propoxybenzyl)phenyl β-D-glucopyranoside

The title compound was prepared in a similar manner to that described in Reference Example 13 using 5-acetoxymethyl-2-(4-propoxybenzyl)phenyl 2,3,4,6-tetra-O-acetyl-β-D-glucopyranoside instead of 5-acetoxymethyl-2-(4-ethylbenzyl)phenyl 2,3,4,6-tetra-O-acetyl-β-D-glucopyranoside.

$^1$H-NMR (CD$_3$OD) δ ppm:
1.02 (3H, t, J=7.4 Hz), 1.70-1.85 (2H, m), 3.30-3.55 (4H, m), 3.65-3.75 (1H, m), 3.80-3.95 (4H, m), 4.00 (1H, d, J=15.0 Hz), 4.54 (2H, s), 4.93 (1H, d, J=7.4 Hz), 6.70-6.85 (2H, m), 6.85-6.95 (1H, m), 7.02 (1H, d, J=7.7 Hz), 7.05-7.20 (3H, m)

REFERENCE EXAMPLE 15

2-[4-(2-Hydroxyethyl)benzyl]-5-hydroxymethylphenyl β-D-glucopyranoside

The title compound was prepared in a similar manner to that described in Reference Example 13 using 2-[4-(2-acetoxyethyl)benzyl]-5-acetoxymethylphenyl 2,3,4,6-tetra-O-acetyl-β-D-glucopyranoside instead of 5-acetoxymethyl-2-(4-ethylbenzyl)phenyl 2,3,4,6-tetra-O-acetyl-β-D-glucopyranoside.

1H-NMR (CD$_3$OD) δ ppm:
2.76 (2H, t, J=7.1 Hz), 3.30-3.55 (4H, m), 3.60-3.75 (3H, m), 3.85-4.00 (2H, m), 4.05 (1H, d, J=14.6 Hz), 4.54 (2H, s), 4.92 (1H, d, J=7.2 Hz), 6.85-6.95 (1H, m), 7.03 (1H, d, J=7.9 Hz), 7.09 (2H, d, J=7.8 Hz), 7.10-7.20 (3H, m)

REFERENCE EXAMPLE 16

2-[4-(2-Hydroxyethyl)benzyl]phenyl β-D-glucopyranoside

To a solution of 2-[4-(2-benzoyloxyethyl)benzyl]phenol (0.49 g) and 1,2,3,4,6-penta-O-acetyl-β-D-glucopyranose (1.7 g) in toluene (5.2 mL) and dichloromethane (2.2 mL) was added boron trifluoride diethyl ether complex (0.56 mL), and the mixture was stirred at 25° C. for 8 hours. To the reaction mixture were added ethyl acetate (70 mL) and a saturated aqueous sodium hydrogen carbonate solution (25 mL), and the organic layer was separated. The organic layer was washed with brine (25 mL) and dried over anhydrous sodium sulfate, and the solvent was removed under reduced pressure. The residue was dissolved in methanol (5 mL) and tetrahydrofuran (2.5 mL), sodium methoxide (28% methanol solution, 0.14 mL) was added to the solution, and the resulting mixture was stirred at 25° C. for 12.5 hours. To the reaction mixture were added ethyl acetate (75 mL) and water (20 mL), and the organic layer was separated. The organic layer was washed with brine (20 mL) and dried over anhydrous sodium sulfate, and the solvent was removed under reduced pressure. The residue was dissolved in methanol (7.5 mL), sodium methoxide (28% methanol solution, 0.085 mL) was added to the solution, and the resulting mixture was stirred at 25° C. for 5 hours. The reaction mixture was purified by column chromatography on silica gel (eluent: dichloromethane/methanol=4/1). The solvent was removed under reduced pressure, diethyl ether was added to the residue, and the resulting precipitates were collected by filtration. The obtained solid was washed with diethyl ether and dried under reduced pressure to give 2-[4-(2-hydroxyethyl)benzyl]phenyl β-D-glucopyranoside (0.47 g).

$^1$H-NMR (CD$_3$OD) δ ppm:
2.76 (2H, t, J=7.1 Hz), 3.35-3.55 (4H, m), 3.65-3.75 (3H, m), 3.88 (1H, dd, J=1.8, 11.8 Hz), 3.95 (1H, d, J=15.2 Hz), 4.07 (1H, d, J=15.2 Hz), 4.90 (1H, d, J=7.4 Hz), 6.85-6.95 (1H, m), 7.00-7.20 (7H, m)

REFERENCE EXAMPLE 17

2-[4-(3-Hydroxypropyl)benzyl]phenyl β-D-glucopyranoside

The title compound was prepared in a similar manner to that described in Reference Example 16 using 2-[4-(3-benzoyloxypropyl)benzyl]phenol instead of 2-[4-(2-benzoyloxyethyl)benzyl]phenol.

$^1$H-NMR (CD$_3$OD) δ ppm:
1.70-1.85 (2H, m), 2.55-2.65 (2H, m), 3.30-3.60 (6H, m), 3.69 (1H, dd, J=5.2, 11.9 Hz), 3.88 (1H, dd, J=2.0, 11.9 Hz), 3.95 (1H, d, J=15.1 Hz), 4.06 (1H, d, J=15.1 Hz), 4.90 (1H, d, J=7.3 Hz), 6.85-6.95 (1H, m), 7.00-7.20 (7H, m)

REFERENCE EXAMPLE 18

Methyl 4-[(2-benzyloxyphenyl)hydroxymethyl]benzoate

A Grignard reagent was prepared from 2-benzyloxybromobenzene (5.3 g), magnesium (0.49 g) and tetrahydrofuran (160 mL). The obtained Grignard reagent was added to a solution of methyl terephthalaldehyate (3.3 g) in tetrahydrofuran (60 mL), and the mixture was stirred at room temperature for 1 hour. To the reaction mixture was added water and dilute hydrochloric acid, and the mixture was extracted with ethylacetate. The organic layer was washed with brine and dried over anhydrous sodium sulfate. The solvent was removed under reduced pressure, and the residue was purified by column chromatography on aminopropyl silica gel (eluent: hexane/ethyl acetate=4/1) to give methyl 4-[(2-benzyloxyphenyl)-hydroxymethyl]benzoate (2.6 g).

$^1$H-NMR (CDCl$_3$) δ ppm:
3.02 (1H, d, J=6.3 Hz), 3.91 (3H, s), 5.00 (1H, d, J=11.6 Hz), 5.04 (1H, d, J=11.6 Hz), 6.07 (1H, d, J=6.3 Hz), 6.90-7.05 (2H, m), 7.15-7.35 (7H, m), 7.35-7.45 (2H, m), 7.90-8.00 (2H, m)

REFERENCE EXAMPLE 19

Methyl 4-(2-hydroxybenzyl)benzoate

To a solution of methyl 4-[(2-benzyloxyphenyl)-hydroxymethyl]benzoate (2.6 g) in ethanol (15 mL) was added 10% palladium-carbon powder (0.50 g), and the mixture was stirred under a hydrogen atmosphere at room temperature for 18 hours. Insoluble material was removed by filtration, and the solvent of the filtrate was removed under reduced pressure to give methyl 4-(2-hydroxybenzyl)benzoate (1.7 g).

$^1$H-NMR (CDCl$_3$) δ ppm:
3.89 (3H, s), 4.04 (2H, s), 4.80 (1H, s), 6.75-6.80 (1H, m), 6.85-6.95 (1H, m), 7.05-7.20 (2H, m), 7.25-7.35 (2H, m), 7.90-8.00 (2H, m)

REFERENCE EXAMPLE 20

Methyl 4-(2-benzyloxybenzyl)benzoate

To a suspension of methyl 4-(2-hydroxybenzyl)benzoate (1.5 g) and potassium carbonate (0.94 g) in N,N-dimethylformamide (200 mL) was added benzyl bromide (0.81 mL), and the mixture was stirred at 50° C. for 5 hours. In soluble material was removed by filtration, and to the filtrate was added water and dilute hydrochloric acid. The mixture was extracted with ethylacetate. The organic layer was washed with brine and dried over anhydrous magnesium sulfate. The solvent was removed under reduced pressure, and the residue was purified by column chromatography on silica gel (eluent: hexane/ethyl acetate=4/1) to give methyl 4-(2-benzyloxybenzyl)benzoate (2.1 g).

$^1$H-NMR (CDCl$_3$) δ ppm:
3.89 (3H, s), 4.06 (2H, s), 5.03 (2H, s), 6.85-6.95 (2H, m), 7.10-7.40 (9H, m), 7.85-7.95 (2H, m)

REFERENCE EXAMPLE 21

4-(2-Benzyloxybenzyl)benzyl Alcohol

To a suspension of lithium aluminum hydride (0.47 g) in tetrahydrofuran (5 mL) was added dropwise a solution of methyl 4-(2-benzyloxybenzyl)benzoate (2.1 g) in tetrahydrofuran (5 mL) at 0° C. After the mixture was stirred at the same temperature for 1 hour, to the mixture was added ethyl acetate, and the mixture was stirred for additional 30 minutes. To the reaction mixture were added water and dilute hydrochloric acid, and the mixture was extracted with ethyl acetate. The organic layer was washed with brine and dried over anhydrous magnesium sulfate, and the solvent was removed under reduced pressure to give 4-(2-benzyloxybenzyl)benzyl alcohol (1.9 g).
¹H-NMR (CDCl₃) δ ppm:
4.02 (2H, s), 4.65 (2H, s), 5.06 (2H, s), 6.85-6.95 (2H, m), 7.05-7.40 (11H, m)

REFERENCE EXAMPLE 22

4-(2-Benzyloxybenzyl)benzaldehyde

To a solution of 4-(2-benzyloxybenzyl)benzyl alcohol (1.0 g) in dichloromethane (50 mL) was added manganese dioxide (10 g), and the mixture was stirred at room temperature for 3 hours. After insoluble materials were removed by filtration, the solvent of the filtrate was removed under reduced pressure to give 4-(2-benzyloxybenzyl)benzaldehyde (0.97 g).
¹H-NMR (CDCl₃) δ ppm:
4.08 (2H, s), 5.03 (2H, s), 6.90-7.00 (2H, m), 7.10-7.40 (9H, m), 7.70-7.80 (2H, m), 9.96 (1H, s)

REFERENCE EXAMPLE 23

Ethyl (E)-3-[4-(2-hydroxybenzyl)phenyl]acrylate

To a solution of triethyl phosphonoacetate (0.89 mL) in tetrahydrofuran (30 mL) was added potassium tert-butoxide (0.50 g), and the mixture was stirred at room temperature for 15 minutes. A solution of 4-(2-benzyloxybenzyl)benzaldehyde (1.0 g) in tetrahydrofuran (10 mL) was added to the reaction mixture, and the mixture was stirred at room temperature for 6 hours. To the resulting mixture was added dilute hydrochloric acid, and the mixture was extracted with ethyl acetate. The organic layer was washed with brine and dried over anhydrous magnesium sulfate, and the solvent was removed under reduced pressure. The residue was purified by column chromatography on silica gel (eluent: hexane/ethyl acetate=10/1) to give ethyl (E)-3-[4-(2-benzyl-oxybenzyl)phenyl]acrylate (0.86 g). To the obtained ethyl (E)-3-[4-(2-benzyloxybenzyl)phenyl]acrylate (0.86 g) were added trifluoroacetic acid (9.5 mL), water (0.5 mL) and dimethyl sulfide (1.0 mL), and the mixture was stirred at room temperature overnight. The solvent was removed under reduced pressure, and the residue was purified by column chromatography on silica gel (eluent: hexane/ethyl acetate=3/1) to give ethyl (E)-3-[4-(2-hydroxybenzyl)phenyl]acrylate (0.51 g).
¹H-NMR (CDCl₃) δ ppm:
1.33 (3H, t, J=7.2 Hz), 4.01 (2H, s), 4.26 (2H, q, J=7.2 Hz), 4.96 (1H, s), 6.38 (1H, d, J=16.1 Hz), 6.75-6.80 (1H, m), 6.85-6.95 (1H, m), 7.05-7.20 (2H, m), 7.20-7.30 (2H, m), 7.40-7.50 (2H, m), 7.65 (1H, d, J=16.1 Hz)

REFERENCE EXAMPLE 24

(E)-2-[4-(2-Ethoxycarbonylvinyl)benzyl]phenyl β-D-glucopyranoside

To a suspension of ethyl (E)-3-[4-(2-hydroxybenzyl)-phenyl]acrylate (0.34 g) and 1,2,3,4,6-penta-O-acetyl-β-D-glucopyranose (1.4 g) in dichloromethane (3 mL) and toluene (9 mL) was added boron trifluoride diethyl ether complex (0.45 mL), and the mixture was stirred at room temperature overnight. The reaction mixture was concentrated under reduced pressure, and the residue was purified by column chromatography on silica gel (eluent: hexane/ethyl acetate=4/1) to give (E)-2-[4-(2-ethoxycarbonylvinyl)benzyl]phenyl 2,3,4,6-tetra-O-acetyl-β-D-glucopyranoside (0.47 g). To the solution of the obtained (E)-2-[4-(2-ethoxycarbonylvinyl)-benzyl]phenyl 2,3,4,6-tetra-O-acetyl-β-D-glucopyranoside (0.46 g) in methanol (5 mL) was added sodium methoxide (0.010 g), and the resulting mixture was stirred at room temperature for 30 minutes. The reaction mixture was concentrated under reduced pressure, and the residue was purified by column chromatography on silica gel (eluent: ethyl acetate) to give (E)-2-[4-(2-ethoxycarbonylvinyl)benzyl]phenyl β-D-glucopyranoside (0.31 g).
¹H-NMR (CD₃OD) δ ppm:
1.31 (3H, t, J=7.2 Hz), 3.30-3.55 (4H, m), 3.68 (1H, dd, J=5.3, 12.0 Hz), 3.88 (1H, dd, J=1.9, 12.0 Hz), 4.00 (1H, d, J=14.9 Hz), 4.15 (1H, dd, J=14.9 Hz), 4.22 (2H, q, J=7.2 Hz), 4.92 (1H, d, J=7.1 Hz), 6.45 (1H, d, J=16.1 Hz), 6.90-7.00 (1H, m), 7.05-7.20 (3H, m), 7.25-7.35 (2H, m), 7.45-7.55 (2H, m), 7.64 (1H, d, J=16.1 Hz)

REFERENCE EXAMPLE 25

2-(4-Methoxycarbonylbenzyl)phenyl 2,3,4,6-tetra-O-acetyl-β-D-glucopyranoside

To a suspension of methyl 4-(2-hydroxybenzyl)benzoate (0.053 g) and 1,2,3,4,6-penta-O-acetyl-β-D-glucopyranose (0.26 g) in dichloromethane (1 mL) and toluene (3 mL) was added boron trifluoride diethyl ether complex (0.083 mL), and the mixture was stirred at room temperature overnight. The reaction mixture was concentrated under reduced pressure, and the residue was purified by column chromatography on silica gel (eluent: hexane/ethyl acetate=4/1) to give 2-(4-methoxycarbonyl-benzyl)phenyl 2,3,4,6-tetra-O-acetyl-βD-glucopyranoside (0.067 g).
¹H-NMR (CDCl₃) δ ppm:
1.87 (3H, s), 2.03 (3H, s), 2.05 (3H, s), 2.07 (3H, s), 3.80-4.05 (6H, m), 4.16 (1H, dd, J=2.7, 12.4 Hz), 4.28 (1H, dd, J=5.8, 12.4 Hz), 5.10-5.20 (2H, m), 5.25-5.35 (2H, m), 6.95-7.10 (3H, m), 7.15-7.25 (3H, m), 7.90-7.95 (2H, m)

REFERENCE EXAMPLE 26

4-Allyloxy-2'-(methoxymethyloxy)diphenylmethanol

A Grignard reagent was prepared from 4-allyloxybromobenzene (1.7 g), magnesium (0.19 g), a catalytic amount of iodine and tetrahydrofuran (3 mL). To the obtained Grignard reagent was added a solution of 2-(methoxymethyloxy)benzaldehyde (0.88 g) in tetrahydrofuran (19 mL), and the mixture was stirred at room temperature for 30 minutes. A saturated aqueous ammonium chloride solution was added to the reaction mixture, and the mixture was extracted with ethyl acetate. The organic layer was washed with water and brine and dried over anhydrous sodium sulfate, and the solvent was removed under reduced pressure. The residue was purified by column chromatography on silica gel (eluent: hexane/ethyl acetate=5/1) to give 4-allyloxy-2'-(methoxymethyloxy)diphenylmethanol (1.2 g).
¹H-NMR (CDCl₃) δ ppm:
2.78 (1H, d, J=5.4 Hz), 3.31 (3H, s), 4.45-4.55 (2H, m), 5.12 (1H, d, J=7.0 Hz), 5.14 (1H, d, J=7.0 Hz), 5.20-5.30 (1H, m), 5.35-5.45 (1H, m), 5.95-6.10 (2H, m), 6.80-6.90 (2H, m), 6.95-7.05 (1H, m), 7.07 (1H, dd, J=0.9, 8.2 Hz), 7.20-7.35 (3H, m), 7.35 (1H, dd, J=1.8, 7.7 Hz)

REFERENCE EXAMPLE 27

4-Allyloxy-2'-(methoxymethyloxy)benzophenone

To a solution of 4-allyloxy-2'-(methoxymethyloxy)-diphenylmethanol (1.2 g) in dichloromethane (20 mL) was added a Dess-Martin reagent (1,1,1-triacetyloxy-1,1-dihydro-1,2-benziodoxol-3(1H)-one) (2.1 g) at 0° C., and the mixture was stirred for 1 hour. After warming to room temperature, the mixture was stirred overnight. To the reaction mixture were added diethyl ether and 1 mol/L aqueous sodium hydroxide solution, and the organic layer was separated. The organic layer was washed with 1 mol/L aqueous sodium hydroxide solution, water and brine, and dried over anhydrous sodium sulfate. The solvent was removed under reduced pressure to give 4-allyloxy-2'-(methoxymethyloxy)benzophenone (1.1 g).

$^1$H-NMR (CDCl$_3$) δ ppm:
3.33 (3H, s), 4.55-4.65 (2H, m), 5.08 (2H, s), 5.25-5.35 (1H, m), 5.35-5.50 (1H, m), 6.00-6.15 (1H, m), 6.85-7.00 (2H, m), 7.05-7.15 (1H, m), 7.15-7.25 (1H, m), 7.33 (1H, dd, J=1.5, 7.7 Hz), 7.35-7.50 (1H, m), 7.75-7.85 (2H, m)

REFERENCE EXAMPLE 28

4-Allyloxy-2'-hydroxybenzophenone

To a solution of 4-allyloxy-2'-(methoxymethyloxy)-benzophenone (1.1 g) in ethanol (15 mL) was concentrated hydrochloric acid (0.96 mL), and the mixture was stirred at room temperature overnight. The reaction mixture was concentrated under reduced pressure, and to the residue was added a saturated aqueous sodium hydrogen carbonate solution. The mixture was extracted with ethyl acetate, and the organic layer was washed with brine and dried over anhydrous sodium sulfate. The residue was purified by column chromatography on silica gel (eluent: hexane/ethyl acetate=15/1) to give 4-allyloxy-2'-hydroxy-benzophenone (0.87 g).

$^1$H-NMR (CDCl$_3$) δ ppm:
4.60-4.70 (2H, m), 5.30-5.40 (1H, m), 5.40-5.50 (1H, m), 6.00-6.15 (1H, m), 6.85-6.95 (1H, m), 6.95-7.05 (2H, m), 7.07 (1H, dd, J=1.0, 8.4 Hz), 7.45-7.55 (1H, m), 7.63 (1H, dd, J=1.6, 8.0 Hz), 7.65-7.75 (2H, m), 11.96 (1H, s)

REFERENCE EXAMPLE 29

2-(4-Allyloxybenzyl)phenol

To a solution of 4-allyloxy-2'-hydroxybenzophenone (0.87 g) in tetrahydrofuran (14 mL) was added triethylamine (0.53 mL) and methyl chloroformate (0.29 mL) at 0° C. After warming to room temperature, the mixture was stirred for 1.5 hours. Insoluble material was removed by filtration, and the solvent of the filtrate was removed under reduced pressure. To a solution of the residue in tetrahydrofuran (18 mL) and water (9 mL) was added sodium borohydride (0.52 g) at 0° C. After warming to room temperature, and the mixture was stirred for 2.5 hours. To the reaction mixture was added 0.5 mol/L hydrochloric acid, and the mixture was extracted with ethyl acetate. The organic layer was washed with water and brine, and dried over anhydrous sodium sulfate. The solvent was removed under reduced pressure, and the residue was purified by column chromatography on silica gel (eluent: hexane/ ethyl acetate=8/1) to give 2-(4-allyloxybenzyl)phenol (0.72 g).

$^1$H-NMR (CDCl$_3$) δ ppm:
3.93 (2H, s), 4.45-4.55 (2H, m), 4.73 (1H, brs), 5.20-5.30 (1H, m), 5.35-5.45 (1H, m), 5.95-6.10 (1H, m), 6.78 (1H, dd, J=1.3, 7.9 Hz), 6.80-6.95 (3H, m), 7.05-7.20 (4H, m)

REFERENCE EXAMPLE 30

2-(4-Allyloxybenzyl)phenyl 2,3,4,6-tetra-O-acetyl-β-D-glucopyranoside

To a solution of 2-(4-allyloxybenzyl)phenol (0.20 g) and 2,3,4,6-tetra-O-acetyl-1-O-trichloroacetoimidoyl-α-D-glucopyranose (0.45 g) in dichloromethane (8.5 mL) was added boron trifluoride diethyl ether complex (0.12 g), and the mixture was stirred at room temperature for 2 hours. To the reaction mixture was added a saturated aqueous sodium hydrogen carbonate, and the mixture was extracted with ethyl acetate. The organic layer was washed with brine and dried over anhydrous sodium sulfate, and the solvent was removed under reduced pressure. The residue was purified by column chromatography on silica gel (eluent: hexane/ethyl acetate=1/1) to give 2-(4-allyloxybenzyl)phenyl 2,3,4,6-tetra-O-acetyl-β-D-glucopyranoside (0.44 g).

$^1$H-NMR (CDCl$_3$) δ ppm:
1.90 (3H, s), 2.03 (3H, s), 2.05 (3H, s), 2.07 (3H, s), 3.80-3.95 (3H, m), 4.18 (1H, dd, J=2.5, 12.3 Hz), 4.28 (1H, dd, J=5.5, 12.3 Hz), 4.45-4.55 (2H, m), 5.11 (1H, d, J=7.5 Hz), 5.10-5.45 (5H, m), 5.95-6.10 (1H, m), 6.75-6.85 (2H, m), 6.95-7.10 (5H, m), 7.10-7.20 (1H, m)

REFERENCE EXAMPLE 31

4-(2-Benzyloxyethyl)-2'-(methoxymethyloxy)diphenylmethanol

The title compound was prepared in a similar manner to that described in Reference Example 26 using 4-(2-benzyloxyethyl)bromobenzene instead of 4-allyloxybromobenzene.

$^1$H-NMR (CDCl$_3$) δ ppm:
2.80 (1H, d, J=5.7 Hz), 2.90 (2H, t, J=7.1 Hz), 3.30 (3H, s), 3.66 (2H, t, J=7.1 Hz), 4.51 (2H, s), 5.10-5.20 (2H, m), 6.06 (1H, d, J=5.7 Hz), 6.95-7.05 (1H, m), 7.05-7.10 (1H, m), 7.10-7.20 (2H, m), 7.20-7.40 (9H, m)

REFERENCE EXAMPLE 32

4-(2-Benzyloxyethyl)-2'-(methoxymethyloxy)benzophenone

The title compound was prepared in a similar manner to that described in Reference Example 27 using 4-(2-benzyloxyethyl)-2'-(methoxymethyloxy)diphenylmethanol instead of 4-allyloxy-2'-(methoxymethyloxy)diphenylmethanol.

$^1$H-NMR (CDCl$_3$) δ ppm:
2.98 (2H, t, J=6.8 Hz), 3.29 (3H, s), 3.72 (2H, t, J=6.8 Hz), 4.51 (2H, s), 5.05 (2H, s), 7.05-7.15 (1H, m), 7.15-7.25 (1H, m), 7.25-7.40 (8H, m), 7.40-7.50 (1H, m), 7.70-7.80 (2H, m)

REFERENCE EXAMPLE 33

4-(2-Benzyloxyethyl)-2'-hydroxybenzophenone

The title compound was prepared in a similar manner to that described in Reference Example 28 using 4-(2-benzyloxyethyl)-2'-(methoxymethyloxy)benzophenone instead of 4-allyloxy-2'-(methoxymethyloxy)benzophenone.

¹H-NMR (CDCl₃) δ ppm:
3.02 (2H, t, J=6.8 Hz), 3.75 (2H, t, J=6.8 Hz), 4.55 (2H, s), 6.85-6.90 (1H, m), 7.05-7.10 (1H, m), 7.25-7.40 (7H, m), 7.45-7.55 (1H, m), 7.55-7.65 (3H, m), 12.02 (1H, s)

REFERENCE EXAMPLE 34

2-[4-(2-Benzyloxyethyl)benzyl]phenol

The title compound was prepared in a similar manner to that described in Reference Example 29 using 4-(2-benzyloxyethyl)-2'-hydroxybenzophenone instead of 4-allyloxy-2'-hydroxybenzophenone.

¹H-NMR (CDCl₃) δ ppm:
2.90 (2H, t, J=7.2 Hz), 3.66 (2H, t, J=7.2 Hz), 3.97 (2H, s), 4.52 (2H, s), 4.62 (1H, s), 6.75-6.85 (1H, m), 6.85-6.95 (1H, m), 7.05-7.20 (6H, m), 7.20-7.40 (5H, m)

REFERENCE EXAMPLE 35

4-(2-Benzyloxybenzyl)benzyl Chloride

To a solution of 4-(2-Benzyloxybenzyl)benzyl alcohol (0.67 g) in dichloromethane (30 mL) was added thionyl chloride (0.48 mL), and the mixture was heated under reflux for 1 hour. The reaction mixture was concentrated under reduced pressure, to the residue was added water, and the mixture was extracted with diethyl ether. The organic layer was washed with brine and dried over anhydrous sodium sulfate, and the solvent was distilled to give 4-(2-benzyloxybenzyl)benzyl chloride (0.68 g).

¹H-NMR (CDCl₃) δ ppm:
4.01 (2H, s), 4.56 (2H, s), 5.04 (2H, s), 6.85-7.40 (13H, m)

REFERENCE EXAMPLE 36

[4-(2-Benzyloxybenzyl)phenyl]acetonitrile

To a solution of 4-(2-benzyloxybenzyl)benzyl chloride (0.66 g) in N,N-dimethylformamide (20 mL) was added potassium cyanide (0.40 g), and the mixture was stirred at 60° C. for 18 hours. The reaction mixture was cooled to room temperature, and to the mixture was added water. The mixture was extracted with ethyl acetate, and the organic layer was washed with a saturated aqueous sodium hydrogen carbonate solution and brine, and dried over anhydrous magnesium sulfate. The solvent was removed under reduced pressure, and the residue was purified by column chromatography on silica gel (eluent: hexane/ethyl acetate=5/1-3/1) to give [4-(2-Benzyloxybenzyl)phenyl]-acetonitrile (0.54 g).

¹H-NMR (CDCl₃) δ ppm:
3.70 (2H, s), 4.01 (2H, s), 5.04 (2H, s), 6.85-7.40 (13H, m)

REFERENCE EXAMPLE 37

[4-(2-Hydroxybenzyl)phenyl]acetonitrile

Trifluoroacetic acid (17 mL), water (1 mL) and dimethyl sulfide (2 mL) were added to [4-(2-benzyloxybenzyl)-phenyl]acetonitrile (0.41 g), and the mixture was stirred at room temperature overnight. The reaction mixture was concentrated under reduced pressure, and the residue was purified by column chromatography on silica gel (eluent: hexane/ethyl acetate=3/1) to give [4-(2-hydroxybenzyl)phenyl]acetonitrile (0.26 g).

¹H-NMR (CDCl₃) δ ppm:
3.71 (2H, s), 3.99 (2H, s), 4.76 (1H, s), 6.77 (1H, dd, J=1.1, 7.9 Hz), 6.89 (1H, dt, 1.1, 7.5 Hz), 7.05-7.20 (2H, m), 7.20-7.30 (4H, m)

REFERENCE EXAMPLE 38

4-(2-Benzyloxybenzyl)benzoic Acid

To a solution of methyl 4-(2-benzyloxybenzyl)benzoate (1.0 g) in methanol (20 mL) was added 2 mol/L aqueous sodium hydroxide solution (7.5 mL), and the mixture was stirred at 60° C. for 5 hours. After dilute hydrochloric acid was added to the residue to acidify, the mixture was extracted with ethyl acetate. The organic layer was washed with brine and dried over anhydrous magnesium sulfate, and the solvent was removed under reduced pressure to give 4-(2-benzyloxybenzyl)benzoic acid (0.72 g).

¹H-NMR (DMSO-d₆) δ ppm:
4.01 (2H, s), 5.09 (2H, s), 6.85-6.95 (1H, m), 7.00-7.10 (1H, m), 7.15-7.40 (9H, m), 7.75-7.85 (2H, m), 12.77 (1H, brs)

REFERENCE EXAMPLE 39

4-(2-Benzyloxybenzyl)benzamide

To a suspension of 4-(2-benzyloxybenzyl)benzoic acid (0.70 g) in dichloromethane (10 mL) was added thionyl chloride (0.48 mL), and the mixture was stirred at 50° C. for 3 hours. The reaction mixture was concentrated under reduced pressure, to the residue was added 28% aqueous ammonia solution (50 mL), and the mixture was stirred at room temperature for 30 minutes. Insoluble materials were collected by filtration, washed with water and hexane, and dried under reduced pressure to give 4-(2-benzyloxybenzyl)benzamide (0.62 g).

¹H-NMR (DMSO-d₆) δ ppm:
3.98 (2H, s), 5.10 (2H, s), 6.85-6.95 (1H, m), 7.00-7.10 (1H, m), 7.15-7.40 (10H, m), 7.70-7.80 (2H, m), 7.88 (1H, brs)

REFERENCE EXAMPLE 40

4-(2-Hydroxybenzyl)benzamide

To a suspension of 4-(2-benzyloxybenzyl)benzamide (0.50 g) in ethanol (10 mL) was added 10% palladium-carbon powder (0.10 g), and the mixture was stirred under a hydrogen atmosphere at room temperature for 1 hour. Insoluble materials were collected by filtration, and the solvent of the filtrate was removed under reduced pressure to give 4-(2-hydroxybenzyl)benzamide (0.31 g).

¹H-NMR (DMSO-d₆) δ ppm:
3.90 (2H, s), 6.65-6.75 (1H, m), 6.75-6.85 (1H, m), 6.95-7.10 (2H, m), 7.20-7.30 (3H, m), 7.70-7.80 (2H, m), 7.86 (1H, brs), 9.40 (1H, s)

REFERENCE EXAMPLE 41

2-Benzyloxy-4'-(N,N-dimethylamino)diphenylmethanol

The title compound was prepared in a similar manner to that described in Reference Example 26 using 2-benzyloxybromobenzene instead of 4-allyloxybromobenzene, and 4-(N,N-dimethylamino)benzaldehyde instead of 2-(methoxymethyloxy)benzaldehyde.

$^1$H-NMR (CDCl$_3$) δ ppm:
2.77 (1H, d, J=5.3 Hz), 2.93 (6H, s), 5.04 (2H, s), 6.03 (1H, d, J=5.3 Hz), 6.65-6.75 (2H, m), 6.85-7.05 (2H, m), 7.15-7.45 (9H, m)

REFERENCE EXAMPLE 42

2-[4-(N,N-Dimethylamino)benzyl]phenol

To a solution of 2-benzyloxy-4'-(N,N-dimethylamino)-diphenylmethanol (0.85 g) in ethanol (25 mL) was added 10% palladium-carbon powder (0.34 g), and the mixture was stirred under a hydrogen atmosphere at room temperature for 22 hours. Insoluble materials were removed by filtration, and the solvent of the filtrate was removed under reduced pressure. The residue was purified by column chromatography on silica gel (eluent: hexane/ethyl acetate=4/1) to give 2-[4-(N, N-dimethylamino)-benzyl]phenol (0.35 g).

$^1$H-NMR (CDCl$_3$) δ ppm:
2.91 (6H, s), 3.91 (2H, s), 4.73 (1H, s), 6.65-6.75 (2H, m), 6.75-6.85 (1H, m), 6.85-6.95 (1H, m), 7.05-7.20 (4H, m)

REFERENCE EXAMPLE 43

2-[4-(N,N-Dimethylamino)benzyl]phenyl 2,3,4,6-tetra-O-acetyl-β-D-glucopyranoside The title compound was prepared in a similar manner to that described in Reference Example 30 using 2-[4-(N,N-dimethylamino)benzyl]phenol instead of 2-(4-allyloxybenzyl)phenol.

$^1$H-NMR (CDCl$_3$) δ ppm:
1.92 (3H, s), 2.03 (3H, s), 2.05 (3H, s), 2.08 (3H, s), 2.89 (6H, s), 3.80-3.90 (3H, m), 4.18 (1H, dd, J=2.3, 12.2 Hz), 4.28 (1H, dd, J=5.7, 12.2 Hz), 5.09 (1H, d, J=7.7 Hz), 5.15-5.25 (1H, m), 5.25-5.40 (2H, m), 6.60-6.70 (2H, m), 6.90-7.10 (5H, m), 7.10-7.20 (1H, m)

REFERENCE EXAMPLE 44

4-Benzyloxy-2'-(methoxymethyloxy)diphenylmethanol

The title compound was prepared in a similar manner to that described in Reference Example 26 using 2-(methoxymethyloxy)bromobenzene instead of 4-allyloxybromobenzene, and 4-benzyloxybenzaldehyde instead of 2-(methoxymethyloxy)-benzaldehyde.

$^1$H-NMR (CDCl$_3$) δ ppm:
2.78 (1H, d, J=5.4 Hz), 3.29 (3H, s), 5.04 (2H, s), 5.10-5.20 (2H, m), 6.03 (1H, d, J=5.4 Hz), 6.85-6.95 (2H, m), 6.95-7.10 (2H, m), 7.20-7.45 (9H, m)

REFERENCE EXAMPLE 45

4-Benzyloxy-2'-(methoxymethyloxy)benzophenone

The title compound was prepared in a similar manner to that described in Reference Example 27 using 4-benzyloxy-2'-(methoxymethyloxy)diphenylmethanol instead of 4-allyloxy-2'-(methoxymethyloxy)diphenylmethanol.

$^1$H-NMR (CDCl$_3$) δ ppm:
3.31 (3H, s), 5.07 (2H, s), 5.13 (2H, s), 6.95-7.05 (2H, m), 7.05-7.15 (1H, m), 7.15-7.25 (1H, m), 7.30-7.50 (7H, m), 7.75-7.85 (2H, m)

REFERENCE EXAMPLE 46

4-Benzyloxy-2'-hydroxybenzophenone

The title compound was prepared in a similar manner to that described in Reference Example 28 using 4-benzyloxy-2'-(methoxymethyloxy)benzophenone instead of 4-allyloxy-2'-(methoxymethyloxy)benzophenone.

$^1$H-NMR (CDCl$_3$) δ ppm:
5.16 (2H, s), 6.85-6.95 (1H, m), 7.00-7.10 (3H, m), 7.30-7.55 (6H, m), 7.63 (1H, dd, J=1.9, 8.2 Hz), 7.65-7.75 (2H, m), 11.95 (1H, s)

REFERENCE EXAMPLE 47

2-[(4-Benzyloxy)benzyl]phenol

The title compound was prepared in a similar manner to that described in Reference Example 29 using 4-benzyloxy-2'-hydroxybenzophenone instead of 4-allyloxy-2'-hydroxybenzophenone.

$^1$H-NMR (CDCl$_3$) δ ppm:
3.94 (2H, s), 4.70 (1H, s), 5.03 (2H, s), 6.75-6.80 (1H, m), 6.85-6.95 (3H, m), 7.05-7.20 (4H, m), 7.25-7.45 (5H, m)

REFERENCE EXAMPLE 48

2-[(4-Benzyloxy)benzyl]phenyl 2,3,4,6-tetra-O-acetyl-β-D-glucopyranoside

The title compound was prepared in a similar manner to that described in Reference Example 30 using 2-[(4-benzyloxy)benzyl]phenol instead of 2-(4-allyloxybenzyl)phenol.

$^1$H-NMR (CDCl$_3$) δ ppm:
1.88 (3H, s), 2.03 (3H, s), 2.05 (3H, s), 2.07 (3H, s), 3.80-3.90 (3H, m), 4.17 (1H, dd, J=2.4, 12.3 Hz), 4.28 (1H, dd, J=5.7, 12.3 Hz), 5.03 (2H, s), 5.10 (1H, d, J=7.2 Hz), 5.15-5.25 (1H, m), 5.25-5.40 (2H, m), 6.85-6.90 (2H, m), 6.95-7.10 (5H, m), 7.10-7.20 (1H, m), 7.25-7.45 (5H, m)

REFERENCE EXAMPLE 49

(E)-2-[4-(3-Hydroxy-1-prop-1-en-1-yl)benzyl]phenyl β-D-glucopyranoside

To a suspension of lithium aluminum hydride (0.036 g) in tetrahydrofuran (5 mL) was added a solution of (E)-2-[4-(2-ethoxycarbonylvinyl)benzyl]phenyl β-D-glucopyranoside (0.0.35 g) in tetrahydrofuran (5 mL) at 0° C., and the mixture was stirred for 1 hour. Ethyl acetate (10 mL) was added to the reaction mixture, and the mixture was stirred for 30 minutes. To the mixture were added water and dilute hydrochloric acid, and the mixture was extracted with ethyl acetate. The organic layer was washed with brine and dried over anhydrous magnesium sulfate, and the solvent was removed under reduced pressure to give (E)-2-[4-(3-hydroxy-1-prop-1-en-1-yl)benzyl]phenyl β-D-glucopyranoside (0.028 g).

$^1$H-NMR (CDCl$_3$) δ ppm:
3.35-3.55 (4H, m), 3.69 (1H, dd, J=5.0, 12.0 Hz), 3.88 (1H, dd, J=1.8, 12.0 Hz), 3.96 (1H, d, J=14.9 Hz), 4.09 (1H, d, J=14.9 Hz), 4.15-4.25 (2H, m), 4.91 (1H, d, J=7.5 Hz), 6.30 (1H, dt, J=5.9, 16.0 Hz), 6.50-6.60 (1H, m), 6.85-7.25 (6H, m), 7.25-7.35 (2H, m)

REFERENCE EXAMPLE 50

2-(4-Methoxycarbonylbenzyl)phenyl β-D-glucopyranoside

Sodium methoxide (0.006 g) was added to a solution of 2-(4-methoxycarbonylbenzyl)phenyl 2,3,4,6-tetra-O-acetyl-β-D-glucopyranoside (0.066 g) in methanol (5 mL), and the mixture was stirred at room temperature for 30 minutes. The reaction mixture was concentrated under reduced pressure, and the residue was purified by column chromatography on silica gel (eluent: ethyl acetate) to give 2-(4-methoxycarbonylbenzyl)phenyl β-D-glucopyranoside (0.040 g).

$^1$H-NMR (CD$_3$OD) δ ppm:
3.30-3.55 (4H, m), 3.68 (1H, dd, 5.4, 11.9 Hz), 3.85-3.95 (4H, m), 4.05 (1H, d, J=14.8 Hz), 4.19 (1H, d, J=14.8 Hz), 4.91 (1H, d, J=7.2 Hz), 6.90-7.00 (1H, m), 7.05-7.15 (1H, m), 7.15-7.20 (2H, m), 7.30-7.40 (2H, m), 7.85-7.95 (2H, m)

REFERENCE EXAMPLE 51

2-(4-Allyloxybenzyl)phenyl β-D-glucopyranoside

Sodium methoxide (28% methanol solution; 0.030 mL) was added to a solution of 2-(4-allyloxybenzyl)phenyl 2,3,4,6-tetra-O-acetyl-β-D-glucopyranoside (0.44 g) in methanol (2.5 mL) and tetrahydrofuran (1.5 mL), and the mixture was stirred at room temperature for 4 hours. The solvent of the reaction mixture was removed under reduced pressure. The residue was purified by column chromatography on silica gel (eluent: dichloromethane/methanol=10/1) to give 2-(4-allyloxybenzyl)phenyl β-D-glucopyranoside (0.23 g).

$^1$H-NMR (CD$_3$OD) δ ppm:
3.30-3.55 (4H, m), 3.69 (1H, dd, J=4.9, 11.9 Hz), 3.88 (1H, dd, J=2.0, 11.9 Hz), 3.92 (1H, d, J=14.8 Hz), 4.03 (1H, d, J=14.8 Hz), 4.45-4.55 (2H, m), 4.91 (1H, d, J=7.4 Hz), 5.15-5.25 (1H, m), 5.30-5.40 (1H, m), 5.95-6.10 (1H, m), 6.75-6.85 (2H, m), 6.85-6.95 (1H, m), 7.00-7.10 (1H, m), 7.10-7.20 (4H, m)

REFERENCE EXAMPLE 52

2-[4-(2-Benzyloxyethyl)benzyl]phenyl β-D-glucopyranoside

To a solution of 2-[4-(2-benzyloxyethyl)benzyl]phenol (3.2 g) and 1,2,3,4,6-penta-O-acetyl-β-D-glucopyranose (12 g) in toluene (34 mL) and dichloromethane (17 mL) was added boron trifluoride diethyl ether complex (3.8 mL), and the mixture was stirred at room temperature for 14 hours. To the reaction mixture were added a saturated aqueous sodium hydrogen carbonate solution, and the mixture was extracted with ethyl acetate. The organic layer was washed with a saturated aqueous sodium hydrogen carbonate solution and brine, and dried over anhydrous sodium sulfate, and the solvent was removed under reduced pressure. The residue was dissolved in methanol (50 mL), and to the solution was added sodium methoxide (28% methanol solution, 0.39 mL). The resulting mixture was stirred at room temperature for 2.5 hours. The solvent of the reaction mixture was removed under reduced pressure, and to the residue was added water. The mixture was extracted with ethyl acetate, and the organic layer was washed with brine and dried over anhydrous sodium sulfate, and the solvent was removed under reduced pressure. The residue was purified by column chromatography on silica gel (eluent: dichloromethane/methanol=10/1) to give 2-[4-(2-benzyloxyethyl)benzyl]phenyl β-D-glucopyranoside (3.4 g).

$^1$H-NMR (CD$_3$OD) δ ppm:
2.84 (2H, t, J=7.0 Hz), 3.35-3.55 (4H, m), 3.60-3.75 (3H, m), 3.88 (1H, dd, J=2.0, 12.0 Hz), 3.96 (1H, d, J=14.9 Hz), 4.07 (1H, d, J=14.9 Hz), 4.48 (2H, s), 4.91 (1H, d, J=7.4 Hz), 6.85-6.95 (1H, m), 7.00-7.20 (7H, m), 7.20-7.35 (5H, m)

REFERENCE EXAMPLE 53

2-(4-Carboxybenzyl)phenyl β-D-glucopyranoside

To a solution of 2-[4-(methoxycarbonyl)benzyl]phenyl β-D-glucopyranoside (0.050 g) in methanol (1 mL) was added 2 mol/L aqueous sodium hydroxide solution (0.26 mL), and the mixture was stirred at room temperature for 1 hour. The reaction mixture was purified by column chromatography on (benzenesulfonylpropyl) silica gel (eluent: methanol) to give 2-(4-carboxybenzyl)phenyl β-D-glucopyranoside (0.038 g).

$^1$H-NMR (CD$_3$OD) δ ppm:
3.30-3.55 (4H, m), 3.69 (1H, dd, J=5.1, 12.1 Hz), 3.88 (1H, dd, J=2.0, 12.1 Hz), 4.04 (1H, d, J=14.8 Hz), 4.19 (1H, d, J=14.8 Hz), 4.85-5.00 (1H, m), 6.85-7.00 (1H, m), 7.05-7.15 (1H, m), 7.15-7.20 (2H, m), 7.30-7.40 (2H, m), 7.85-7.95 (2H, m)

REFERENCE EXAMPLE 54

2-(4-Cyanomethylbenzyl)phenyl β-D-glucopyranoside 2-(4-Cyanomethylbenzyl)phenyl 2,3,4,6-tetra-O-acetyl-β-D-glucopyranoside was prepared in a similar manner to that described in Reference Example 25 using 4-(2-hydroxybenzyl)phenylacetonitrile instead of methyl 4-(2-hydroxybenzyl)benzoate. Then, the title compound was prepared in a similar manner to that described in Reference Example 50 using 2-(4-cyanomethylbenzyl)phenyl 2,3,4,6-tetra-O-acetyl-β-D-glucopyranoside instead of 2-(4-methoxycarbonylbenzyl)-phenyl 2,3,4,6-tetra-O-acetyl-BD-glucopyranoside.

$^1$H-NMR (CD$_3$OD) δ ppm:
3.35-3.55 (4H, m), 3.67 (1H, dd, J=5.3, 12.1 Hz), 3.82 (2H, s), 3.88 (1H, dd, J=2.1, 12.1 Hz), 3.99 (1H, d, J=14.9 Hz), 4.12 (1H, d, J=14.9 Hz), 4.91 (1H, d, J=7.6 Hz), 6.85-7.00 (1H, m), 7.00-7.10 (1H, m), 7.10-7.20 (2H, m), 7.20-7.30 (4H, m)

REFERENCE EXAMPLE 55

2-(4-Carbamoylbenzyl)phenyl β-D-glucopyranoside

To a suspension of 4-(2-hydroxybenzyl)benzamide (0.063 g) and 1,2,3,4,6-penta-O-acetyl-β-D-glucopyranose (0.33 g) in toluene (3 mL) was added boron trifluoride diethyl ether complex (0.11 mL), and the mixture was stirred at room temperature overnight. The reaction mixture was concentrated under reduced pressure, and the residue was purified by column chromatography on silica gel (eluent: hexane/ethyl acetate=4/1) to give 2-(4-carbamoylbenzyl)phenyl 2,3,4,6-tetra-O-acetyl-β-D-glucopyranoside. To a solution of the obtained 2-(4-carbamoylbenzyl)phenyl 2,3,4,6-tetra-O-acetyl-β-D-glucopyranoside in methanol (5 mL) was added sodium methoxide (0.005 g), and the mixture was stirred at room temperature for 30 minutes. The reaction mixture was concentrated under reduced pressure, and the residue was purified by column chromatography on silica gel (eluent: ethyl acetate/ethanol=5/1) to give 2-(4-carbamoylbenzyl)phenyl β-D-glucopyranoside (0.068 g).

$^1$H-NMR (CD$_3$OD) δ ppm:

3.30-3.55 (4H, m), 3.68 (1H, dd, J=5.5, 11.9 Hz), 3.88 (1H, dd, J=2.1, 11.9 Hz), 4.04 (1H, d, J=14.9 Hz), 4.19 (1H, d, J=14.9 Hz), 4.92 (1H, d, J=7.5 Hz), 6.90-7.00 (1H, m), 7.05-7.15 (1H, m), 7.15-7.20 (2H, m), 7.30-7.40 (2H, m), 7.70-7.80 (2H, m)

REFERENCE EXAMPLE 56

2-[4-(N,N-Dimethylamino)benzyl]phenyl β-D-glucopyranoside

To a solution of 2-[4-(N,N-dimethylamino)benzyl]phenyl 2,3,4,6-tetra-O-acetyl-β-D-glucopyranoside (0.10 g) in methanol (2 mL) and tetrahydrofuran (1 mL) was added sodium methoxide (28% methanol solution; 0.007 mL), and the mixture was stirred at room temperature for 70 minutes. The reaction mixture was concentrated under reduced pressure, and the residue was purified by column chromatography on aminopropyl silica gel (eluent: dichloromethane/methanol=8/1) to give 2-[4-(N,N-dimethylamino)benzyl]phenyl β-D-glucopyranoside (0.069 g).

$^1$H-NMR (CD$_3$OD) δ ppm:

2.85 (6H, s), 3.35-3.55 (4H, m), 3.69 (1H, dd, J=5.2, 12.0 Hz), 3.88 (1H, dd, J=1.9, 12.0 Hz), 3.89 (1H, d, J=15.0 Hz), 3.98 (1H, d, J=15.0 Hz), 4.90 (1H, d, J=7.6 Hz), 6.65-6.75 (2H, m), 6.85-6.95 (1H, m), 7.00-7.05 (1H, m), 7.05-7.10 (2H, m), 7.10-7.15 (2H, m)

REFERENCE EXAMPLE 57

2-[4-(Benzyloxy)benzyl]phenyl β-D-glucopyranoside

The title compound was prepared in a similar manner to that described in Reference Example 51 using 2-[4-(benzyloxy)benzyl]phenyl 2,3,4,6-tetra-O-acetyl-β-D-glucopyranoside instead of 2-(4-allyloxybenzyl)phenyl 2,3,4,6-tetra-O-acetyl-β-D-glucopyranoside.

$^1$H-NMR (CD$_3$OD) δ ppm:

3.35-3.55 (4H, m), 3.69 (1H, dd, J=5.0, 12.0 Hz), 3.88 (1H, dd, J=2.0, 12.0 Hz), 3.92 (1H, d, J=14.8 Hz), 4.03 (1H, d, J=14.8 Hz), 4.91 (1H, d, J=7.3 Hz), 5.03 (2H, s), 6.80-6.95 (3H, m), 7.00-7.10 (1H, m), 7.10-7.20 (4H, m), 7.25-7.45 (5H, m)

REFERENCE EXAMPLE 58

4-[2-(Methoxymethyloxy)ethyl]bromobenzene

To a solution of 2-(4-bromophenyl)ethanol (1.0 g) and diisopropylethylamine (1.3 mL) in dichloromethane (5 mL) was added chloromethylmethyl ether (0.75 mL), and the mixture was stirred at room temperature for 2 hours. To the reaction mixture was added water, and the organic layer was separated and dried over anhydrous sodium sulfate. The solvent was removed under reduced pressure, and the residue was purified by column chromatography on silica gel (eluent: hexane/ethyl acetate=15/1-10/1) to give 4-[2-(methoxymethyloxy)ethyl]bromobenzene (1.2 g).

$^1$H-NMR (CDCl$_3$) δ ppm:

2.85 (2H, t, J=6.8 Hz), 3.28 (3H, s), 3.74 (2H, t, J=6.8 Hz), 4.60 (2H, s), 7.05-7.15 (2H, m), 7.35-7.45 (2H, m)

REFERENCE EXAMPLE 59

2-Hydroxy-4-methoxy-4'-[2-(methoxymethyloxy)ethyl]diphenylmethanol

To a solution of 4-[2-(methoxymethyloxy)ethyl]-bromobenzene (0.61 g) in tetrahydrofuran (12 mL) was added tert-butyllithium (1.5 mol/L pentane solution, 1.8 mL) under an argon atmosphere at −78° C., and the mixture was stirred for 30 minutes. A solution of 2-hydroxy-4-methoxybenzaldehyde (0.15 g) in tetrahydrofuran (6 mL) was added to the reaction mixture, and the mixture was stirred for 25 minutes after warming to 0° C. A saturated aqueous ammonium chloride solution was added to the reaction mixture, and the mixture was extracted with diethylether. The organic layer was dried over anhydrous sodium sulfate, and the solvent was removed under reduced pressure. The residue was purified by column chromatography on silica gel (eluent: hexane/ethyl acetate=2/1) to give 2-hydroxy-4-methoxy-4'-[2-(methoxymethyloxy)ethyl]diphenylmethanol (0.31 g).

$^1$H-NMR (CDCl$_3$) δ ppm:

2.77 (1H, d, J=2.9 Hz), 2.90 (2H, t, J=6.9 Hz), 3.29 (3H, s), 3.70-3.80 (5H, m), 4.61 (2H, s), 5.96 (1H, d, J=2.9 Hz), 6.35 (1H, dd, J=2.1, 8.5 Hz), 6.48 (1H, d, J=2.1 Hz), 6.70 (1H, d, J=8.5 Hz), 7.20-7.35 (4H, m), 8.04 (1H, s)

REFERENCE EXAMPLE 60

5-Methoxy-2-(4-[2-(methoxymethyloxy)ethyl]benzyl)phenol

To a solution of 2-hydroxy-4-methoxy-4'-[2-(methoxymethyloxy)ethyl]diphenylmethanol (0.31 g) in ethanol (10 mL) was added 10% palladium-carbon powder (0.061 g), and the mixture was stirred under a hydrogen atmosphere at room temperature for 1 hour. Insoluble materials were removed by filtration, and the solvent of the filtrate was removed under reduced pressure. The residue was purified by column chromatography on silica gel (eluent: hexane/ethyl acetate=5/2) to give 5-methoxy-2-{4-[2-(methoxymethyloxy)ethyl]-benzyl}phenol (0.19 g).

$^1$H-NMR (CDCl$_3$) δ ppm: 2.86 (2H, t, J=7.0 Hz), 3.29 (3H, s), 3.74 (2H, t, J=7.0 Hz), 3.76 (3H, s), 3.90 (2H, s), 4.61 (2H, s), 4.77 (1H, s), 6.38 (1H, d, J=2.5 Hz), 6.45 (1H, dd, J=2.5, 8.5 Hz), 7.01 (1H, d, J=8.5 Hz), 7.10-7.20 (4H, m)

REFERENCE EXAMPLE 61

5-Methoxy-2-{4-[2-(methoxymethyloxy)ethyl]benzyl}phenyl 2,3,4,6-tetra-O-acetyl-β-D-glucopyranoside To a solution of 5-methoxy-2-(4-[2-(methoxymethyloxy)ethyl]benzyl)phenol (0.19 g) and 2,3,4,6-tetra-O-acetyl-1-O-trichloroacetoimidoyl-α-D-glucopyranose (0.40 g) in dichloromethane (15 mL) was added boron trifluoride diethyl ether complex (0.088 mL), and the mixture was stirred for 20 minutes. To the reaction mixture was added a saturated aqueous sodium hydrogen carbonate, and the organic layer was separated and dried over anhydrous sodium sulfate. The solvent was removed under reduced pressure, and the residue was purified by column chromatography on silica gel (eluent: hexane/ethyl acetate=1/1) to give 5-methoxy-2-{4-[2-(methoxymethyloxy)ethyl]-benzyl}phenyl 2,3,4,6-tetra-O-acetyl-β-D-glucopyranoside (0.33 g).

$^1$H-NMR (CDCl$_3$) δ ppm:

1.85 (3H, s), 2.02 (3H, s), 2.05 (3H, s), 2.10 (3H, s), 2.85 (2H, t, J=7.1 Hz), 3.30 (3H, s), 3.72 (2H, t, J=7.1 Hz), 3.77 (3H, s), 3.75-3.85 (2H, m), 3.80-3.95 (1H, m), 4.19 (1H, dd, J=2.4, 12.2 Hz), 4.25 (1H, dd, J=5.9, 12.2 Hz), 4.60 (2H, s), 5.07 (1H, d, J=7.7 Hz), 5.10-5.20 (1H, m), 5.25-5.35 (2H, m), 6.53 (1H, dd, J=2.5, 8.7 Hz), 6.65 (1H, d, J=2.5 Hz), 6.94 (1H, d, J=8.7 Hz), 7.00-7.20 (4H, m)

REFERENCE EXAMPLE 62

Methyl 3-benzyloxy-4-(4-ethylbenzyl)benzoate

To a solution of methyl 4-(4-ethylbenzyl)-3-hydroxybenzoate (1.28 g) in N,N-dimethylformamide (14 mL) were added potassium carbonate (0.98 g) and benzyl bromide (0.62 mL), and the mixture was stirred at room temperature for 19 hours. The reaction mixture was poured into water and extracted with diethyl ether twice. The combined organic layer was washed with water and dried over anhydrous magnesium sulfate. The solvent was removed under reduced pressure, and the residue was purified by column chromatography on silica gel (eluent: hexane/ethyl acetate=5/1) to give methyl 3-benzyloxy-4-(4-ethylbenzyl)benzoate (1.6 g).
$^1$H-NMR (CDCl$_3$) δ ppm:
1.22 (3H, t, J=7.7 Hz), 2.61 (2H, q, J=7.7 Hz), 3.90 (3H, s), 4.02 (2H, s), 5.11 (2H, s), 7.00-7.20 (5H, m), 7.25-7.40 (5H, m), 7.55-7.65 (2H, m)

REFERENCE EXAMPLE 63

3-Benzyloxy-4-(4-ethylbenzyl)benzoic Acid

Methyl 3-benzyloxy-4-(4-ethylbenzyl)benzoate (1.6 g) was dissolved in a mixture of tetrahydrofuran (5 mL) and ethanol (5 mL). To the solution was added 2 mol/L aqueous sodium hydroxide solution (10 mL), and the mixture was stirred at 80° C. for 1 hour. After cooling to room temperature, the resulting solution was acidified with 2 mol/L hydrochloric acid. The mixture was stirred under ice-cooling for 3 minutes, and the precipitates were collected by filtration, washed with water and dried to give 3-benzyloxy-4-(4-ethylbenzyl)benzoic acid (1.4 g).
$^1$H-NMR (DMSO-d$_6$) δ ppm:
1.14 (3H, t, J=7.6 Hz), 2.55 (2H, q, J=7.6 Hz), 3.96 (2H, s), 5.18 (2H, s), 7.05-7.15 (4H, m), 7.20-7.40 (6H, m), 7.50 (1H, dd, J=1.5, 7.9 Hz), 7.55 (1H, d, J=1.5 Hz), 12.84 (1H, s)

REFERENCE EXAMPLE 64

5-Amino-2-(4-ethylbenzyl)phenol

To a solution of 3-benzyloxy-4-(4-ethylbenzyl)benzoic acid (1.4 g) and triethylamine (1.3 mL) in 1,4-dioxane (10 mL) was added diphenylphosphoryl azide (1.3 g) in 1,4-dioxane (10 mL), and the mixture was stirred at 100° C. for 1 hour. Benzyl alcohol (1.6 mL) was added to the reaction mixture, and the mixture was stirred at the same temperature for 7 hours. The solvent of the reaction mixture was removed under reduced pressure, and the residue was purified by column chromatography on silica gel (eluent: hexane/ethyl acetate=4/1) to give benzyl N-[3-benzyloxy-4-(4-ethylbenzyl)phenyl]carbamate (1.4 g). To a solution of the obtained benzyl N-[3-benzyloxy-4-(4-ethylbenzyl)phenyl]carbamate (1.4 g) in methanol (15 mL) was added 10% palladium-carbon powder (0.28 g), and the mixture was stirred under a hydrogen atmosphere for 11 hours. Insoluble materials were removed by filtration, and the solvent of the filtrate was removed under reduced pressure. The residue was purified by column chromatography on silica gel (eluent: hexane/ethyl acetate=1/1) to give 5-amino-2-(4-ethylbenzyl)-phenol (0.54 g).
$^1$H-NMR (CDCl$_3$) δ ppm:
1.21 (3H, t, J=7.7 Hz), 2.61 (2H, q, J=7.7 Hz), 3.56 (2H, brs), 3.85 (2H, s), 4.57 (1H, s), 6.18 (1H, d, J=2.4 Hz), 6.25 (1H, dd, J=2.4, 8.1 Hz), 6.89 (1H, d, J=8.1 Hz), 7.05-7.15 (4H, m)

REFERENCE EXAMPLE 65

Benzyl N-[4-(4-ethylbenzyl)-3-hydroxyphenyl]carbamate

To a solution of 5-amino-2-(4-ethylbenzyl)phenol (0.25 g) in tetrahydrofuran (10 mL) was added N-benzyloxycarbonyloxy-succinimide (0.41 g), and the mixture was stirred at room temperature for 22 hours. The reaction mixture was purified by column chromatography on silica gel (eluent: hexane/ethyl acetate=5/1) to give benzyl N-[4-(4-ethylbenzyl)-3-hydroxyphenyl]carbamate (0.40 g).
$^1$H-NMR (CDCl$_3$) δ ppm:
1.21 (3H, t, J=7.7 Hz), 2.60 (2H, q, J=7.7 Hz), 3.90 (2H, s), 5.00 (1H, brs), 5.19 (2H, s), 6.59 (1H, brs), 6.70 (1H, dd, J=2.3, 8.2 Hz), 7.01 (1H, d, J=8.2 Hz), 7.05-7.20 (5H, m), 7.30-7.45 (5H, m)

REFERENCE EXAMPLE 66

5-Benzyloxycarbonylamino-2-(4-ethylbenzyl)phenyl 2,3,4,6-tetra-O-acetyl-β-D-glucopyranoside The title compound was prepared in a similar manner to that described in Reference Example 61 using benzyl N-[4-(4-ethylbenzyl)-3-hydroxyphenyl]carbamate instead of 5-methoxy-2-{4-[2-(methoxymethyloxy)ethyl]benzyl}phenol.
$^1$H-NMR (CDCl$_3$) δ ppm:
1.19 (3H, t, J=7.5 Hz), 1.85 (3H, s), 2.02 (3H, s), 2.03 (3H, s), 2.05 (3H, s), 2.59 (2H, q, J=7.5 Hz), 3.70-3.95 (3H, m), 4.10-4.40 (2H, m), 5.00-5.40 (6H, m), 6.63 (1H, brs), 6.74 (1H, dd, J=1.9, 8.2 Hz), 6.95 (1H, d, J=8.2 Hz), 6.95-7.10 (4H, m), 7.20-7.60 (6H, m)

REFERENCE EXAMPLE 67

5-Amino-2-(4-ethylbenzyl)phenyl 2,3,4,6-tetra-O-acetyl-β-D-glucopyranoside

To a solution of 5-benzyloxycarbonylamino-2-(4-ethylbenzyl)phenyl 2,3,4,6-tetra-O-acetyl-β-D-glucopyranoside (0.35 g) in tetrahydrofuran (4 mL) was added 10% palladium-carbon powder (0.07 g), and the mixture was stirred under a hydrogen atmosphere at room temperature for 8 hours. Insoluble materials were removed by filtration, and the solvent of the filtrate was removed under reduced pressure. The residue was purified by column chromatography on silica gel (eluent: hexane/ethyl acetate=2/3-dichloromethane/ethyl acetate=1/1) to give 5-amino-2-(4-ethylbenzyl)phenyl 2,3,4,6-tetra-O-acetyl-β-D-glucopyranoside (0.19 g).
$^1$H-NMR (CDCl$_3$) δ ppm:
1.19 (3H, t, J=7.6 Hz), 1.84 (3H, s), 2.02 (3H, s), 2.05 (3H, s), 2.09 (3H, s), 2.59 (2H, q, J=7.6 Hz), 3.59 (2H, brs), 3.70-3.90 (3H, m), 4.18 (1H, dd, J=2.5, 12.2 Hz), 4.28 (1H, dd, J=5.3, 12.2 Hz), 5.04 (1H, d, J=7.5 Hz), 5.10-5.35 (3H, m), 6.34 (1H, dd, J=2.1, 8.0 Hz), 6.42 (1H, d, J=2.1 Hz), 6.82 (1H, d, J=8.0 Hz), 6.95-7.15 (4H, m)

REFERENCE EXAMPLE 68

2-(Methoxymethyloxy)-4,6-dimethylbenzaldehyde

To a solution of 2-hydroxy-4,6-dimethylbenzaldehyde (0.75 g) and diisopropylethylamine (1.4 mL) in dichloromethane (20 mL) was added chloromethyl methyl ether (0.57 mL), and the mixture was stirred at room temperature for 24 hours. Water was added to the reaction mixture, and the mixture was extracted with diethyl ether. The organic layer was washed with brine and water and dried over anhydrous sodium sulfate. The solvent was removed under reduced pressure, and the residue was purified by column chromatography on silica gel (eluent: hexane/ethyl acetate=20/1) to give 2-(methoxymethyloxy)-4,6-dimethylbenzaldehyde (0.57 g).

$^1$H-NMR (CDCl$_3$) δ ppm:

2.34 (3H, s), 2.55 (3H, s), 3.51 (3H, s), 5.26 (2H, s), 6.65-6.70 (1H, m), 6.85-6.90 (1H, m), 10.61 (1H, s)

REFERENCE EXAMPLE 69

4'-(3-Benzyloxypropyl)-2-(methoxymethyloxy)-4,6-dimethyldiphenylmethanol

A Grignard reagent was prepared from 4-(3-benzyloxypropyl)bromobenzene (1.3 g), magnesium (0.11 g), a catalytic amount of iodine and tetrahydrofuran (4.4 mL). To the obtained Grignard reagent was added a solution of 2-(methoxymethyloxy)-4,6-dimethylbenzaldehyde (0.57 g) in tetrahydrofuran (10 mL), and the mixture was stirred for 20 minutes. A saturated aqueous ammonium chloride solution was added to the reaction mixture, and the mixture was extracted with ethyl acetate. The organic layer was washed with water and brine, and dried over anhydrous sodium sulfate, and the solvent was removed under reduced pressure. The residue was purified by column chromatography on silica gel (eluent: hexane/ethyl acetate=4/1) to give 4'-(3-benzyloxypropyl)-2-(methoxymethyloxy)-4,6-dimethyldiphenylmethanol (1.1 g).

$^1$H-NMR (CDCl$_3$) δ ppm:

1.80-1.95 (2H, m), 2.31 (3H, s), 2.32 (3H, s), 2.60-2.75 (2H, m), 3.12 (3H, s), 3.46 (2H, t, J=6.2 Hz), 3.91 (1H, d, J=10.7 Hz), 4.49 (2H, s), 4.93 (1H, d, J=6.5 Hz), 5.03 (1H, d, J=6.5 Hz), 6.03 (1H, d, J=10.7 Hz), 6.70-6.75 (1H, m), 6.75-6.80 (1H, m), 7.05-7.10 (2H, m), 7.15-7.20 (2H, m), 7.20-7.40 (5H, m)

REFERENCE EXAMPLE 70

4'-(3-Hydroxypropyl)-2-(methoxymethyloxy)-4,6-dimethyldiphenylmethane

To a solution of 4'-(3-benzyloxypropyl)-2-(methoxymethyloxy)-4,6-dimethyldiphenylmethanol (1.1 g) in ethanol (27 mL) was added 10% palladium-carbon powder (0.46 g), and the mixture was stirred under a hydrogen atmosphere at room temperature for 17 hours. Insoluble materials were removed by filtration, and the solvent of the filtrate was removed under reduced pressure to give 4'-(3-hydroxypropyl)-2-(methoxymethyloxy)-4,6-dimethyldiphenylmethane (0.85 g).

$^1$H-NMR (CDCl$_3$) δ ppm:

1.80-1.90 (2H, m), 2.20 (3H, s), 2.30 (3H, s), 2.60-2.70 (2H, m), 3.36 (3H, s), 3.60-3.70 (2H, m), 4.00 (2H, s), 5.13 (2H, s), 6.65-6.70 (1H, m), 6.75-6.85 (1H, m), 7.00-7.10 (4H, m)

REFERENCE EXAMPLE 71

4'-(3-Benzoyloxypropyl)-2-(methoxymethyloxy)-4,6-dimethyldiphenylmethane

To a solution of 4'-(3-hydroxypropyl)-2-(methoxymethyloxy)-4,6-dimethyldiphenylmethane (0.85 g), triethylamine (0.49 mL) and 4-(dimethylamino)pyridine (0.033 g) in dichloromethane (14 mL) was added benzoyl chloride (0.38 mL), and the mixture was stirred at room temperature for 18 hours. To the reaction mixture was added water, and the mixture was extracted with ethyl acetate. The organic layer was washed with brine and dried over anhydrous sodium sulfate. The solvent was removed under reduced pressure, and the residue was purified by column chromatography on silica gel (eluent: hexane/ethyl acetate=20/1) to give 4'-(3-benzoyloxypropyl)-2-(methoxymethyloxy)-4,6-dimethyldiphenylmethane (1.1 g).

$^1$H-NMR (CDCl$_3$) δ ppm:

2.00-2.10 (2H, m), 2.20 (3H, s), 2.30 (3H, s), 2.65-2.75 (2H, m), 3.36 (3H, s), 4.00 (2H, s), 4.25-4.35 (2H, m), 5.13 (2H, s), 6.65-6.70 (1H, m), 6.75-6.85 (1H, m), 7.00-7.10 (4H, m), 7.40-7.50 (2H, m), 7.50-7.60 (1H, m), 8.00-8.10 (2H, m)

REFERENCE EXAMPLE 72

2-[4-(3-Benzoyloxypropyl)benzyl]-3,5-dimethylphenol

To a solution of 4'-(3-benzoyloxypropyl)-2-(methoxymethyloxy)-4,6-dimethyldiphenylmethane (1.1 g) in methanol (13 mL) was added p-toluenesulfonic acid monohydrate (0.096 g), and the mixture was stirred at 60° C. for 4 hours. The reaction mixture was concentrated under reduced pressure, and the residue was purified by column chromatography on silica gel (eluent: hexane/ethyl acetate=6/1) to give 2-[4-(3-benzoyloxypropyl)-benzyl]-3,5-dimethylphenol (0.89 g).

$^1$H-NMR (CDCl$_3$) δ ppm:

2.00-2.10 (2H, m), 2.23 (3H, s), 2.26 (3H, s), 2.65-2.80 (2H, m), 3.98 (2H, s), 4.25-4.35 (2H, m), 4.53 (1H, s), 6.45-6.55 (1H, m), 6.60-6.70 (1H, m), 7.00-7.15 (4H, m), 7.40-7.50 (2H, m), 7.50-7.60 (1H, m), 8.00-8.10 (2H, m)

REFERENCE EXAMPLE 73

4'-(2-Benzyloxyethyl)-2-(methoxymethyloxy)-4,6-dimethyldiphenylmethanol

The title compound was prepared in a similar manner to that described in Reference Example 69 using 4-(2-benzyloxyethyl)bromobenzene instead of 4-(3-benzyloxypropyl)bromobenzene.

$^1$H-NMR (CDCl$_3$) δ ppm:

2.30 (3H, s), 2.32 (3H, s), 2.89 (2H, t, J=7.3 Hz), 3.13 (3H, s), 3.64 (2H, t, J=7.3 Hz), 3.89 (1H, d, J=10.7 Hz), 4.50 (2H, s), 4.93 (1H, d, J=6.6 Hz), 5.02 (1H, d, J=6.6 Hz), 6.03 (1H, d, J=10.7 Hz), 6.70-6.75 (1H, m), 6.75-6.80 (1H, m), 7.10-7.35 (9H, m)

REFERENCE EXAMPLE 74

4'-(2-Hydroxyethyl)-2-(methoxymethyloxy)-4,6-dimethyldiphenylmethane

The title compound was prepared in a similar manner to that described in Reference Example 70 using 4'-(2-benzyloxyethyl)-2-(methoxymethyloxy)-4,6-dimethyldiphenylmethanol instead of 4'-(3-benzyloxypropyl)-2-(methoxymethyloxy)-4,6-dimethyldiphenylmethanol.

$^1$H-NMR (CDCl$_3$) δ ppm:
1.31 (1H, t, J=5.9 Hz), 2.20 (3H, s), 2.30 (3H, s), 2.80 (2H, t, J=6.5 Hz), 3.37 (3H, s), 3.75-3.85 (2H, m), 4.01 (2H, s), 5.13 (2H, s), 6.65-6.70 (1H, m), 6.75-6.85 (1H, m), 7.05-7.10 (4H, m)

REFERENCE EXAMPLE 75

4'-(2-Benzoyloxyethyl)-2-(methoxymethyloxy)-4,6-dimethyldiphenylmethane

The title compound was prepared in a similar manner to that described in Reference Example 71 using 4'-(2-hydroxyethyl)-2-(methoxymethyloxy)-4,6-dimethyldiphenylmethane instead of 4'-(3-hydroxypropyl)-2-(methoxymethyloxy)-4,6-dimethyldiphenylmethane.

$^1$H-NMR (CDCl$_3$) δ ppm:
2.19 (3H, s), 2.30 (3H, s), 3.01 (2H, t, J=7.0 Hz), 3.33 (3H, s), 4.01 (2H, s), 4.47 (2H, t, J=7.0 Hz), 5.11 (2H, s), 6.65-6.70 (1H, m), 6.75-6.85 (1H, m), 7.00-7.10 (2H; m), 7.10-7.15 (2H, m), 7.35-7.45 (2H, m), 7.50-7.60 (1H, m), 7.95-8.05 (2H, m)

REFERENCE EXAMPLE 76

2-[4-(2-Benzoyloxyethyl)benzyl]-3,5-dimethylphenol

The title compound was prepared in a similar manner to that described in Reference Example 72 using 4'-(2-benzoyloxyethyl)-2-(methoxymethyloxy)-4,6-dimethyldiphenylmethane instead of 4'-(3-benzoyloxypropyl)-2-(methoxymethyloxy)-4,6-dimethyldiphenylmethane.

$^1$H-NMR (CDCl$_3$) δ ppm:
2.22 (3H, s), 2.25 (3H, s), 3.02 (2H, t, J=7.0 Hz), 3.99 (2H, s), 4.49 (2H, t, J=7.0 Hz), 4.60 (1H, brs), 6.45-6.55 (1H, m), 6.60-6.65 (1H, m), 7.05-7.20 (4H, m), 7.35-7.45 (2H, m), 7.50-7.60 (1H, m), 7.95-8.05 (2H, m)

REFERENCE EXAMPLE 77

2-(4-Ethylbenzyl)-5-methylaminophenyl 2,3,4,6-tetra-O-acetyl-β-D-glucopyranoside To a solution of 5-benzyloxycarbonylamino-2-(4-ethylbenzyl)phenyl 2,3,4,6-tetra-O-acetyl-β-D-glucopyranoside (0.42 g) and methyl iodide (0.067 mL) in tetrahydrofuran (7 mL) was added sodium hydride (60%, 0.034 g) at 0° C. The reaction mixture was warmed to room temperature and stirred for 5 hours. Methyl iodide (0.13 mL) and sodium hydride (60%, 0.020 g) were added to the reaction mixture, and the mixture was stirred at room temperature for additional 1 hour. The reaction mixture was poured into water, and the mixture was extracted with ethyl acetate. The organic layer was washed with water and dried over anhydrous magnesium sulfate. The solvent was removed under reduced pressure, and the residue was purified by column chromatography on aminopropyl silica gel (eluent: hexane/ethyl acetate=2/1) to give 5-(N-benzyloxycarbonyl-N-methyl)-amino-2-(4-ethylbenzyl)phenyl 2,3,4,6-tetra-O-acetyl-β-D-glucopyranoside (0.30 g). To the solution of the obtained 5-(N-benzyloxycarbonyl-N-methyl)amino-2-(4-ethylbenzyl)-phenyl 2,3,4,6-tetra-O-acetyl-β-D-glucopyranoside (0.30 g) in tetrahydrofuran (5 mL) was added 10% palladium-carbon powder (0.060 g), and the mixture was stirred under a hydrogen atmosphere at room temperature for 6 hours. Insoluble materials were removed by filtration, and the solvent of the filtrate was removed under reduced pressure. The residue was purified by column chromatography on silica gel (eluent: hexane/ethyl acetate=1/1) to give 2-(4-ethylbenzyl)-5-methylaminophenyl 2,3,4,6-tetra-O-acetyl-β-D-glucopyranoside (0.15 g).

$^1$H-NMR (CDCl$_3$) δ ppm:
1.19 (3H, t, J=7.7 Hz), 1.84 (3H, s), 2.02 (3H, s), 2.04 (3H, s), 2.06 (3H, s), 2.58 (2H, q, J=7.7 Hz), 2.81 (3H, s), 3.65 (1H, brs), 3.70-3.95 (3H, m), 4.18 (1H, dd, J=2.5, 12.3 Hz), 4.26 (1H, dd, J=5.0, 12.3 Hz), 5.07 (1H, d, J=7.7 Hz), 5.10-5.20 (1H, m), 5.20-5.35 (2H, m), 6.28 (1H, dd, J=2.3, 8.2 Hz), 6.36 (1H, d, J=2.3 Hz), 6.85 (1H, d, J=8.2 Hz), 7.00-7.10 (4H, m)

REFERENCE EXAMPLE 78

4-(4-Ethylbenzyl)-3-hydroxybenzamide

To a mixture of methyl 4-(4-ethylbenzyl)-3-hydroxybenzoate (0.20 g) and 28% aqueous ammonia solution (6 mL) in ethanol (3 mL) was added ammonium chloride (0.079 g), and the mixture was stirred at 100° C. in a sealed tube for 14 hours. The reaction mixture was concentrated, and water was added to the residue. The mixture was extracted with ethyl acetate, and the organic layer was dried over anhydrous magnesium sulfate. The solvent was removed under reduced pressure, and to the residue was added a mixture (10/1) of dichloromethane and methanol. Insoluble materials were collected and dried to give 4-(4-ethylbenzyl)-3-hydroxybenzamide (0.065 g).

$^1$H-NMR (DMSO-d$_6$) δ ppm:
1.14 (3H, t, J=7.6 Hz), 2.54 (2H, q, J=7.6 Hz), 3.85 (2H, s), 7.00-7.15 (6H, m), 7.21 (1H, dd, J=1.7, 7.8 Hz), 7.29 (1H, d, J=1.7 Hz), 7.72 (1H, brs), 9.56 (1H, s)

REFERENCE EXAMPLE 79

5-Carbamoyl-2-(4-ethylbenzyl)phenyl 2,3,4,6-tetra-O-acetyl-β-D-glucopyranoside The title compound was prepared in a similar manner to that described in Reference Example 61 using 4-(4-ethylbenzyl)-3-hydroxybenzamide instead of 5-methoxy-2-{4-[2-(methoxymethyloxy)ethyl]benzyl}phenol.

$^1$H-NMR (CD$_3$OD) δ ppm:
1.19 (3H, t, J=7.6 Hz), 1.85 (3H, s), 1.99 (3H, s), 2.04 (6H, s), 2.56 (2H, q, J=7.6 Hz), 3.80-4.00 (2H, m), 4.00-4.35 (3H, m), 5.05-5.20 (1H, m), 5.20-5.30 (1H, m), 5.30-5.45 (2H, m), 6.95-7.20 (5H, m), 7.40-7.55 (1H, m), 7.55-7.65 (1H, m)

REFERENCE EXAMPLE 80

2-Hydroxy-4-(methoxymethyloxy)benzaldehyde

To a suspension of 2,4-dihydroxybenzaldehyde (0.83 g) and cesium carbonate (1.7 g) in acetonitrile (30 mL) was added chloromethyl methyl ether (0.55 mL), and the mixture was stirred at room temperature for 30 minutes. Water was added to the reaction mixture, and the mixture was extracted with ethyl acetate. The organic layer was dried over anhydrous sodium sulfate, and the solvent was removed under reduced pressure. The residue was purified by column chromatography on silica gel (eluent: hexane/ethyl acetate=4/1) to give 2-hydroxy-4-(methoxymethyloxy)benzaldehyde (0.84 g).

$^1$H-NMR (CDCl$_3$) δ ppm:

3.48 (3H, s), 5.22 (2H, s), 6.60 (1H, d, J=2.2 Hz), 6.65 (1H, dd, J=2.2, 8.6 Hz), 7.45 (1H, d, J=8.6 Hz), 9.74 (1H, s), 11.37 (1H, s)

REFERENCE EXAMPLE 81

4'-Ethyl-2-hydroxy-4-(methoxymethyloxy)diphenylmethanol

To a solution of 1-bromo-4-ethylbenzene (0.46 g) in tetrahydrofuran (12 mL) was added tert-butyllithium (1.45 mol/L pentane solution, 1.9 mL) under an argon atmosphere at −78° C., and the mixture was stirred for 30 minutes. A solution of 2-hydroxy-4-methoxymethyloxybenzaldehyde (0.18 g) in tetrahydrofuran (6 mL) was added to the reaction mixture, and after warming to 0° C. the mixture was stirred for 15 minutes. A saturated aqueous ammonium chloride solution was added to the reaction mixture, and the mixture was extracted with diethyl ether. The organic layer was dried over anhydrous sodium sulfate, and the solvent was removed under reduced pressure. The residue was purified by column chromatography on silica gel (eluent: hexane/ethyl acetate=3/1) to give 4'-ethyl-2-hydroxy-4-(methoxymethyloxy)diphenylmethanol (0.30 g).

$^1$H-NMR (CDCl$_3$) δ ppm:

1.23 (3H, t, J=7.5 Hz), 2.64 (2H, q, J=7.5 Hz), 2.80 (1H, d, J=3.1 Hz), 3.45 (3H, s), 5.12 (2H, s), 5.95 (1H, d, J=3.1 Hz), 6.47 (1H, dd, J=2.5, 8.5 Hz), 6.61 (1H, d, J=2.5 Hz), 6.72 (1H, d, 8.5 Hz), 7.15-7.25 (2H, m), 7.25-7.35 (2H, m), 8.07 (1H, s)

REFERENCE EXAMPLE 82

2-(4-Ethylbenzyl)-5-(methoxymethyloxy)phenol

To a solution of 4'-ethyl-2-hydroxy-4-(methoxymethyloxy)diphenylmethanol (0.14 g) in ethanol (5 mL) was added 10% palladium-carbon powder (0.058 g), and the mixture was stirred under a hydrogen atmosphere at room temperature for 1 hour. Insoluble materials were removed by filtration, and the solvent of the filtrate was removed under reduced pressure. The residue was purified by column chromatography on silica gel (eluent: hexane/ethyl acetate=4/1) to give 2-(4-ethylbenzyl)-5-(methoxymethyloxy)phenol (0.12 g).

$^1$H-NMR (CDCl$_3$) δ ppm:

1.21 (3H, t, J=7.6 Hz), 2.61 (2H, q, J=7.6 Hz), 3.47 (3H, s), 3.90 (2H, s), 4.73 (1H, s), 5.13 (2H, s), 6.53 (1H, d, J=2.2 Hz), 6.58 (1H, dd, J=2.2, 8.1 Hz), 7.02 (1H, d, J=8.1 Hz), 7.10-7.15 (4H, m)

REFERENCE EXAMPLE 83

2-(4-Ethylbenzyl)-5-(methoxymethyloxy)phenyl 2,3,4,6-tetra-O-acetyl-β-D-glucopyranoside The title compound was prepared in a similar manner to that described in Reference Example 61 using 2-(4-ethylbenzyl)-5-(methoxymethyloxy)phenol instead of 5-methoxy-2-{4-[2-(methoxymethyloxy)ethyl]benzyl}phenol.

$^1$H-NMR (CDCl$_3$) δ ppm:

1.19 (3H, t, J=7.6 Hz), 1.85 (3H, s), 2.02 (3H, s), 2.05 (3H, s), 2.10 (3H, s), 2.59 (2H, q, J=7.6 Hz), 3.46 (3H, s), 3.79 (1H, d, J=15.5 Hz), 3.84 (1H, d, J=15.5 Hz), 3.85-3.95 (1H, m), 4.19 (1H, dd, J=2.3, 12.2 Hz), 4.27 (1H, dd, J=5.5, 12.2 Hz), 5.05-5.25 (4H, m), 5.25-5.40 (2H, m), 6.69 (1H, dd, J=2.4, 8.4 Hz), 6.68 (1H, d, J=2.4 Hz), 6.96 (1H, d, J=8.4 Hz), 7.00-7.15 (4H, m)

REFERENCE EXAMPLE 84

2-(4-Methoxybenzyl)-3,5-dimethylphenol

To 3,5-dimethylphenol (12 g) were added lithium hydroxide monohydrate (4.2 g) and 4-methoxybenzyl chloride (14 mL) at 85° C., and the mixture was stirred for 1.5 hours. The reaction mixture was cooled to room temperature and purified by column chromatography on silica gel (eluent: dichloromethene) to give 2-(4-methoxybenzyl)-3,5-dimethylphenol (5.1 g).

$^1$H-NMR (CDCl$_3$) δ ppm:

2.24 (3H, s), 2.26 (3H, s), 3.77 (3H, s), 3.94 (2H, s), 4.53 (1H, s), 6.45-6.55 (1H, m), 6.55-6.65 (1H, m), 6.75-6.85 (2H, m), 7.00-7.10 (2H, m)

REFERENCE EXAMPLE 85

2-(4-Methoxybenzyl)-3,5-dimethylphenyl 2,3,4,6-tetra-O-acetyl-β-D-glucopyranoside To a solution of 2-(4-methoxybenzyl)-3,5-dimethylphenol (4.0 g) and 2,3,4,6-tetra-O-acetyl-1-O-trichloroacetoimidoyl-α-D-glucopyranose (8.9 g) in dichloromethane (100 mL) was added boron trifluoride diethyl ether complex (2.5 mL) at 0° C., and the mixture was stirred at room temperature for 1 hour. The reaction mixture was purified by column chromatography on aminopropyl silica gel (eluent: dichloromethane). The solvent was removed under reduced pressure, and to the residue was added ethanol. The resulting precipitates were collected by filtration and dried under reduced pressure to give 2-(4-methoxybenzyl)-3,5-dimethylphenyl 2,3,4,6-tetra-O-acetyl-β-D-glucopyranoside (7.8 g).

$^1$H-NMR (CDCl$_3$) δ ppm:

1.65 (3H, s), 2.00 (3H, s), 2.04 (3H, s), 2.09 (3H, s), 2.12 (3H, s), 2.30 (3H, s), 3.74 (3H, s), 3.78 (1H, d, J=15.5 Hz), 3.80-3.95 (1H, m), 4.00 (1H, d, J=15.5 Hz), 4.18 (1H, dd, J=2.5, 12.2 Hz), 4.24 (1H, dd, J=5.8, 12.2 Hz), 5.00-5.20 (2H, m), 5.20-5.35 (2H, m), 6.70-6.80 (4H, m), 6.85-7.00 (2H, m)

REFERENCE EXAMPLE 86

3-Hydroxy-4-(4-methoxybenzyl)benzamide

The title compound was prepared in a similar manner to that described in Reference Example 78 using methyl 3-hydroxy-4-(4-methoxybenzyl)benzoate instead of methyl 4-(4-ethylbenzyl)-3-hydroxybenzoate. Purification was performed by column chromatography on silica gel (eluent: dichloromethane/methanol=8/1).

$^1$H-NMR (CD$_3$OD) δ ppm:

3.74 (3H, s), 3.89 (2H, s), 6.75-6.85 (2H, m), 7.03 (1H, d, J=7.8 Hz), 7.05-7.15 (2H, m), 7.21 (1H, dd, J=1.6, 7.8 Hz), 7.27 (1H, d, J=1.6 Hz)

REFERENCE EXAMPLE 87

3-Hydroxy-4-(4-methoxybenzyl)benzonitrile

To a solution of 3-hydroxy-4-(4-methoxybenzyl)benzamide (0.047 g) and triethylamine (0.30 mL) in dichloromethane (1.8 mL) was added trifluoromethanesulfonic anhydride (0.34 mL), and the mixture was stirred at room temperature overnight. To the reaction mixture was added water, and the mixture was extracted with ethyl acetate. The organic layer was dried over anhydrous sodium sulfate, and the solvent was removed under reduced pressure. The residue was purified by preparative thin layer chromatography on silica gel (eluent: dichloromethane/methanol=9/1) to give 3-hydroxy-4-(4-methoxybenzyl)benzonitrile (0.014 g).

$^1$H-NMR (CDCl$_3$) δ ppm:
3.80 (3H, s), 4.06 (2H, s), 6.80-6.90 (2H, m), 7.05-7.15 (2H, m), 7.25 (1H, d, J=8.0 Hz), 7.66 (1H, dd, J=1.6, 8.0 Hz), 7.76 (1H, d, J=1.6 Hz)

REFERENCE EXAMPLE 88

5-Cyano-2-(4-methoxybenzyl)phenyl 2,3,4,6-tetra-O-acetyl-β-D-glucopyranoside

The title compound was prepared in a similar manner to that described in Reference Example 61 using 3-hydroxy-4-(4-methoxybenzyl)benzonitrile instead of 5-methoxy-2-{4-[2-(methoxymethyloxy)ethyl]benzyl}phenol.

$^1$H-NMR (CDCl$_3$) δ ppm:
1.93 (3H, s), 2.04 (3H, s), 2.07 (3H, s), 2.14 (3H, s), 3.78 (3H, s), 3.87 (2H, s), 3.90-4.00 (1H, m), 4.15-4.30 (2H, m), 5.05-5.20 (2H, m), 5.25-5.45 (2H, m), 6.75-6.90 (2H, m), 6.95-7.10 (2H, m), 7.10-7.20 (1H, m), 7.20-7.35 (2H, m)

REFERENCE EXAMPLE 89

2-Hydroxy-4,4'-dimethoxydiphenylmethanol

The title compound was prepared in a similar manner to that described in Reference Example 59 using 4-bromoanisole instead of 4-[2-(methoxymethyloxy)ethyl]bromobenzene.

$^1$H-NMR (CDCl$_3$) δ ppm:
2.66 (1H, d, J=3.0 Hz), 3.77 (3H, s), 3.81 (3H, s), 5.95 (1H, d, J=3.0 Hz), 6.36 (1H, dd, J=2.6, 8.5 Hz), 6.49 (1H, d, J=2.6 Hz), 6.69 (1H, d, J=8.5 Hz), 6.85-6.95 (2H, m), 7.25-7.35 (2H, m), 8.10 (1H, s)

REFERENCE EXAMPLE 90

5-Methoxy-2-(4-methoxybenzyl)phenol

The title compound was prepared in a similar manner to that described in Reference Example 60 using 2-hydroxy-4,4'-dimethoxydiphenylmethanol instead of 2-hydroxy-4-methoxy-4'-[2-(methoxymethyloxy)ethyl]diphenylmethanol.

$^1$H-NMR (CDCl$_3$) δ ppm:
3.77 (3H, s), 3.78 (3H, s), 3.87 (2H, s), 4.67 (1H, s), 6.39 (1H, d, J=2.5 Hz), 6.46 (1H, dd, J=2.5, 8.3 Hz), 6.75-6.90 (2H, m), 7.01 (1H, d, J=8.3 Hz), 7.05-7.20 (2H, m)

REFERENCE EXAMPLE 91

5-Methoxy-2-(4-methoxybenzyl)phenyl 2,3,4,6-tetra-O-acetyl-β-D-glucopyranoside

The title compound was prepared in a similar manner to that described in Reference Example 61 using 5-methoxy-2-(4-methoxybenzyl)phenol instead of 5-methoxy-2-{4-[2-(methoxymethyloxy)ethyl]benzyl}phenol.

$^1$H-NMR (CDCl$_3$) δ ppm:
1.88 (3H, s), 2.02 (3H, s), 2.05 (3H, s), 2.09 (3H, s), 3.70-3.95 (9H, m), 4.19 (1H, dd, J=2.5, 12.2 Hz), 4.25 (1H, dd, J=5.9, 12.2 Hz), 5.07 (1H, d, J=7.4 Hz), 5.10-5.40 (3H, m), 6.54 (1H, dd, J=2.4, 8.4 Hz), 6.65 (1H, d, J=2.4 Hz), 6.75-6.85 (2H, m), 6.94 (1H, d, J=8.4 Hz), 7.00-7.10 (2H, m)

REFERENCE EXAMPLE 92

3-Benzyloxy-4-(4-ethylbenzyl)benzyl Alcohol

To a solution of methyl 4-(4-ethylbenzyl)-3-hydroxybenzoate (1.3 g) in N,N-dimethylformamide (15 mL) were added potassium carbonate (0.79 g) and benzyl bromide (0.62 mL), and the mixture was stirred at room temperature for 13 hours. To the reaction mixture was added water, and the mixture was extracted with diethyl ether. The organic layer was washed with water and dried over anhydrous magnesium sulfate, and the solvent was removed under reduced pressure. The residue was dissolved in diethyl ether (10 mL), and the solution was added to a suspension of lithium aluminum hydride (0.57 g) in diethyl ether (50 mL) at 0° C. The mixture was heated under reflux for 1.5 hours. After cooling to 0° C., to the reaction mixture was successively added water (0.60 mL), 15% aqueous sodium hydroxide solution (0.60 mL) and water (1.8 mL), and the mixture was stirred for 5 minutes. Insoluble materials were removed by filtration, and the solvent of the filtrate was removed under reduced pressure. The residue was purified by column chromatography on silica gel (eluent: hexane/ethyl acetate=2/1) to give 3-benzyloxy-4-(4-ethylbenzyl)benzyl alcohol (1.3 g).

$^1$H-NMR (CDCl$_3$) δ ppm:
1.22 (3H, t, J=7.7 Hz), 1.57 (1H, t, J=6.2 Hz), 2.61 (2H, q, J=7.7 Hz), 3.98 (2H, s), 4.65 (2H, d, J=6.2 Hz), 5.07 (2H, s), 6.87 (1H, dd, J=1.1, 7.5 Hz), 6.97 (1H, d, J=1.1 Hz), 7.05-7.15 (5H, m), 7.25-7.40 (5H, m)

REFERENCE EXAMPLE 93

[3-Benzyloxy-4-(4-ethylbenzyl)phenyl]acetonitrile

To a solution of 3-benzyloxy-4-(4-ethylbenzyl)benzyl alcohol (0.87 g) in dichloromethane (20 mL) were added triethylamine (0.44 mL) and methanesulfonyl chloride (0.22 mL) at 0° C., and the mixture was stirred for 2 hours. To the reaction mixture was added 0.5 mol/L hydrochloric acid, and the mixture was extracted with diethyl ether. The organic layer was washed with water and a saturated aqueous sodium hydrogen carbonate, and dried over anhydrous magnesium sulfate, and the solvent was removed under reduced pressure. The residue was dissolved in dimethylsulfoxide (10 mL), and potassium cyanide (0.68 g) and a catalytic amount of sodium iodide were added to the solution. The mixture was stirred at 80° C. for 12 hours. To the reaction mixture was added water, and the mixture was extracted with diethylether. The organic layer was washed with water and dried over anhydrous magnesium sulfate, and the solvent was removed under reduced pressure. The residue was purified by column chromatography on silica gel (eluent: hexane/ethyl acetate=5/1-3/1) to give [3-benzyloxy-4-(4-ethylbenzyl)phenyl]-acetonitrile (0.41 g).

$^1$H-NMR (CDCl$_3$) δ ppm:

1.22 (3H, t, J=7.5 Hz), 2.61 (2H, q, J=7.5 Hz), 3.70 (2H, s), 3.97 (2H, s), 5.07 (2H, s), 6.80-6.90 (2H, m), 7.05-7.15 (5H, m), 7.25-7.45 (5H, m)

REFERENCE EXAMPLE 94

2-[3-Benzyloxy-4-(4-ethylbenzyl)phenyl]acetoamide

To a mixture of [3-benzyloxy-4-(4-ethylbenzyl)-phenyl]acetonitrile (0.41 g) in ethanol (5 mL) and water (10 mL) was added potassium hydroxide (0.68 g), and the mixture was heated under reflux for 4 hours. To the reaction mixture was added 2 mol/L hydrochloric acid to acidify, and the mixture was extracted with diethyl ether. The organic layer was washed with water and dried over anhydrous magnesium sulfate, and the solvent was removed under reduced pressure to give [3-benzyloxy-4-(4-ethylbenzyl)phenyl]acetic acid (0.41 g). To a solution of the obtained [3-benzyloxy-4-(4-ethylbenzyl)phenyl]acetic acid (0.41 g) in tetrahydrofuran (10 mL) were added pyridine (0.19 mL), di-tert-butylcarbonate (0.50 g) and ammonium hydrogen carbonate (0.18 g), and the mixture was stirred at room temperature for 18 hours. To the reaction mixture was added 1 mol/L hydrochloric acid, and the mixture was extracted with ethylacetate. The organic layer was washed with water and dried over anhydrous magnesium sulfate, and the solvent was removed under reduced pressure. The residue was purified by column chromatography on silica gel (eluent: dichloromethane/methanol=10/1) to give 2-[3-benzyloxy-4-(4-ethylbenzyl)phenyl]-acetoamide (0.38 g).

$^1$H-NMR (DMSO-$d_6$) δ ppm:
1.14 (3H, t, J=7.5 Hz), 2.53 (2H, q, J=7.5 Hz), 3.25-3.40 (2H, m), 3.85 (2H, s), 5.06 (2H, s), 6.78 (1H, dd, J=1.0, 7.9 Hz), 6.84 (1H, brs), 6.98 (1H, d, J=1.0 Hz), 7.00-7.10 (5H, m), 7.25-7.45 (6H, m)

REFERENCE EXAMPLE 95

2-[4-(4-Ethylbenzyl)-3-hydroxyphenyl]acetoamide

To a solution of 2-[3-benzyloxy-4-(4-ethylbenzyl)-phenyl]acetoamide (0.38 g) in methanol (5 mL) was added 10% palladium-carbon powder (0.075 g), and the mixture was stirred under a hydrogen atmosphere at room temperature for 4 hours. Insoluble materials were removed by filtration, and the solvent of the filtrate was removed under reduced pressure. The residue was purified by column chromatography on silica gel (eluent: dichloromethane/methanol=30/1-20/1) to give 2-[4-(4-ethylbenzyl)-3-hydroxyphenyl]acetoamide (0.16 g).

$^1$H-NMR (DMSO-$d_6$) δ ppm:
1.13 (3H, t, J=7.6 Hz), 2.53 (2H, q, J=7.6 Hz), 3.22 (2H, s), 3.77 (2H, s), 6.59 (1H, dd, J=1.5, 7.7 Hz), 6.72 (1H, d, J=1.5 Hz), 6.81 (1H, brs), 6.90 (1H, d, J=7.7 Hz), 7.00-7.15 (4H, m), 7.37 (1H, brs), 9.27 (1H, s)

REFERENCE EXAMPLE 96

5-Carbamoylmethyl-2-(4-ethylbenzyl)phenyl 2,3,4,6-tetra-O-acetyl-β-D-glucopyranoside The title compound was prepared in a similar manner to that described in Reference Example 61 using 2-[4-(4-ethylbenzyl)-3-hydroxyphenyl]acetoamide instead of 5-methoxy-2-{4-[2-(methoxymethyloxy)ethyl]benzyl}phenol.

$^1$H-NMR (CDCl$_3$) δ ppm:
1.20 (3H, t, J=7.6 Hz), 1.88 (3H, s), 2.03 (3H, s), 2.06 (3H, s), 2.07 (3H, s), 2.60 (2H, q, J=7.6 Hz), 3.53 (2H, s), 3.80-3.95 (3H, m), 4.15-4.30 (2H, m), 5.13 (1H, d, J=7.1 Hz), 5.15-5.25 (1H, m), 5.25-5.40 (3H, m), 5.48 (1H, brs), 6.91 (1H, dd, J=1.4, 7.9 Hz), 6.97 (1H, d, J=1.4 Hz), 7.00-7.15 (5H, m)

REFERENCE EXAMPLE 97

2-Hydroxy-4'-methoxy-4-(methoxymethyl)diphenylmethanol

The title compound was prepared in a similar manner to that described in Reference Example 59 using 4-bromoanisole instead of 4-[2-(methoxymethyloxy)ethyl]bromobenzene, and 2-hydroxy-4-methoxymethylbenzaldehyde instead of 2-hydroxy-4-methoxybenzaldehyde, respectively.

$^1$H-NMR (CDCl$_3$) δ ppm:
2.71 (1H, d, J=3.1 Hz), 3.37 (3H, s), 3.80 (3H, s), 4.39 (2H, s), 5.99 (1H, d, J=3.1 Hz), 6.70-6.85 (2H, m), 6.85-6.95 (3H, m), 7.25-7.35 (2H, m), 7.98 (1H, s)

REFERENCE EXAMPLE 98

2-(4-Methoxybenzyl)-5-methoxymethylphenol

To a solution of 2-hydroxy-4'-methoxy-4-(methoxymethyl)-diphenylmethanol (0.17 g) in ethanol (11 mL) was added 10% palladium-carbon powder (0.051 g), and the mixture was stirred under a hydrogen atmosphere at room temperature for 30 minutes. Insoluble materials were removed by filtration, and the solvent of the filtrate was removed under reduced pressure. The residue was purified by column chromatography on silica gel (eluent: hexane/ethyl acetate=3/1-2/1) to give 2-(4-methoxybenzyl)-5-methoxymethylphenol (0.082 g).

$^1$H-NMR (CDCl$_3$) δ ppm:
3.38 (3H, s), 3.78 (3H, s), 3.92 (2H, s), 4.39 (2H, s), 4.77 (1H, s), 6.75-6.90 (4H, m), 7.00-7.20 (3H, m)

REFERENCE EXAMPLE 99

2-(4-Methoxybenzyl)-5-methoxymethylphenyl 2,3,4,6-tetra-O-acetyl-β-D-glucopyranoside The title compound was prepared in a similar manner to that described in Reference Example 61 using 2-(4-methoxybenzyl)-5-methoxymethylphenol instead of 5-methoxy-2-{4-[2-(methoxymethyloxy)ethyl]benzyl}phenol.

$^1$H-NMR (CDCl$_3$) δ ppm:
1.90 (3H, s), 2.03 (3H, s), 2.05 (3H, s), 2.08 (3H, s), 3.37 (3H, s), 3.77 (3H, s), 3.84 (2H, s), 3.85-3.95 (1H, m), 4.10-4.30 (2H, m), 4.30-4.50 (2H, m), 5.10-5.25 (2H, m), 5.25-5.40 (2H, m), 6.75-6.85 (2H, m), 6.90-7.10 (5H, m)

REFERENCE EXAMPLE 100

5-Methoxy-2-{4-[2-(methoxymethyloxy)ethyl]benzyl}phenyl β-D-glucopyranoside

To a solution of 5-methoxy-2-{4-[2-(methoxymethyloxy)ethyl]benzyl}phenyl 2,3,4,6-tetra-O-acetyl-β-D-glucopyranoside (0.13 g) in methanol (8 mL) was added 2 mol/L sodium hydroxide (0.50 mL), and the mixture was stirred at room temperature for 25 minutes. The solvent was removed under reduced pressure, and the residue was purified by preparative thin layer chromatography on silica gel (eluent:

dichloromethane/methanol=7/1) to give 5-methoxy-2-{4-[2-(methoxymethyloxy)ethyl]benzyl}phenyl β-D-glucopyranoside (0.053 g).

$^1$H-NMR (CD$_3$OD) δ ppm:
2.81 (2H, t, J=6.9 Hz), 3.24 (3H, s), 3.30-3.55 (4H, m), 3.60-3.75 (3H, m), 3.75 (3H, s), 3.88 (1H, d, J=15.0 Hz), 3.90 (1H, dd, J=2.0, 12.0 Hz), 4.00 (1H, d, J=15.0 Hz), 4.57 (2H, s), 4.85-4.95 (1H, m), 6.50 (1H, dd, J=2.5, 8.3 Hz), 6.79 (1H, d, J=2.5 Hz), 6.93 (1H, d, J=8.3 Hz), 7.05-7.20 (4H, m)

REFERENCE EXAMPLE 101

5-[2-(Benzyloxy)ethyloxy]-2-(4-ethylbenzyl)phenyl β-D-glucopyranoside

To a suspension of 2-(4-ethylbenzyl)-5-hydroxyphenyl β-D-glucopyranoside (0.039 g) and cesium carbonate (0.098 g) in N,N-dimethylformamide (1 mL) was added (2-bromoethyl)benzyl ether (0.025 mL), and the mixture was stirred at 50° C. for 3.5 hours. After cooling to room temperature, to the reaction mixture was added water, and the mixture was extracted with ethyl acetate. The organic layer was dried over anhydrous sodium sulfate, and the solvent was removed under reduced pressure. The residue was purified by preparative thin layer chromatography on silica gel (eluent: dichloromethane/methanol=6/1) to give 5-[2-(benzyloxy)ethyloxy]-2-(4-ethylbenzyl)phenyl β-D-glucopyranoside (0.022 g).

$^1$H-NMR (CD$_3$OD) δ ppm:
1.18 (3H, t, J=7.6 Hz), 2.57 (2H, q, J=7.6 Hz), 3.30-3.55 (4H, m), 3.67 (1H, dd, J=5.4, 12.1 Hz), 3.75-3.85 (2H, m), 3.86 (1H, d, J=15.0 Hz), 3.88 (1H, dd, J=2.0, 12.1 Hz), 3.98 (1H, d, J=15.0 Hz), 4.05-4.15 (2H, m), 4.58 (2H, s), 4.80-4.90 (1H, m), 6.52 (1H, dd, J=2.4, 8.5 Hz), 6.81 (1H, d, J=2.4 Hz), 6.93 (1H, d, J=8.5 Hz), 7.00-7.20 (4H, m), 7.20-7.40 (5H, m)

REFERENCE EXAMPLE 102

2-[4-(2-Hydroxyethyl)benzyl]-5-methoxyphenyl β-D-glucopyranoside

To a solution of 5-methoxy-2-(4-[2-(methoxymethyloxy)ethyl]benzyl)phenyl β-D-glucopyranoside (0.053 g) in methanol (2.3 mL) was added p-toluenesulfonic acid monohydrate (0.032 g), and the mixture was stirred at 50° C. for 3 hours. After cooling to room temperature, to the reaction mixture was added triethylamine (0.5 mL), and the solvent was removed under reduced pressure. The residue was purified by preparative thin layer chromatography on silica gel (eluent: dichloromethane/methanol=6/1) to give 2-[4-(2-hydroxyethyl)-benzyl]-5-methoxyphenyl β-D-glucopyranoside (0.023 g).

$^1$H-NMR (CD$_3$OD) δ ppm:
2.76 (2H, t, J=7.0 Hz), 3.30-3.55 (4H, m), 3.60-3.75 (3H, m), 3.75 (3H, s), 3.87 (1H, d, J=15.0 Hz), 3.89 (1H, dd, J=1.9, 12.2 Hz), 3.99 (1H, d, J=15.0 Hz), 4.85-4.95 (1H, m), 6.50 (1H, dd, J=2.5, 8.3 Hz), 6.78 (1H, d, J=2.5 Hz), 6.94 (1H, d, J=8.3 Hz), 7.05-7.20 (4H, m)

REFERENCE EXAMPLE 103

5-Amino-2-(4-ethylbenzyl)phenyl β-D-glucopyranoside

To a solution of 5-amino-2-(4-ethylbenzyl)phenyl 2,3,4,6-tetra-O-acetyl-β-D-glucopyranoside (0.19 g) in methanol (3.5 mL) was added sodium methoxide (28% methanol solution; 0.064 mL), and the mixture was stirred at room temperature for 50 minutes. The reaction mixture was concentrated under reduced pressure, and to the residue was added water. Precipitated crystals were collected by filtration, washed with water and dried to give 5-amino-2-(4-ethylbenzyl)-phenyl β-D-glucopyranoside (0.12 g).

$^1$H-NMR (CD$_3$OD) δ ppm:
1.18 (3H, t, J=7.7 Hz), 2.57 (2H, q, J=7.7 Hz), 3.30-3.50 (4H, m), 3.69 (1H, dd, J=5.4, 12.0 Hz), 3.81 (1H, d, J=15.0 Hz), 3.90 (1H, dd, J=2.1, 12.0 Hz), 3.92 (1H, d, J=15.0 Hz), 4.80-4.95 (1H, m), 6.33 (1H, dd, J=2.2, 8.1 Hz), 6.59 (1H, d, J=2.2 Hz), 6.78 (1H, d, J=8.1 Hz), 7.00-7.15 (4H, m)

REFERENCE EXAMPLE 104

2-[4-(3-Hydroxypropyl)benzyl]-3,5-dimethylphenyl β-D-glucopyranoside

To a solution of 2-[4-(3-benzoyloxypropyl)benzyl]-3,5-dimethylphenol (0.72 g) and 1,2,3,4,6-penta-O-acetyl-β-D-glucopyranose (2.3 g) in toluene (7 mL) and dichloromethane (3 mL) was added boron trifluoride diethyl ether complex (0.73 mL), and the mixture was stirred at room temperature for 10 hours. To the reaction mixture were added ethyl acetate and a saturated aqueous sodium hydrogen carbonate solution, and the organic layer was separated. The organic layer was washed with brine and dried over anhydrous sodium sulfate, and the solvent was removed under reduced pressure. The residue was dissolved in methanol (6 mL) and tetrahydrofuran (4 mL), sodium methoxide (28% methanol solution, 0.19 mL) was added to the solution, and the mixture was stirred at 30° C. for 7.5 hours. To the reaction mixture were added ethyl acetate and water, and the organic layer was separated. The organic layer was washed with brine and dried over anhydrous sodium sulfate, and the solvent was removed under reduced pressure. The residue was dissolved in methanol (10 mL), sodium methoxide (28% methanol solution, 0.075 mL) was added to the solution, and the mixture was stirred at 30° C. for 14 hours. The reaction mixture was purified by column chromatography on silica gel (eluent: dichloromethane/methanol=8/1). The solvent was removed under reduced pressure, diethyl ether was added to the residue, and the resulting precipitates were collected by filtration. The obtained solid was washed with diethyl ether and dried under reduced pressure to give 2-[4-(3-hydroxypropyl)-benzyl]-3,5-dimethylphenyl β-D-glucopyranoside (0.58 g).

$^1$H-NMR (CD$_3$OD) δ ppm:
1.70-1.85 (2H, m), 2.13 (3H, s), 2.27 (3H, s), 2.55-2.65 (2H, m), 3.30-3.45 (4H, m), 3.45-3.60 (2H, m), 3.68 (1H, dd, J=5.3, 11.9 Hz), 3.87 (1H, dd, J=2.3, 11.9 Hz), 3.95 (1H, d, J=15.5 Hz), 4.15 (1H, d, J=15.5 Hz), 4.80-4.90 (1H, m), 6.65-6.70 (1H, m), 6.85-6.95 (1H, m), 6.95-7.10 (4H, m)

REFERENCE EXAMPLE 105

2-[4-(2-Hydroxyethyl)benzyl]-3,5-dimethylphenyl β-D-glucopyranoside

The title compound was prepared in a similar manner to that described in Reference Example 104 using 2-[4-(2-benzoyloxyethyl)benzyl]-3,5-dimethylphenol instead of 2-[4-(3-benzoyloxypropyl)benzyl]-3,5-dimethylphenol.

$^1$H-NMR (CD$_3$OD) δ ppm:
2.13 (3H, s), 2.27 (3H, s), 2.74 (2H, t, J=7.0 Hz), 3.30-3.45 (4H, m), 3.60-3.75 (3H, m), 3.86 (1H, dd, J=2.3, 11.9 Hz), 3.95 (1H, d, J=15.4 Hz), 4.16 (1H, d, J=15.4 Hz), 4.80-4.90 (1H, m), 6.65-6.70 (1H, m), 6.85-6.95 (1H, m), 7.00-7.10 (4H, m)

REFERENCE EXAMPLE 106

2-(4-Ethylbenzyl)-5-methylaminophenyl β-D-glucopyranoside

The title compound was prepared in a similar manner to that described in Reference Example 103 using 2-(4-ethylbenzyl)-5-methylaminophenyl 2,3,4,6-tetra-O-acetyl-β-D-glucopyranoside instead of 5-amino-2-(4-ethylbenzyl)phenyl 2,3,4,6-tetra-O-acetyl-β-D-glucopyranoside.

$^1$H-NMR (CD$_3$OD) δ ppm:
1.18 (3H, t, J=7.6 Hz), 2.57 (2H, q, J=7.6 Hz), 2.73 (3H, s), 3.30-3.55 (4H, m), 3.68 (1H, dd, J=5.7, 12.1 Hz), 3.75-4.00 (3H, m), 4.80-4.90 (1H, m), 6.25 (1H, dd, J=2.2, 8.2 Hz), 6.51 (1H, d, J=2.2 Hz), 6.81 (1H, d, J=8.2 Hz), 7.00-7.15 (4H, m)

REFERENCE EXAMPLE 107

5-Carbamoyl-2-(4-ethylbenzyl)phenyl β-D-glucopyranoside

To a solution of 5-carbamoyl-2-(4-ethylbenzyl)phenyl 2,3,4,6-tetra-O-acetyl-β-D-glucopyranoside (0.13 g) in methanol (3 mL) was added sodium methoxide (28% methanol solution; 0.043 mL), and the mixture was stirred at room temperature for 30 minutes. The reaction mixture was purified by column chromatography on (benzenesulfonylpropyl) silica gel (eluent: methanol). To the obtained compound was added diethyl ether, and the resulting precipitates were collected by filtration and dried under reduced pressure to give 5-carbamoyl-2-(4-ethylbenzyl)phenyl β-D-glucopyranoside (0.079 g).

$^1$H-NMR (CD$_3$OD) δ ppm:
1.19 (3H, t, J=7.6 Hz), 2.59 (2H, q, J=7.6 Hz), 3.30-3.60 (4H, m), 3.70 (1H, dd, J=7.2, 12.1 Hz), 3.91 (1H, dd, J=2.2, 12.1 Hz), 4.00 (1H, d, J=15.0 Hz), 4.10 (1H, d, J=15.0 Hz), 5.01 (1H, d, J=7.4 Hz), 7.05-7.20 (5H, m), 7.44 (1H, dd, J=1.7, 7.9 Hz), 7.64 (1H, d, J=1.7 Hz)

REFERENCE EXAMPLE 108

2-(4-Ethylbenzyl)-5-(methoxymethyloxy)phenyl β-D-glucopyranoside

The title compound was prepared in a similar manner to that described in Reference Example 100 using 2-(4-ethylbenzyl)-5-(methoxymethyloxy)phenyl 2,3,4,6-tetra-O-acetyl-β-D-glucopyranoside instead of 5-methoxy-2-{4-[2-(methoxymethyloxy)ethyl]benzyl}phenyl 2,3,4,6-tetra-O-acetyl-β-D-glucopyranoside $^1$H-NMR (CD$_3$OD) δ ppm:
1.19 (3H, t, J=7.6 Hz), 2.57 (2H, q, J=7.6 Hz), 3.35-3.55 (7H, m), 3.69 (1H, dd, J=5.0, 12.2 Hz), 3.80-3.95 (2H, m), 3.98 (1H, d, J=15.3 Hz), 4.80-4.95 (1H, m), 5.05-5.20 (2H, m), 6.61 (1H, dd, J=2.4, 8.4 Hz), 6.89 (1H, d, J=2.4 Hz), 6.94 (1H, d, J=8.4 Hz), 7.00-7.20 (4H, m)

REFERENCE EXAMPLE 109

2-(4-Ethylbenzyl)-5-hydroxyphenyl β-D-glucopyranoside

The title compound was prepared in a similar manner to that described in Reference Example 102 using 2-(4-ethylbenzyl)-5-(methoxymethyloxy)phenyl β-D-glucopyranoside instead of 5-methoxy-2-(4-[2-(methoxymethyloxy)ethyl]benzyl)phenyl β-D-glucopyranoside.

$^1$H-NMR (CD$_3$OD) δ ppm:
1.18 (3H, t, J=7.6 Hz), 2.57 (2H, q, J=7.6 Hz), 3.35-3.55 (4H, m), 3.65-3.75 (1H, m), 3.83 (1H, d, J=15.1 Hz), 3.85-3.95 (1H, m), 3.94 (1H, d, J=15.1 Hz), 4.80-4.90 (1H, m), 6.37 (1H, dd, J=2.4, 8.2 Hz), 6.64 (1H, d, J=2.4 Hz), 6.84 (1H, d, J=8.2 Hz), 7.00-7.15 (4H, m)

REFERENCE EXAMPLE 110

2-(4-Ethylbenzyl)-5-(2-hydroxyethyloxy)phenyl β-D-glucopyranoside

To a solution of 5-[2-(benzyloxy)ethyloxy]-2-(4-ethylbenzyl)phenyl β-D-glucopyranoside (0.022 g) in ethanol (1 mL) was added 10% palladium-carbon powder (0.0082 g), and the mixture was stirred under a hydrogen atmosphere at room temperature for 1 hour. Insoluble materials were removed by filtration, and the solvent of the filtrate was removed under reduced pressure. The residue was purified by preparative thin layer chromatography on silica gel (eluent: dichloromethane/methanol=6/1) to give 2-(4-ethylbenzyl)-5-(2-hydroxyethyloxy)phenyl β-D-glucopyranoside (0.013 g).

$^1$H-NMR (CD$_3$OD) δ ppm:
1.18 (3H, t, J=7.6 Hz), 2.57 (2H, q, J=7.6 Hz), 3.30-3.55 (4H, m), 3.68 (1H, dd, J=5.5, 12.1 Hz), 3.80-3.95 (4H, m), 3.95-4.05 (3H, m), 4.85-4.90 (1H, m), 6.53 (1H, dd, J=2.3, 8.4 Hz), 6.81 (1H, d, J=2.3 Hz), 6.93 (1H, d, J=8.4 Hz), 7.00-7.15 (4H, m)

REFERENCE EXAMPLE 111

2-(4-Methoxybenzyl)-3,5-dimethylphenyl β-D-glucopyranoside

To a suspension of 2-(4-methoxybenzyl)-3,5-dimethylphenyl 2,3,4,6-tetra-O-acetyl-β-D-glucopyranoside (7.4 g) in ethanol (150 mL) was added 2 mol/L sodium hydroxide (65 mL), and the mixture was stirred at room temperature for 2 hours. To the reaction mixture was added water, and the mixture was extracted with ethyl acetate. The organic layer was washed brine and dried over anhydrous magnesium sulfate. The solvent was removed under reduced pressure to give 2-(4-methoxybenzyl)-3,5-dimethylphenyl β-D-glucopyranoside (5.2 g).

$^1$H-NMR (CD$_3$OD) δ ppm:
2.13 (3H, s), 2.27 (3H, s), 3.30-3.50 (4H, m), 3.60-3.75 (4H, m), 3.80-4.00 (2H, m), 4.00-4.20 (1H, m), 4.80-4.90 (1H, m), 6.60-6.80 (3H, m), 6.85-6.95 (1H, m), 7.00-7.10 (2H, m)

REFERENCE EXAMPLE 112

5-Cyano-2-(4-methoxybenzyl)phenyl β-D-glucopyranoside

The title compound was prepared in a similar manner to that described in Reference Example 100 using 5-cyano-2-(4-methoxybenzyl)phenyl 2,3,4,6-tetra-O-acetyl-β-D-glucopyranoside instead of 5-methoxy-2-{4-[2-(methoxymethyloxy)-ethyl]benzyl}phenyl 2,3,4,6-tetra-O-acetyl-β-D-glucopyranoside.

$^1$H-NMR (CD$_3$OD) δ ppm:
3.30-3.45 (1H, m), 3.45-3.60 (3H, m), 3.69 (1H, dd, J=5.9, 12.2 Hz), 3.75 (3H, s), 3.91 (1H, dd, J=2.2, 12.2 Hz), 3.98 (1H, d, J=15.1 Hz), 4.07 (1H, d, J=15.1 Hz), 4.99 (1H, d, J=7.4 Hz), 6.75-6.85 (2H, m), 7.10-7.20 (2H, m), 7.19 (1H, d, J=7.7 Hz), 7.28 (1H, dd, J=1.4, 7.7 Hz), 7.49 (1H, d, J=1.4 Hz)

REFERENCE EXAMPLE 113

5-Methoxy-2-(4-methoxybenzyl)phenyl β-D-glucopyranoside

The title compound was prepared in a similar manner to that described in Reference Example 103 using 5-methoxy-2-(4-methoxybenzyl)phenyl 2,3,4,6-tetra-O-acetyl-β-D-glucopyranoside instead of 5-amino-2-(4-ethylbenzyl)phenyl 2,3,4,6-tetra-O-acetyl-β-D-glucopyranoside.

$^1$H-NMR (CD$_3$OD) δ ppm:
3.30-3.55 (4H, m), 3.68 (1H, dd, J=5.8, 12.0 Hz), 3.74 (3H, s), 3.75 (3H, s), 3.80-4.00 (3H, m), 4.80-4.95 (1H, m), 6.50 (1H, dd, J=2.4, 8.4 Hz), 6.70-6.85 (3H, m), 6.93 (1H, d, J=8.4 Hz), 7.05-7.20 (2H, m)

REFERENCE EXAMPLE 114

5-Carbamoyl-2-(4-ethylbenzyl)phenyl β-D-glucopyranoside

The title compound was prepared in a similar manner to that described in Reference Example 107 using 5-carbamoylmethyl-2-(4-ethylbenzyl)phenyl 2,3,4,6-tetra-O-acetyl-β-D-glucopyranoside instead of 5-carbamoyl-2-(4-ethylbenzyl)phenyl 2,3,4,6-tetra-O-acetyl-β-D-glucopyranoside.

$^1$H-NMR (CD$_3$OD) δ ppm:
1.18 (3H, t, J=7.5 Hz), 2.57 (2H, q, J=7.5 Hz), 3.30-3.55 (6H, m), 3.69 (1H, dd, J=5.7, 12.2 Hz), 3.90 (1H, dd, J=2.2, 12.2 Hz), 3.92 (1H, d, J=14.6 Hz), 4.03 (1H, d, J=14.6 Hz), 4.93 (1H, d, J=7.6 Hz), 6.87 (1H, dd, J=1.4, 7.6 Hz), 7.00 (1H, d, J=7.6 Hz), 7.00-7.20 (5H, m)

REFERENCE EXAMPLE 115

5-[3-(Ethoxycarbonyl)propyloxy]-2-(4-ethylbenzyl)phenyl β-D-glucopyranoside

To a suspension of 2-(4-ethylbenzyl)-5-hydroxyphenyl β-D-glucopyranoside (0.051 g) and cesium carbonate (0.13 g) in N,N-dimethylformamide (2 mL) was added ethyl 4-bromobutyrate (0.028 mL), and the mixture was stirred at 50° C. for 1 hour. After cooling to room temperature, to the reaction mixture was added water, and the mixture was extracted with ethyl acetate. The organic layer was dried over anhydrous sodium sulfate, and the solvent was removed under reduced pressure. The residue was purified by preparative thin layer chromatography on silica gel (eluent: dichloromethane/methanol=9/1) to give 5-[3-(ethoxycarbonyl)propyloxy]-2-(4-ethylbenzyl)phenyl β-D-glucopyranoside (0.028 g).

$^1$H-NMR (CD$_3$OD) δ ppm:
1.18 (3H, t, J=7.6 Hz), 1.23 (3H, t, J=7.1 Hz), 1.95-2.10 (2H, m), 2.48 (2H, t, J=7.5 Hz), 2.57 (2H, q, J=7.6 Hz), 3.30-3.55 (4H, m), 3.68 (1H, dd, J=5.7, 12.1 Hz), 3.80-4.05 (5H, m), 4.12 (2H, q, J=7.1 Hz), 4.88 (1H, d, J=7.4 Hz), 6.49 (1H, dd, J=2.4, 8.8 Hz), 6.77 (1H, d, J=2.4 Hz), 6.92 (1H, d, J=8.8 Hz), 7.00-7.15 (4H, m)

REFERENCE EXAMPLE 116

2-(4-Methoxybenzyl)-5-methoxymethylphenyl β-D-glucopyranoside

To a solution of 2-(4-methoxybenzyl)-5-methoxymethylphenyl 2,3,4,6-tetra-O-acetyl-β-D-glucopyranoside (0.14 g) in methanol (3 mL) was added sodium methoxide (28% methanol solution; 0.047 mL), and the mixture was stirred at room temperature for 3 hours. The reaction mixture was purified by column chromatography on (benzenesulfonylpropyl) silica gel (eluent: methanol) to give 2-(4-methoxybenzyl)-5-methoxymethylphenyl β-D-glucopyranoside (0.084 g).

$^1$H-NMR (CD$_3$OD) δ ppm:
3.35 (3H, s), 3.30-3.55 (4H, m), 3.69 (1H, dd, J=5.5, 12.1 Hz), 3.74 (3H, s), 3.80-3.95 (2H, m), 4.01 (1H, d, J=15.0 Hz), 4.35-4.45 (2H, m), 4.92 (1H, d, J=7.4 Hz), 6.75-6.85 (2H, m), 6.90 (1H, dd, J=1.4, 7.7 Hz), 7.02 (1H, d, J=7.7 Hz), 7.10-7.20 (3H, m)

EXAMPLE 1

2-(4-Ethylbenzyl)-5-hydroxymethylphenyl 6-O-ethoxycarbonyl-β-D-glucopyranoside

To a solution of 2-(4-ethylbenzyl)-5-hydroxymethylphenyl β-D-glucopyranoside (0.075 g) in 2,4,6-trimethypyridine (2 mL) was added ethyl chloroformate (0.037 mL, 2 mol equivalent), and the mixture was stirred at room temperature for 17 hours. To the reaction mixture was added 1 mol/L hydrochloric acid, and the mixture was extracted with ethyl acetate. The extract was washed with 1 mol/L hydrochloric acid and water, and dried over anhydrous magnesium sulfate, and the solvent was removed under reduced pressure. The residue was purified by preparative thin layer chromatography on silica gel (eluent: dichloromethane/-methanol=10/1) and recrystallized (recrystallization solvent: acetone/hexane=1/1) to give 2-(4-ethylbenzyl)-5-hydroxymethylphenyl 6-O-ethoxycarbonyl-β-D-glucopyranoside (0.020 g).

$^1$H-NMR (CD$_3$OD) δ ppm:
1.19 (3H, t, J=7.5 Hz), 1.20-1.30 (3H, m), 2.57 (2H, q, J=7.5 Hz), 3.30-3.55 (3H, m), 3.55-3.65 (1H, m), 3.94 (1H, d, J=15.0 Hz), 4.02 (1H, d, J=15.0 Hz), 4.05-4.20 (2H, m), 4.26 (1H, dd, J=6.6, 11.7 Hz), 4.47 (1H, dd, J=2.3, 11.7 Hz), 4.50-4.60 (2H, m), 4.90 (1H, d, J=7.4 Hz), 6.90-7.15 (7H, m)

EXAMPLE 2-27

The compounds listed in Table 1 were prepared in a similar manner to that described in Example 1 using their corresponding starting materials.

TABLE 1

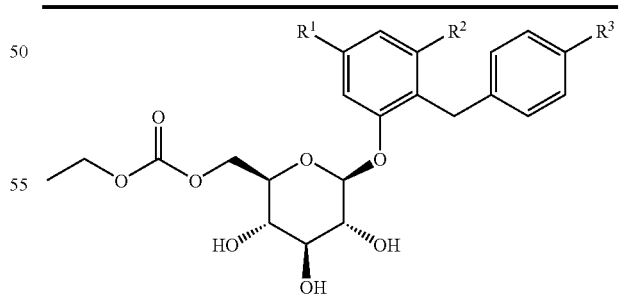

| Example No. | R$^1$ | R$^2$ | R$^3$ |
|---|---|---|---|
| 2 | Hydroxymethyl group | Hydrogen atom | Propoxy group |
| 3 | Hydrogen atom | Hydrogen atom | 3-Hydroxypropyl group |
| 4 | Methyl group | Methyl group | Methoxy group |

TABLE 1-continued

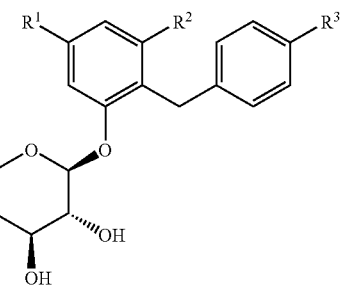

| Example No. | R¹ | R² | R³ |
|---|---|---|---|
| 5 | Hydroxymethyl group | Hydrogen atom | 2-Hydroxyethyl group |
| 6 | Methoxy group | Hydrogen atom | Methoxy group |
| 7 | Methoxymethyl group | Hydrogen atom | Methoxy group |
| 8 | Methyl group | Methyl group | 3-Hydroxypropyl group |
| 9 | Methyl group | Methyl group | 2-Hydroxyethyl group |
| 10 | Amino group | Hydrogen atom | Ethyl group |
| 11 | N-Methylamino group | Hydrogen atom | Ethyl group |
| 12 | Carbamoyl group | Hydrogen atom | Ethyl group |
| 13 | Carbamoylmethyl group | Hydrogen atom | Ethyl group |
| 14 | Cyano group | Hydrogen atom | Methoxy group |
| 15 | Methoxymethyloxy group | Hydrogen atom | Ethyl group |
| 16 | Hydroxy group | Hydrogen atom | Ethyl group |
| 17 | 2-Hydroxyethyloxy group | Hydrogen atom | Ethyl group |
| 18 | 3-(Ethoxycarbonyl)-propyloxy group | Hydrogen atom | Ethyl group |
| 19 | Methoxy group | Hydrogen atom | 2-Hydroxyethyl group |
| 20 | Hydrogen atom | Hydrogen atom | Benzyloxy group |
| 21 | Hydrogen atom | Hydrogen atom | Carboxy group |
| 22 | Hydrogen atom | Hydrogen atom | Allyloxy group |
| 23 | Hydrogen atom | Hydrogen atom | N,N-Dimethylamino group |
| 24 | Hydrogen atom | Hydrogen atom | Methoxycarbonyl group |
| 25 | Hydrogen atom | Hydrogen atom | Cyanomethyl group |
| 26 | Hydrogen atom | Hydrogen atom | Carbamoyl group |
| 27 | Hydrogen atom | Hydrogen atom | (E)-3-Hydroxy-1-propenyl group |

EXAMPLE 28

2-(4-Ethylbenzyl)-5-pivaloyloxymethylphenyl β-D-glucopyranoside

The title compound was prepared in a similar manner to that described in Example 1 using pivaloyl chloride (1.5 mol equivalent) instead of ethyl chloroformate.

$^1$H-NMR (CD$_3$OD) δ ppm:
1.15-1.25 (12H, m), 2.58 (2H, q, J=7.6 Hz), 3.35-3.55 (4H, m), 3.65-3.75 (1H, m), 3.85-3.95 (1H, m), 3.94 (1H, d, J=15.1 Hz), 4.05 (1H, d, J=15.1 Hz), 4.92 (1H, d, J=7.5 Hz), 5.05 (2H, s), 6.91 (1H, dd, J=1.1, 7.8 Hz), 7.03 (1H, d, J=7.8 Hz), 7.07 (2H, d, J=8.0 Hz), 7.13 (2H, d, J=8.0 Hz), 7.16 (1H, d, J=1.1 Hz)

EXAMPLE 29

2-(4-Ethylbenzyl)-5-hydroxymethylphenyl 6-O-butyryl-β-D-glucopyranoside

The title compound was prepared in a similar manner to that described in Example 1 using butyryl chloride (2.5 mol equivalent) instead of ethyl chloroformate.

$^1$H-NMR (CD$_3$OD) δ ppm:
0.90 (3H, t, J=7.4 Hz), 1.19 (3H, t, J=7.6 Hz), 1.50-1.65 (2H, m), 2.25-2.35 (2H, m), 2.58 (2H, q, J=7.6 Hz), 3.30-3.55 (3H, m), 3.55-3.65 (1H, m), 3.95 (1H, d, J=15.1 Hz), 4.02 (1H, d, J=15.1 Hz), 4.21 (1H, dd, J=6.4, 11.8 Hz), 4.35-4.50 (1H, m), 4.55 (2H, s), 4.91 (1H, d, J=7.1 Hz), 6.90-7.15 (7H, m)

EXAMPLE 30

5-Acetoxymethyl-2-(4-ethylbenzyl)phenyl 6-O-acetyl-β-D-glucopyranoside

The title compound was prepared in a similar manner to that described in Example 1 using acetyl chloride (2.5 mol equivalent) instead of ethyl chloroformate.

$^1$H-NMR (CD$_3$OD) δ ppm:
1.19 (3H, t, J=7.6 Hz), 2.03 (3H, s), 2.06 (3H, s), 2.58 (2H, q, J=7.6 Hz), 3.30-3.55 (3H, m), 3.55-3.70 (1H, m), 3.95 (1H, d, J=15.1 Hz), 4.03 (1H, d, J=15.1 Hz), 4.21 (1H, dd, J=6.4, 11.9 Hz), 4.42 (1H, dd, J=2.0, 11.9 Hz), 4.89 (1H, d, J=7.2 Hz), 5.00-5.10 (2H, m), 6.90-7.15 (7H, m)

EXAMPLE 31

2-(4-Ethylbenzyl)-5-(ethoxycarbonyloxymethyl) phenyl β-D-glucopyranoside

The title compound was prepared in a similar manner to that described in Example 1.

$^1$H-NMR (CD$_3$OD) δ ppm:
1.19 (3H, t, J=7.6 Hz), 1.26 (3H, t, J=7.1 Hz), 2.58 (2H, q, J=7.6 Hz), 3.35-3.55 (4H, m), 3.71 (1H, dd, J=5.0, 12.0 Hz), 3.89 (1H, dd, J=1.9, 12.0 Hz), 3.95 (1H, d, J=15.0 Hz), 4.05 (1H, d, J=15.0 Hz), 4.16 (2H, q, J=7.1 Hz), 4.92 (1H, d, J=7.4 Hz), 5.00-5.15 (2H, m), 6.94 (1H, dd, J=1.4, 7.7 Hz), 7.04 (1H, d, J=7.7 Hz), 7.07 (2H, d, J=8.0 Hz), 7.13 (2H, d, J=8.0 Hz), 7.19 (1H, d, J=1.4 Hz)

EXAMPLE 32

2-(4-Ethylbenzyl)-5-hydroxymethylphenyl 6-O-hexanoyl-β-D-glucopyranoside

The title compound was prepared in a similar manner to that described in Example 1 using hexanoyl chloride (2.5 mol equivalent) instead of ethyl chloroformate.

$^1$H-NMR (CD$_3$OD) δ ppm:
0.86 (3H, t, J=7.1 Hz), 1.19 (3H, t, J=7.6 Hz), 1.20-1.35 (4H, m), 1.50-1.65 (2H, m), 2.25-2.40 (2H, m), 2.50-2.65 (2H, m), 3.30-3.55 (3H, m), 3.55-3.65 (1H, m), 3.95 (1H, d, J=14.9 Hz), 4.02 (1H, d, J=14.9 Hz), 4.21 (1H, dd, J=6.3, 11.9 Hz), 4.35-4.50 (1H, m), 4.55 (2H, s), 4.91 (1H, d, J=7.2 Hz), 6.85-7.20 (7H, m)

EXAMPLE 33

2-(4-Ethylbenzyl)-5-hydroxymethylphenyl 6-O-pivaloyl-β-D-glucopyranoside

The title compound was prepared in a similar manner to that described in Example 1 using pivaloyl chloride (1.5 mol equivalent) instead of ethyl chloroformate.

$^1$H-NMR (CD$_3$OD) δ ppm:

1.14 (9H, s), 1.19 (3H, t, J=7.6 Hz), 2.57 (2H, q, J=7.6 Hz), 3.30-3.50 (3H, m), 3.50-3.65 (1H, m), 3.95 (1H, d, J=14.8 Hz), 4.01 (1H, d, J=14.8 Hz), 4.17 (1H, dd, J=6.3, 11.8 Hz), 4.42 (1H, dd, J=2.2, 11.8 Hz), 4.54 (2H, s), 4.90-5.00 (1H, m), 6.90-7.15 (7H, m)

EXAMPLE 34

2-(4-Ethylbenzyl)-5-hydroxymethylphenyl 6-O-isobutyloxycarbonyl-β-D-glucopyranoside The title compound was prepared in a similar manner to that described in Example 1 using isobutyl chloroformate (2.0 mol equivalent) instead of ethyl chloroformate.

$^1$H-NMR (CD$_3$OD) δ ppm:
0.89 (6H, d, J=6.6 Hz), 1.17 (3H, t, J=7.6 Hz), 1.80-1.95 (1H, m), 2.56 (2H, q, J=7.6 Hz), 3.40-3.60 (3H, m), 3.60-3.70 (1H, m), 3.80-3.90 (2H, m), 3.94 (1H, d, J=15.0 Hz), 4.02 (1H, d, J=15.0 Hz), 4.29 (1H, dd, J=5.9, 11.7 Hz), 4.49 (1H, dd, J=2.0, 11.7 Hz), 4.56 (2H, s), 4.80-5.00 (1H, m), 6.90-7.20 (7H, m)

EXAMPLE 35

2-(4-Ethylbenzyl)-5-hydroxymethylphenyl 6-O-isopropyloxycarbonyl-β-D-glucopyranoside The title compound was prepared in a similar manner to that described in Example 1 using isopropyl chloroformate (2.0 mol equivalent) instead of ethyl chloroformate.

$^1$H-NMR (CD$_3$OD) δ ppm:
1.19 (3H, t, J=7.5 Hz), 1.22 (3H, d, J=6.1 Hz), 1.24 (3H, d, J=6.1 Hz), 2.57 (2H, q, J=7.5 Hz), 3.30-3.55 (3H, m), 3.55-3.70 (1H, m), 3.95 (1H, d, J=15.0 Hz), 4.02 (1H, d, J=15.0 Hz), 4.25 (1H, dd, J=6.3, 11.7 Hz), 4.46 (1H, dd, J=2.3, 11.7 Hz), 4.50-4.60 (2H, m), 4.70-4.85 (1H, m), 4.85-4.95 (1H, m), 6.90-7.20 (7H, m)

EXAMPLE 36

2-[4-(2-Benzyloxyethyl)benzyl]phenyl 6-O-ethoxycarbonyl-β-D-glucopyranoside

The title compound was prepared in a similar manner to that described in Example 1 using 2-[4-(2-benzyloxyethyl)-benzyl]phenyl β-D-glucopyranoside instead of 2-(4-ethylbenzyl)-5-hydroxymethylphenyl β-D-glucopyranoside.

$^1$H-NMR (CD$_3$OD) δ ppm:
1.22 (3H, t, J=7.1 Hz), 2.84 (2H, t, J=7.0 Hz), 3.35-3.40 (1H, m), 3.40-3.55 (2H, m), 3.55-3.65 (1H, m), 3.66 (2H, t, J=7.0 Hz), 3.97 (1H, d, J=15.3 Hz), 4.06 (1H, d, J=15.3 Hz), 4.05-4.20 (2H, m), 4.28 (1H, dd, J=6.1, 11.7 Hz), 4.44 (1H, dd, J=2.1, 11.7 Hz), 4.48 (2H, s), 4.89 (1H, d, J=7.8 Hz), 6.85-6.95 (1H, m), 7.00-7.05 (1H, m), 7.05-7.20 (6H, m), 7.20-7.35 (5H, m)

EXAMPLE 37

2-[4-(2-Hydroxyethyl)benzyl]phenyl 6-O-ethoxycarbonyl-β-D-glucopyranoside

To a solution of 2-[4-(2-benzyloxyethyl)benzyl]phenyl 6-O-ethoxycarbonyl-β-D-glucopyranoside (0.18 g) in ethyl acetate (4 mL) and ethanol (1 mL) was added 10% palladium-carbon powder (0.072 g), and the mixture was stirred under a hydrogen atmosphere at room temperature for 18 hours. Insoluble materials were removed by filtration, and the solvent of the filtrate was removed under reduced pressure. The residue was purified by column chromatography on silica gel (eluent: dichloromethane/methanol=20/1-10/1) to give 2-[4-(2-hydroxyethyl)benzyl]phenyl 6-O-ethoxycarbonyl-β-D-glucopyranoside (0.11 g).

$^1$H-NMR (CD$_3$OD) δ ppm:
1.23 (3H, t, J=7.0 Hz), 2.76 (2H, t, J=7.1 Hz), 3.30-3.55 (3H, m), 3.55-3.65 (1H, m), 3.71 (2H, t, J=7.1 Hz), 3.96 (1H, d, J=15.1 Hz), 4.05 (1H, d, J=15.1 Hz), 4.05-4.20 (2H, m), 4.29 (1H, dd, J=6.5, 11.7 Hz), 4.44 (1H, dd, J=2.2, 11.7 Hz), 4.88 (1H, d, J=7.5 Hz), 6.85-6.95 (1H, m), 7.00-7.05 (1H, m), 7.05-7.20 (6H, m)

EXAMPLE 38

2-[4-(2-Benzyloxyethyl)benzyl]phenyl 6-O-acetyl-β-D-glucopyranoside

The title compound was prepared in a similar manner to that described in Example 36 using acetyl chloride instead of ethyl chloroformate.

$^1$H-NMR (CD$_3$OD) δ ppm:
2.01 (3H, s), 2.84 (2H, t, J=6.9 Hz), 3.30-3.55 (3H, m), 3.55-3.65 (1H, m), 3.66 (2H, t, J=6.9 Hz), 3.97 (1H, d, J=14.9 Hz), 4.06 (1H, d, J=14.9 Hz), 4.23 (1H, dd, J=6.4, 11.9 Hz), 4.38 (1H, dd, J=2.2, 11.9 Hz), 4.48 (2H, s), 4.89 (1H, d, J=7.4 Hz), 6.85-6.95 (1H, m), 7.00-7.05 (1H, m), 7.05-7.20 (6H, m), 7.20-7.35 (5H, m)

EXAMPLE 39

2-[4-(2-Hydroxyethyl)benzyl]phenyl 6-O-acetyl-β-D-glucopyranoside

The title compound was prepared in a similar manner to that described in Example 37 using 2-[4-(2-benzyloxyethyl)-benzyl]phenyl 6-O-acetyl-β-D-glucopyranoside instead of 2-[4-(2-benzyloxyethyl)benzyl]phenyl 6-O-ethoxycarbonyl-β-D-glucopyranoside.

$^1$H-NMR (CD$_3$OD) δ ppm:
2.02 (3H, s), 2.76 (2H, t, J=7.1 Hz), 3.30-3.55 (3H, m), 3.55-3.65 (1H, m), 3.71 (2H, t, J=7.1 Hz), 3.96 (1H, d, J=15.0 Hz), 4.05 (1H, d, J=15.0 Hz), 4.23 (1H, dd, J=6.4, 11.8 Hz), 4.38 (1H, dd, J=2.2, 11.8 Hz), 4.88 (1H, d, J=7.8 Hz), 6.90-6.95 (1H, m), 7.00-7.20 (7H, m)

EXAMPLE 40

2-[4-(2-Acetoxyethyl)benzyl]phenyl 6-O-acetyl-β-D-glucopyranoside

The title compound was prepared in a similar manner to that described in Example 38 using 2-[4-(2-hydroxyethyl)-benzyl]phenyl 6-O-acetyl-β-D-glucopyranoside instead of 2-[4-(2-benzyloxyethyl)benzyl]phenyl 6-O-acetyl-β-D-glucopyranoside.

$^1$H-NMR (CD$_3$OD) δ ppm:
1.98 (3H, s), 2.02 (3H, s), 2.86 (2H, t, J=6.9 Hz), 3.30-3.55 (3H, m), 3.55-3.65 (1H, m), 3.97 (1H, d, J=15.1 Hz), 4.06

(1H, d, J=15.1 Hz), 4.15-4.30 (3H, m), 4.38 (1H, dd, J=2.2, 12.2 Hz), 4.89 (1H, d, J=7.6 Hz), 6.90-7.00 (1H, m), 7.00-7.20 (7H, m)

TEST EXAMPLE 1

Assay for Inhibitory Effect on Human SGLT2 Activity

1) Construction of the Plasmid Vector Expressing Human SGLT2

Preparation of the cDNA library for PCR amplification was performed by reverse transcription of a total RNA deprived from human kidney (Ori gene) with oligo dT as the primer, using SUPERSCRIPT Preamplification System (Gibco-BRL: LIFE TECHNOLOGIES). The DNA fragment coding for human SGLT2 was amplified by the PCR reaction, in which the human kidney cDNA library described above was used as the template and the following oligo nucleotides 0702F and 0712R, presented as SEQ ID NO:1 and SEQ ID NO:2 respectively, were used as the primers. The amplified DNA fragment was ligated into pCR-Blunt (Invitrogen), a vector for cloning, according to standard method of the kit. The *Escherichia coli* HB101 was transformed according to usual method and then selection of the transformants was performed on the LB agar medium containing 50 µg/mL of kanamycin. After plasmid DNA was extracted and purified from the one of the transformants, amplifying of the DNA fragment coding for human SGLT2 was performed by the PCR reaction, in which the following oligo nucleotides 0714F and 0715R, presented as SEQ ID NO:3 and SEQ ID NO:4 respectively, were used as the primers. The amplified DNA fragment was digested with restriction enzymes, Xho I and Hind III, and then purified with Wizard Purification System (Promega). This purified DNA fragment was inserted at the corresponding restriction sites of pcDNA3.1 (−) Myc/His-B (Invitrogen), a vector for expressing of fusion protein. The *Escherichia coli* HB101 was transformed according to usual method and then selection of the transformant was performed on the LB agar medium containing 50 µg/mL of ampicillin. After plasmid DNA was extracted and purified from this transformant, the base sequence of the DNA fragment inserted at the multi-cloning sites of the vector pcDNA3.1 (−) Myc/His-B was analyzed. This clone had a single base substitution (ATC which codes for the isoleucine-433 was substituted by GTC) compared with the human SGLT2 reported by Wells et al. (Am. J. Physiol., Vol. 263, pp. 459-465 (1992)). Sequentially, a clone in which valine is substituted for isoleucine-433 was obtained. This plasmid vector expressing human SGLT2 in which the peptide presented as SEQ ID NO:5 is fused to the carboxyl terminal alanine residue was designated KL29.

```
SEQ ID NO: 1    ATGGAGGAGCACACAGAGGC

SEQ ID NO: 2    GGCATAGAAGCCCCAGAGGA

SEQ ID NO: 3    AACCTCGAGATGGAGGAGCACACAGAGGC

SEQ ID NO: 4    AACAAGCTTGGCATAGAAGCCCCAGAGGA

SEQ ID NO: 5    KLGPEQKLISEEDLNSAVDHHHHHH
```

2) Preparation of the Cells Expressing Transiently Human SGLT2

KL29, the plasmid coding human SGLT2, was transfected into COS-7 cells (RIKEN CELL BANK RCB0539) by electroporation. Electroporation was performed with GENE PULSER II (Bio-Rad Laboratories) under the condition: 0.290 kV, 975 µF, $2\times10^6$ cells of COS-7 cell and 20 µg of KL29 in 500 µL of OPTI-MEM I medium (Gibco-BRL: LIFE TECHNOLOGIES) in the 0.4 cm type cuvette. After the gene transfer, the cells were harvested by centrifugation and resuspended with OPTI-MEM I medium (1 mL/cuvette). To each well in 96-wells plate, 125 µL of this cell suspension was added. After overnight culture at 37° C. under 5% $CO_2$, 125 µL of DMEM medium which is containing 10% of fetal bovine serum (Sanko Jyunyaku), 100 units/mL sodium penicillin G (Gibco-BRL: LIFE TECHNOLOGIES), and 100 µg/mL streptomycin sulfate (Gibco-BRL: LIFE TECHNOLOGIES) was added to each well. These cells were cultured until the next day and then they were used for the measurement of the inhibitory activity against the uptake of methyl-α-D-glucopyranoside.

3) Measurement of the Inhibitory Activity Against the Uptake of methyl-α-D-glucopyranoside After a test compound was dissolved in dimethyl sulfoxide and diluted with the uptake buffer (a pH 7.4 buffer containing 140 mM sodium chloride, 2 mM potassium chloride, 1 mM calcium chloride, 1 mM magnesium chloride, 5 mM methyl-α-D-glucopyranoside, 10 mM 2-[4-(2-hydroxyethyl)-1-piperazinyl]ethane sulfonic acid and 5 mM tris (hydroxymethyl)aminomethane), each diluent was used as test sample for measurement of the inhibitory activity. After removal of the medium of the COS-7 cells expressing transiently human SGLT2, to each well 200 µL of the pretreatment buffer (a pH 7.4 buffer containing 140 mM choline chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris(hydroxymethyl)-aminomethane) was added, and the cells were incubated at 37° C. for 10 minutes. After the pretreatment buffer was removed, 200 µL of the same buffer was added again, and the cells were incubated at 37° C. for 10 minutes. The buffer for measurement was prepared by adding and mixing 7 µL of methyl-α-D-(U-14C)glucopyranoside (Amersham Pharmacia Biotech) to 525 µL of the prepared test sample. For the control, the buffer for measurement without any test compound was prepared. For estimate of the basal uptake in the absence of a test compound and sodium, the buffer for measurement of the basal uptake, which contains 140 mM choline chloride in place of sodium chloride, was prepared similarly. After the pretreatment buffer was removed, 75 µL of the each buffer for measurement was added to each well, and the cells were incubated at 37° C. for 2 hours. After the buffer for measurement was removed, 200 µL of the washing buffer (a pH 7.4 buffer containing 140 mM choline chloride, 2 mM potassium chloride, 1 mM calcium chloride, 1 mM magnesium chloride, 10 mM methyl-α-D-glucopyranoside, 10 mM 2-[4-(2-hydroxyethyl)-1-piperazinyl]ethane sulfonic acid and 5 mM tris (hydroxymethyl)aminomethane) was added to each well and immediately removed. After two additional washing, the cells were solubilized by addition of 75 µL of 0.2 mol/L sodium hydroxide to each well. After the cell lysates were transferred to the PicoPlate (Packard) and 150 µL of MicroScint-40 (Packard) was added to each well, the radioactivity was measured with microplate scintillation counter TopCount (Packard). The difference in uptake was obtained as 100% value by subtracting the radioactivity in the basal uptake from that in control and then the concentrations at which 50% of uptake were inhibited ($IC_{50}$) were calculated from the concentration-inhibition curve by least square method. The results are shown in the following Table 2.

TABLE 2

| Test compound | IC$_{50}$ value (nM) |
| --- | --- |
| Reference Example 13 | 8.1 |
| Reference Example 14 | 140 |
| Reference Example 15 | 27 |
| Reference Example 16 | 210 |
| Reference Example 17 | 75 |
| Reference Example 49 | 120 |
| Reference Example 103 | 10 |
| Reference Example 104 | 30 |
| Reference Example 105 | 59 |
| Reference Example 111 | 290 |

TEST EXAMPLE 2

Assay for Oral Absorbability

1) Preparation of the Samples for Measurement of the Drug Concentration after Intravenous Injection to the Tail Vein As experimental animals, overnight fasted SD rats (CLEA JAPAN, INC., male, 5 weeks of age, 135-180 g) were used. Sixty mg of a test compound was dissolved by adding of 1.8 mL of ethanol, 7.2 mL of polyethylene glycol 400 and 9 mL of saline, and then 3.3 mg/mL solution was prepared. The body weights of rats were measured and the solution of the test compound was intravenously injected to the tail vein of unanesthetized rats at the dose of 3 mL/kg (10 mg/kg). The intravenous injection to the tail was performed with 26 G injection needle and 1 mL syringe. The sampling times for collection of blood were 2, 5, 10, 20, 30, 60 and 120 minutes after the intravenous injection to the tail. The blood was centrifuged and the plasma was used as the sample for measurement of the drug concentration in plasma.

2) Preparation of the Samples for Measurement of the Drug Concentration after Oral Administration As experimental animals, overnight fasted SD rats (CLEA JAPAN, INC., male, 5 weeks of age, 135-180 g) were used. A test compound was suspended or dissolved in 0.5% sodium carboxymethylcellulose solution at the concentration of 1 mg/mL of its active form. After the bodyweights of rats were measured, the liquid containing test compound described above was orally administered at the dose of 10 mL/kg (10 mg/kg as the active form). The oral administration was performed with gastric tube for rat and 2.5 mL syringe. The sampling times for collection of blood were 15, 30, 60, 120 and 240 minutes after the oral administration. The blood was centrifuged and the plasma was used as the sample for measurement of the drug concentration in plasma.

3) Measurement of Drug Concentration

To 0.1 mL of the plasma obtained in 1) and 2) described above was added an adequate amount of an adequate internal standard material according to usual method, and then deproteinization was performed by adding of 1 mL of methanol. After centrifugation, the methanol phase was evaporated to dryness under a stream of nitrogen. The residue was dissolved in 300 µL of the following mobile phase (1) or (2), and 30 µL aliquot of the solution was injected into HPLC. The drug concentration in plasma was measured by HPLC method under the condition as follows. To 0.1 mL of the blank plasma were adequately added an adequate internal standard and various concentrations of the corresponding active form of the compound according to usual method, similar operating described above was done and then the standard curve was prepared.

Column: Inertsil ODS-2 (4.6×250 mm)

Mobile phase (1): acetonitrile/10 mM phosphate buffer (pH 3.0)=26:74 (v/v)

Mobile phase (2): acetonitrile/10 mM phosphate buffer (pH 3.0)=22:78 (v/v)

Column temperature: 50° C.

Flow rate: 1.0 mL/minute

Wavelength for measurement: UV 232 nm

Each area under the plasma concentration-time curve by intravenous injection to the tail vein and oral administration of the test compound was estimated with WinNonlin Standard made by Pharsight Corporation from the plasma concentrations at each time obtained from HPLC mentioned above and then the bioavailability (%) was calculated based on the following formula. The results are shown in the following Table 3.

Bioavailability (%)=(Area under the Plasma Concentration–Time Curve by Oral Administration/Area under the Plasma Concentration–Time Curve by Intravenous Injection to the Tail Vein)×100

TABLE 3

| Test compound | Mobile phase | Bioavailability (%) |
| --- | --- | --- |
| Example 1 | (1) | 43 |
| Example 28 | (1) | 54 |
| Example 29 | (1) | 80 |
| Example 30 | (1) | 65 |
| Example 32 | (1) | 49 |
| Example 33 | (1) | 44 |
| Example 34 | (1) | 73 |
| Example 40 | (2) | 65 |
| Reference Example 13 | (1) | 0 |
| Reference Example 16 | (2) | 9 |

TEST EXAMPLE 3

Assay for the Facilitatory Effect on Urinary Glucose Excretion

As experimental animals, overnight fasted SD rats (Japan SLC. Inc., male, 7-8 weeks of age, 205-272 g) were used. A Test compound was suspended in 0.5% sodium carboxymethylcellulose solution at the concentration of 2 mg/mL. When a homogenous suspension was not obtained in this condition, the test compound was dissolved in ethanol at the concentration of 100 mg/mL of its active form and then 2 mg/mL suspension was obtained by adding this solution to 49 times volumes of 0.5% sodium carboxymethylcellulose solution. Apart of this suspension was diluted with 0.5% sodium carboxymethylcellulose solution and then 0.6 and 0.2 mg/mL suspensions were prepared. After the body weights of rats were measured, the test suspension was orally administered at the dose of 5 mL/kg (1, 3 and 10 mg/kg). For control, just only 0.5% sodium carboxymethylcellulose solution was orally administered at the dose of 5 mL/kg. Immediately after this oral administration, 500 g/L sucrose solution was orally administered at the dose of 5 mL/kg (2.5 g/kg). The oral administration was performed with gastric tube for rat and 2.5 mL syringe. The head count in one group was 3. Collection of urine was performed in metabolic cage after the sucrose administration was finished. The sampling time for collection of urine was 24 hours after the sucrose administration. After collection of urine was finished, the urine volume was recorded and the urinary glucose concentration was measured. The glucose concentration was measured with a kit for laboratory test: Glucose B-Test WAKO (Wako Pure Chemical Industries, Ltd.). The amount of urinary glucose excretion in 24 hours per 200 g of body weight was calculated from urine volume, urinary glucose concentration and body weight. The results are shown in the following Table 4.

TABLE 4

| Test compound | Dose (mg/kg) | Amount of urinary glucose excretion (mg/24 hours/ 200 g body weight) |
|---|---|---|
| Example 1 | 1 | 7.0 |
|  | 3 | 82.1 |
|  | 10 | 195.8 |
| Example 40 | 1 | 0.0 |
|  | 3 | 4.1 |
|  | 10 | 55.9 |

TEST EXAMPLE 4

Acute Toxicity Test

A 100 mg/mL suspension was prepared by adding 0.5% sodium carboxymethylcellulose solution to a test compound. Five week old male SD rat (CLEA JAPAN, INC., 124-128 g, 5 animals in each group) were used as test animals after fasted overnight. The above-mentioned suspension was orally administered at the dose 10 mL/kg (1000 mg/kg) to the test animals, and observation was performed for 24 hours. The results are shown in the following Table 5.

TABLE 5

| Test compound | Number of death |
|---|---|
| Example 1 | 0/5 |

INDUSTRIAL APPLICABILITY

The glucopyranosyloxybenzylbenzene derivatives represented by the above general formula (I) of the present invention or pharmaceutically acceptable salts thereof have an improved oral absorption. In addition, they show an excellent hypoglycemic effect by excreting excess glucose into the urine through preventing the reabsorption of glucose at the kidney because they are converted into glucopyranosyloxybenzylbenzene derivatives represented by the above general formula (II) as their active forms in vivo and exhibit a potent inhibitory activity in human SGLT2. Therefore, the present invention can provide drugs for the prevention or treatment of a disease associated with hyperglycemia such as diabetes, diabetic complications, obesity or the like, which are also suitable as oral formulations.

[Sequence Listing Free Text]

SEQ ID NO:1 Synthetic DNA primer

SEQ ID NO:2 Synthetic DNA primer

SEQ ID NO:3 Synthetic DNA primer

SEQ ID NO:4 Synthetic DNA primer

SEQ ID NO:5 Peptide fused to the carboxyl terminal alanine residue of human SGLT2

The invention claimed is:

1. A glucopyranosyloxybenzylbenzene derivative represented by the general formula:

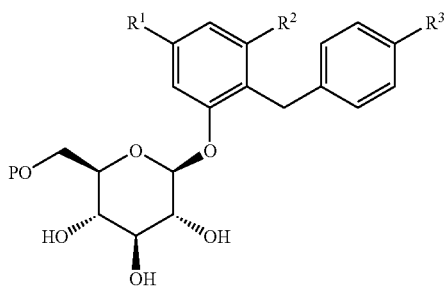

wherein P represents a hydrogen atom or a group forming a prodrug; $R^1$ represents an amino group, a mono or di(lower alkyl)-substituted amino group, a cyano group, a carbamoyl group, a carbamoyl(lower alkyl) group, a lower alkoxycarbonyl-substituted (lower alkyl) group, a lower alkoxycarbonyl-substituted (lower alkoxy) group, a carboxy(lower alkyl) group, or a carboxy(lower alkoxy) group; $R^2$ represents a hydrogen atom or a lower alkyl group; $R^3$ represents a lower alkyl group, a lower alkoxy group, a lower alkylthio group, a lower alkenyloxy group, an aralkyloxy group, a lower alkoxy-substituted (lower alkyl) group, a lower alkoxy-substituted (lower alkoxy) group, a lower alkoxy-substituted (lower alkylthio) group, a carboxy group, a lower alkoxycarbonyl group, a cyano group, an aralkyloxy(lower alkyl) group, a cyano (lower alkyl) group, a carbamoyl group, a carbamoyl(lower alkyl) group, an amino group, a mono or di(lower alkyl)-substituted amino group, a lower alkoxycarbonyl-substituted (lower alkyl) group, a lower alkoxycarbonyl-substituted (lower alkoxy) group, a carboxy(lower alkyl) group, a carboxy(lower alkoxy) group, or a group represented by the general formula: $P^2$—O—$A^2$— wherein $P^2$ represents a hydrogen atom or a group forming a prodrug; and $A^2$ represents a lower alkylene group, a lower alkyleneoxy group, a lower alkylenethio group, or a lower alkenylene group; and with the proviso at least one of P and $P^2$ represents a group forming a prodrug or a pharmaceutically acceptable salt thereof.

2. A glucopyranosyloxybenzylbenzene derivative as claimed in claim 1, represented by the general formula:

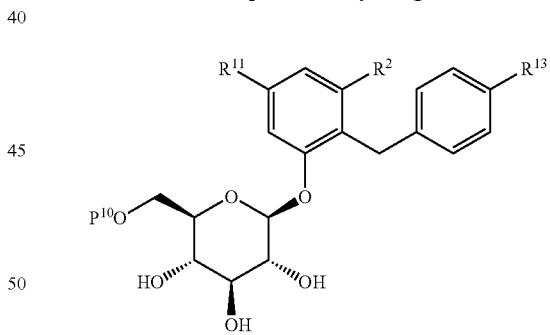

wherein $P^{10}$ represents a hydrogen atom, a lower acyl group, a lower alkoxy-substituted (lower acyl) group, a lower alkoxycarbonyl-substituted (lower acyl) group, a lower alkoxycarbonyl group or a lower alkoxy-substituted (lower alkoxycarbonyl) group; $R^{11}$ represents an amino group, a mono or di(lower alkyl)-substituted amino group, a cyano group, a carbamoyl group, a carbamoyl(lower alkyl) group, a lower alkoxycarbonyl-substituted (lower alkyl) group, a lower alkoxycarbonyl-substituted (lower alkoxy) group, a carboxy(lower alkyl) group, or a carboxy(lower alkoxy) group; $R^2$ represents a hydrogen atom or a lower alkyl group; $R^{13}$ represents a lower alkyl group, a lower alkoxy group, a lower alkylthio group, a lower alkenyloxy group, an aralkyloxy group, a lower alkoxy-substituted (lower alkyl) group, a lower alkoxy-substituted (lower alkoxy) group, a lower alkoxy-substituted (lower alkylthio) group, a carboxy group, a lower alkoxycarbonyl group, a cyano group, an aralkyloxy (lower alkyl) group, a cyano(lower alkyl) group, a carbamoyl group, a carbamoyl(lower alkyl) group, an amino group, a mono or di(lower alkyl)-substituted amino group, a lower alkoxycarbonyl-substituted (lower alkyl) group, a lower alkoxycarbonyl-substituted (lower alkoxy) group, a carboxy (lower alkyl) group, a carboxy(lower alkoxy) group or a group represented by the general formula: $P^{12}$—O—$A^2$— wherein $P^{12}$ represents a hydrogen atom, a lower acyl group, a lower alkoxy-substituted (lower acyl) group, a lower alkoxycarbonyl-substituted (lower acyl) group, a lower alkoxycarbonyl group or a lower alkoxy-substituted (lower alkoxycarbonyl) group; and $A^2$ represents a lower alkylene group, a lower alkyleneoxy group, a lower alkylenethio group or a lower alkenylene group; and with the proviso at least one of $P^{10}$ and $P^{12}$ represents a lower acyl group, a lower alkoxy-substituted (lower acyl) group, a lower alkoxycarbonyl-substituted (lower acyl) group, a lower alkoxycarbonyl group or a lower alkoxy-substituted (lower alkoxycarbonyl) group, or a pharmaceutically acceptable salt thereof.

3. A glucopyranosyloxybenzylbenzene derivative as claimed in claim 2, represented by the general formula:

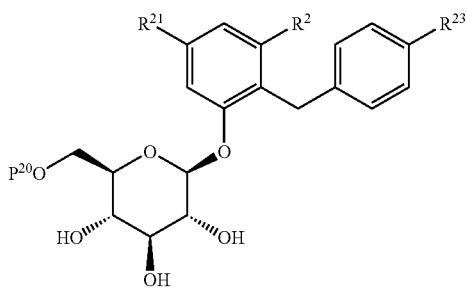

wherein $P^{20}$ represents a hydrogen atom, a lower acyl group or a lower alkoxycarbonyl group; $R^{21}$ represents an amino group, a mono or di(lower alkyl)-substituted amino group, a cyano group, a carbamoyl group, a carbamoyl(lower alkyl) group, a lower alkoxycarbonyl-substituted (lower alkyl) group, a lower alkoxycarbonyl-substituted (lower alkoxy) group, a carboxy(lower alkyl) group, or a carboxy(lower alkoxy) group; $R^2$ represents a hydrogen atom or a lower alkyl group; $R^{23}$ represents a lower alkyl group, a lower alkoxy group, a lower alkylthio group, a lower alkenyloxy group, an aralkyloxy group, a lower alkoxy-substituted (lower alkyl) group, a lower alkoxy-substituted (lower alkoxy) group, a lower alkoxy-substituted (lower alkylthio) group, a carboxy group, a lower alkoxycarbonyl group, a cyano group, an aralkyloxy(lower alkyl) group, a cyano(lower alkyl) group, a carbamoyl group, a carbamoyl(lower alkyl) group, an amino group, a mono or di(lower alkyl)-substituted amino group, a lower alkoxycarbonyl-substituted (lower alkyl) group, a lower alkoxycarbonyl-substituted (lower alkoxy) group, a carboxy(lower alkyl) group, a carboxy(lower alkoxy) group or a group represented by the general formula: $P^{22}$—O—$A^2$— wherein $P^{22}$ represents a hydrogen atom, a lower acyl group or a lower alkoxycarbonyl group; and A represents a lower alkylene group, a lower alkyleneoxy group, a lower alkylenethio group or a lower alkenylene group; and with the proviso that at least one of $P^{20}$ and $P^{22}$ represents a lower acyl group or a lower alkoxycarbonyl group, or a pharmaceutically acceptable salt thereof.

4. A pharmaceutical composition comprising as an active ingredient a glucopyranosyloxybenzylbenzene derivative as claimed in any one of claims 1, 2 and 3 or a pharmaceutically acceptable salt thereof in combination with a pharmaceutically acceptable additive.

5. A pharmaceutical composition as claimed in claim 4 wherein the composition is an oral formulation.

6. A method for the treatment of a disease associated with hyperglycemia, which comprises administering an effective amount of a glucopyranosyloxybenzylbenzene derivative as claimed in claim 1 or a pharmaceutically acceptable salt thereof to a patient in need of said treatment.

* * * * *